United States Patent
Shin et al.

(10) Patent No.: US 9,990,080 B2
(45) Date of Patent: Jun. 5, 2018

(54) TOUCH INPUT SENSING METHOD FOR REDUCING INFLUENCE OF PARASITIC CAPACITANCE AND DEVICE THEREFOR

(71) Applicant: SENTRON INC., Daejeon (KR)

(72) Inventors: Hyung-Cheol Shin, Daejeon (KR); Il-Hyun Yun, Daejeon (KR)

(73) Assignee: SENTRON INC. (KR)

( * ) Notice: Subject to any disclaimer, the term of this patent is extended or adjusted under 35 U.S.C. 154(b) by 72 days.

(21) Appl. No.: 15/036,342

(22) PCT Filed: Nov. 11, 2014

(86) PCT No.: PCT/KR2014/010797
§ 371 (c)(1),
(2) Date: May 12, 2016

(87) PCT Pub. No.: WO2015/072722
PCT Pub. Date: May 21, 2015

(65) Prior Publication Data
US 2016/0283023 A1  Sep. 29, 2016

(30) Foreign Application Priority Data

Nov. 12, 2013 (KR) .................. 10-2013-0137280
Dec. 16, 2013 (KR) .................. 10-2013-0156495
(Continued)

(51) Int. Cl.
*G06F 3/041* (2006.01)
*G06F 3/044* (2006.01)
(Continued)

(52) U.S. Cl.
CPC ............ *G06F 3/0416* (2013.01); *A61M 5/31* (2013.01); *G02F 1/1368* (2013.01);
(Continued)

(58) Field of Classification Search
CPC .......... G06F 2203/04106; G06F 3/046; G06F 3/0418; G06F 3/0416; G06F 3/0412;
(Continued)

(56) References Cited

U.S. PATENT DOCUMENTS

2011/0148440 A1  6/2011  Bruwer et al.
2012/0038585 A1*  2/2012  Kim ..................... G06F 3/0412
                                                345/174
(Continued)

FOREIGN PATENT DOCUMENTS

WO    2013048195 A9    4/2013
WO    2013111998 A1    8/2013
WO   20130129849 A1    9/2013

OTHER PUBLICATIONS

International Search Report for International Application No. PCT/KR2014/010797 dated Feb. 10, 2015.

*Primary Examiner* — Abhishek Sarma
(74) *Attorney, Agent, or Firm* — Kunzler, PC

(57) ABSTRACT

Disclosed is a touch input sensing device comprising: a touch input sensing electrode; a touch sensing unit connected to one point of the touch input sensing electrode to measure a change in a touch capacitance formed by the touch input sensing electrode according to a touch input; a second node included in the touch input sensing device to form a capacitance between the one point and the second node; and a potential control unit for providing a potential value following the potential of the one point to the second node to decrease a potential difference between the one point and the second node.

18 Claims, 35 Drawing Sheets

(30) Foreign Application Priority Data

Dec. 19, 2013 (KR) .................. 10-2013-0159767
Dec. 31, 2013 (KR) .................. 10-2013-0169549
Feb. 8, 2014 (KR) .................. 10-2014-0014491

(51) Int. Cl.

| | | |
|---|---|---|
| *A61M 5/31* | (2006.01) | |
| *G02F 1/1333* | (2006.01) | |
| *G02F 1/1343* | (2006.01) | |
| *G02F 1/1362* | (2006.01) | |
| *G02F 1/1368* | (2006.01) | |
| *G06F 3/046* | (2006.01) | |

(52) U.S. Cl.
CPC .... *G02F 1/13338* (2013.01); *G02F 1/134336* (2013.01); *G02F 1/134363* (2013.01); *G02F 1/136286* (2013.01); *G06F 3/044* (2013.01); *G06F 3/0412* (2013.01); *G06F 3/0418* (2013.01); *A61M 2205/505* (2013.01); *G06F 3/046* (2013.01); *G06F 2203/04106* (2013.01); *G06F 2203/04111* (2013.01)

(58) Field of Classification Search
CPC ........... G06F 2203/04111; G06F 3/044; G02F 1/1368; G02F 1/134363; G02F 1/134336; G02F 1/136286; G02F 1/13338; A61M 2205/505; A61M 5/31
See application file for complete search history.

(56) References Cited

U.S. PATENT DOCUMENTS

| | | | |
|---|---|---|---|
| 2012/0105080 A1 | 5/2012 | Iwasawa et al. | |
| 2012/0206403 A1* | 8/2012 | Wang | G02F 1/13338 345/174 |
| 2014/0232691 A1* | 8/2014 | Lee | G06F 3/044 345/174 |
| 2014/0375609 A1* | 12/2014 | Kim | G06F 3/0418 345/174 |
| 2015/0009179 A1* | 1/2015 | Kim | G06F 3/044 345/174 |

* cited by examiner

[Fig. 1a]
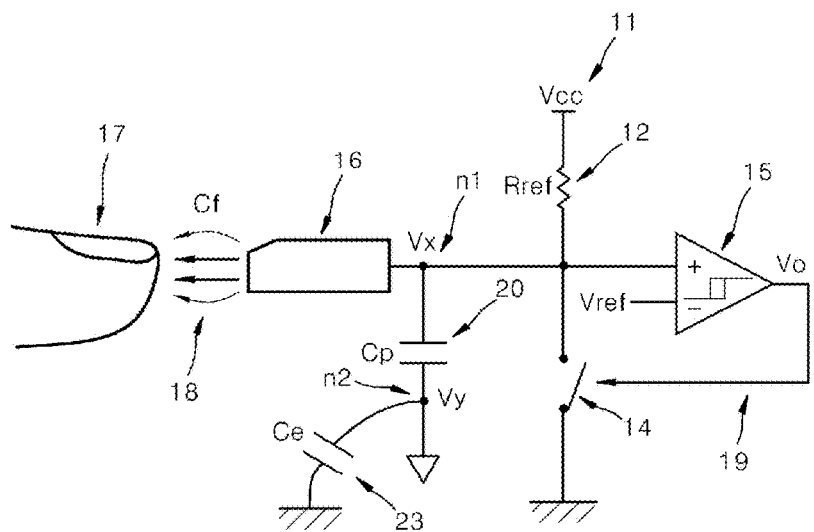
[Fig. 1b]
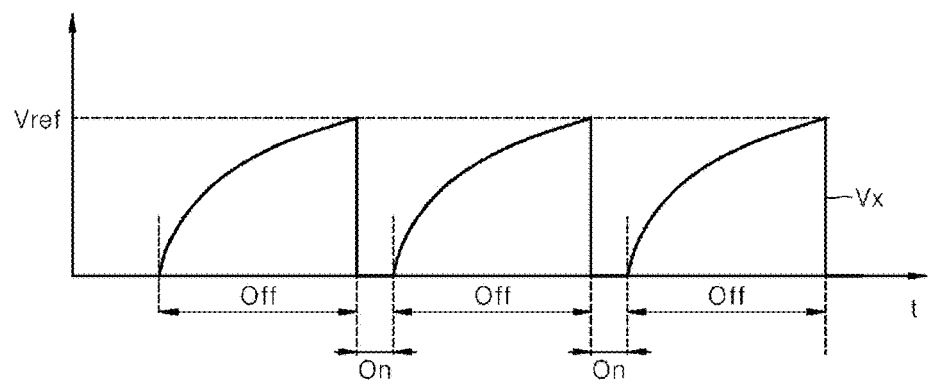
[Fig. 1c]
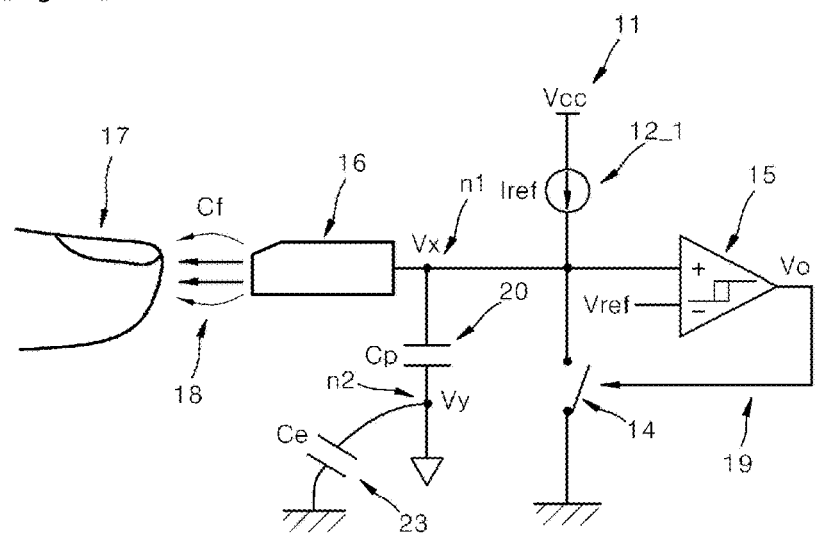

[Fig. 1d]
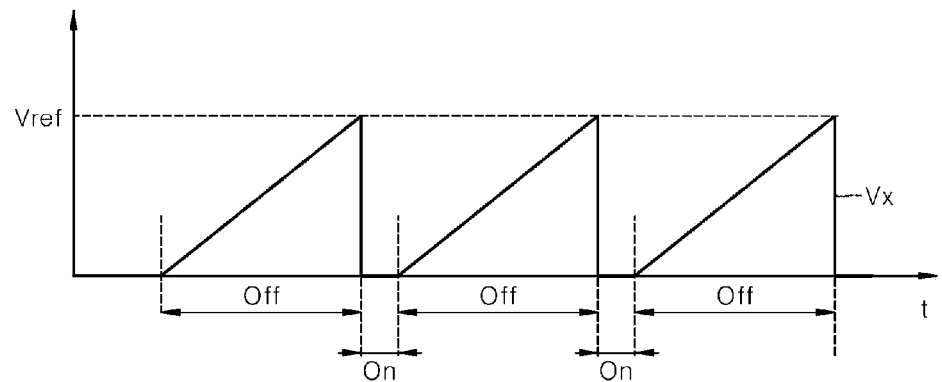
[Fig. 1e]
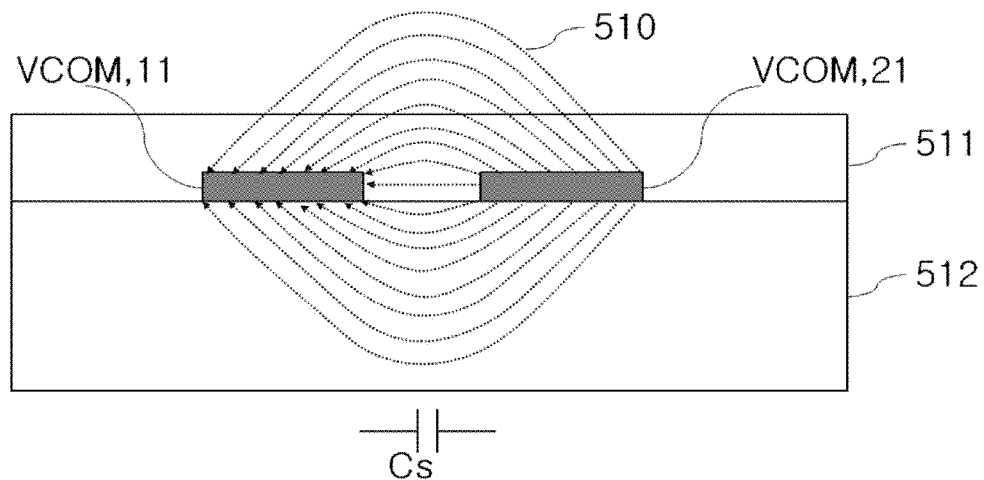
[Fig. 1f]
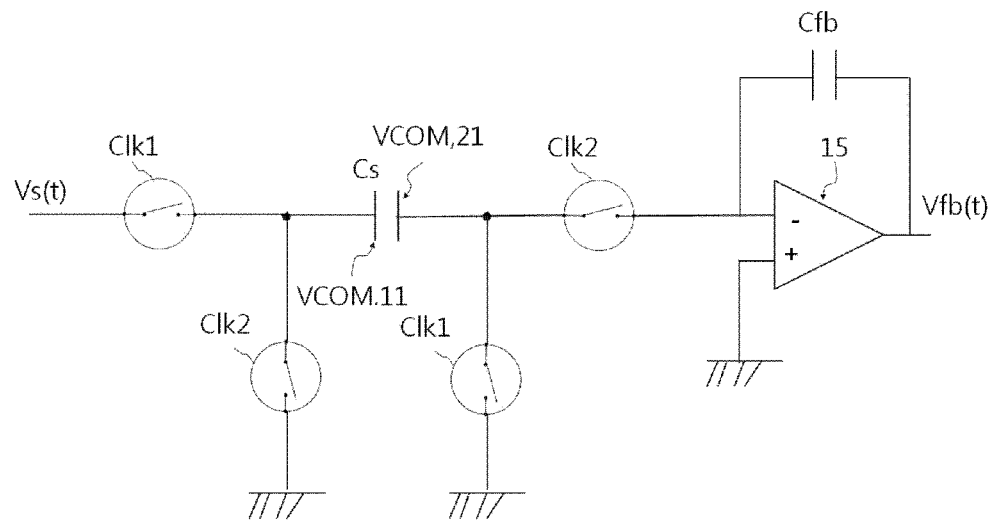

[Fig. 2a]
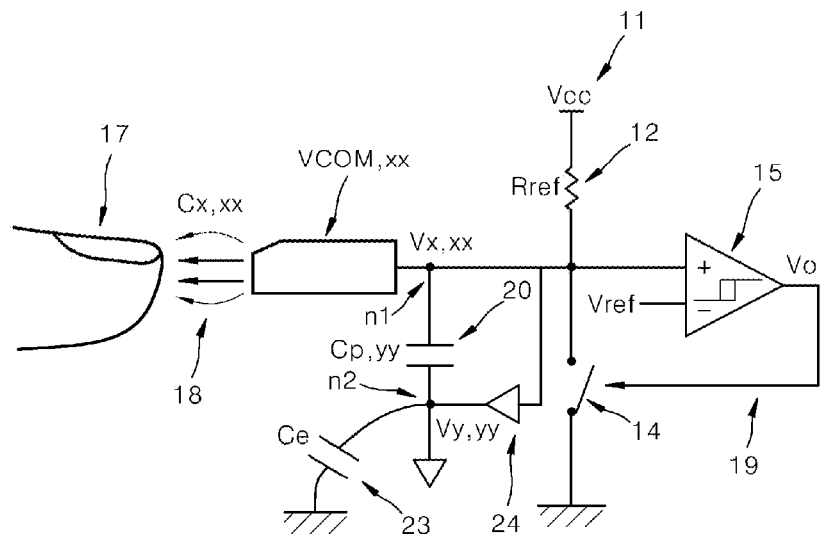
[Fig. 2b]
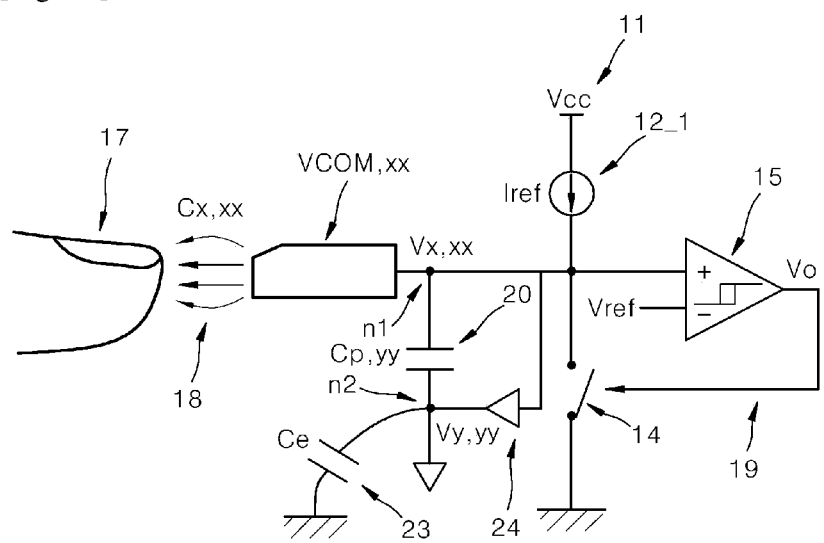

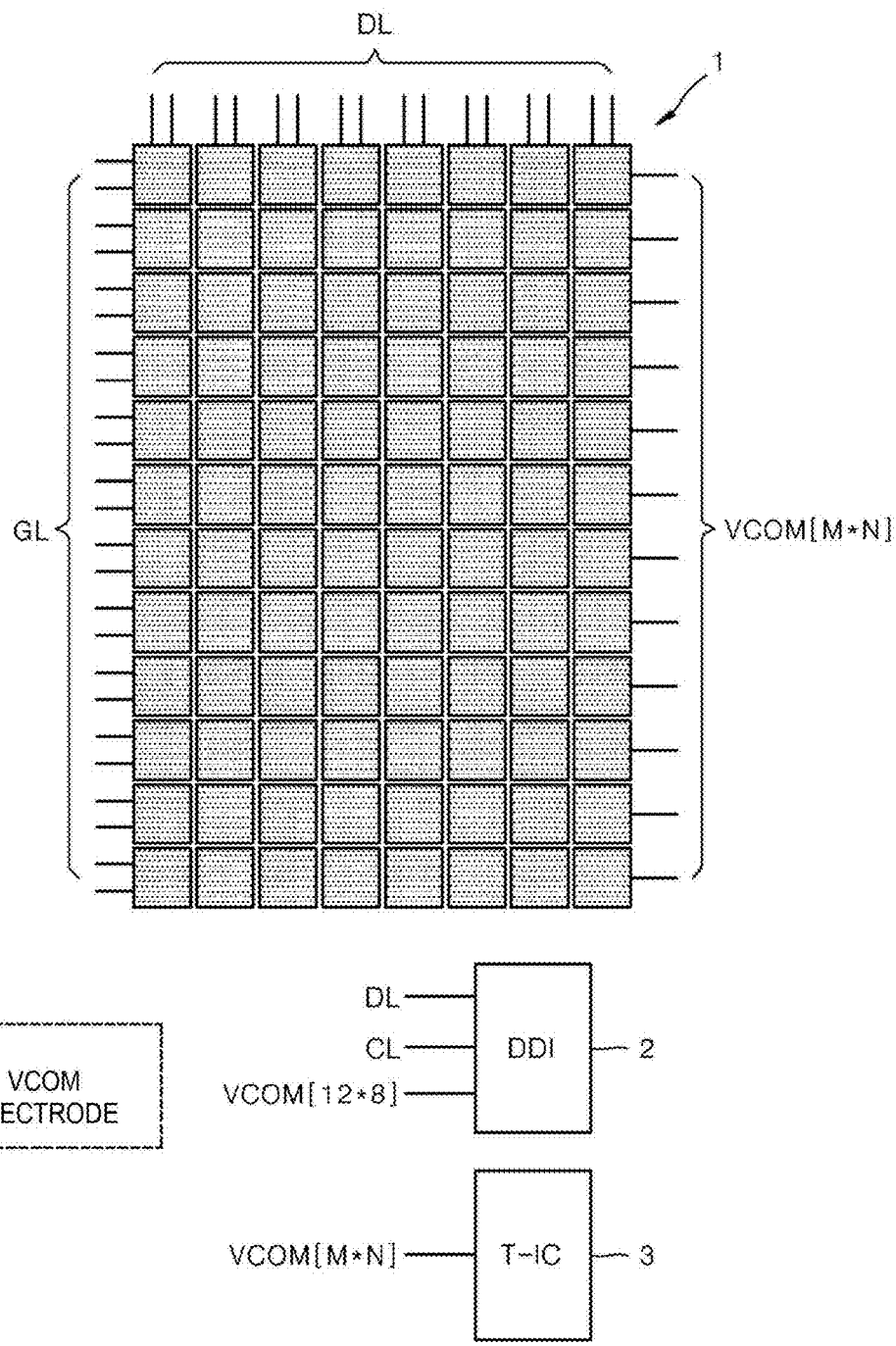
[Fig. 3]

[Fig. 4]
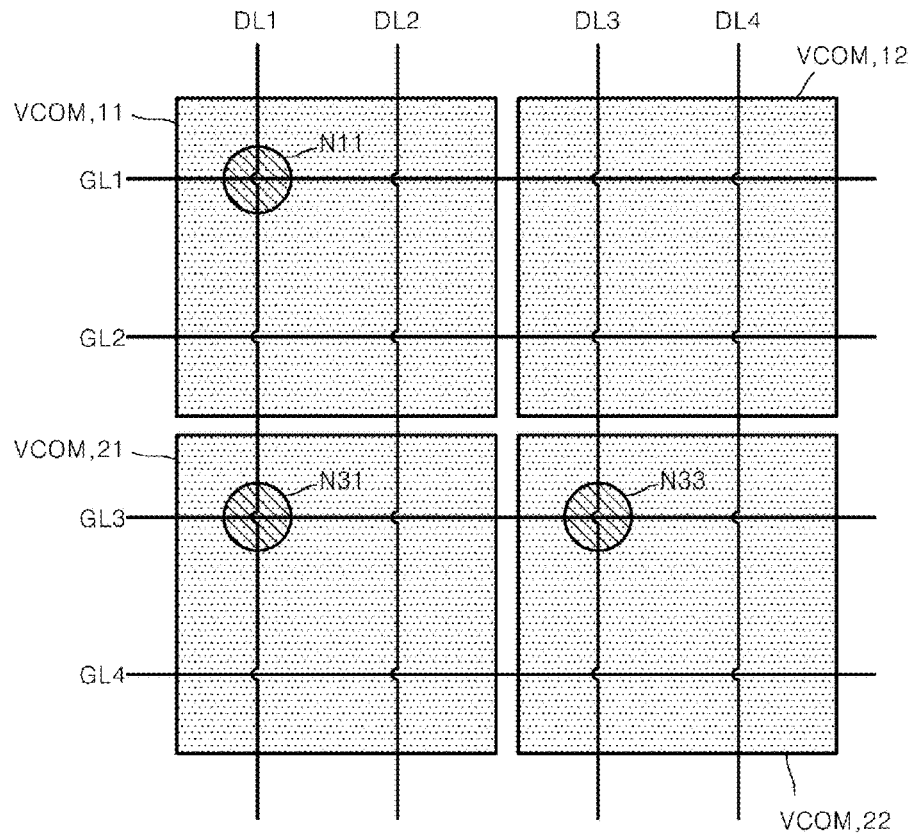
[Fig. 5a]
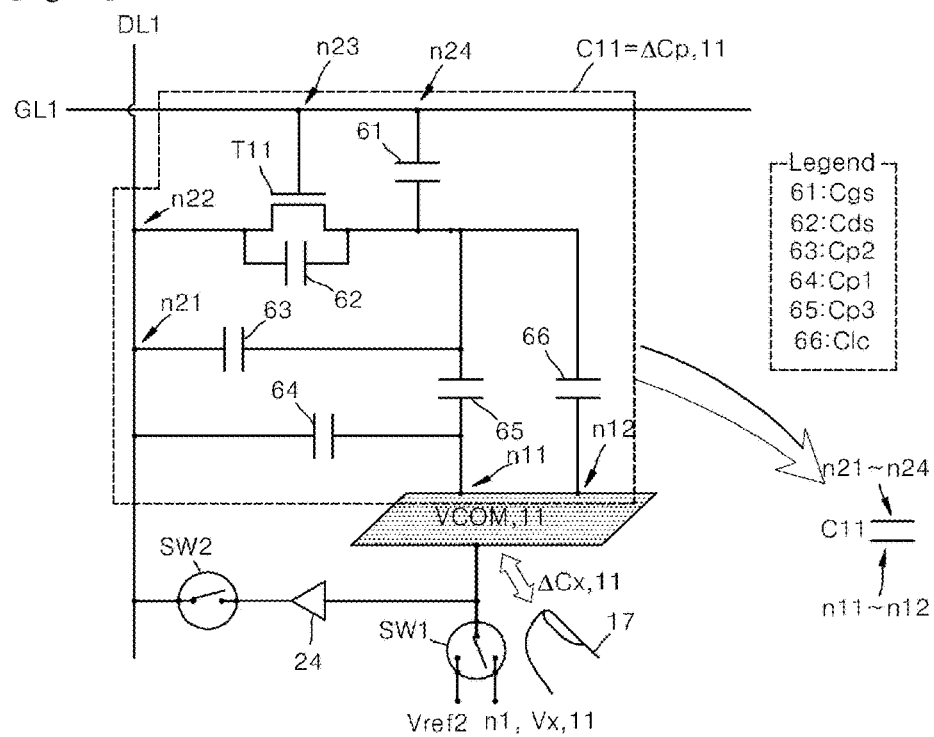

[Fig. 5b]
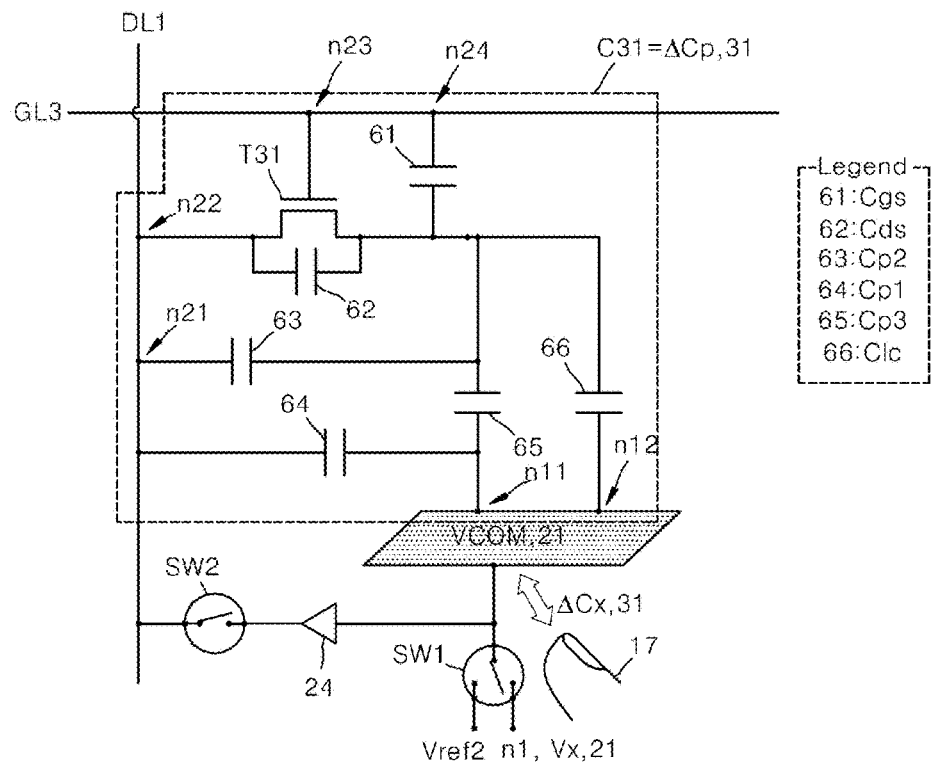
[Fig. 5c]
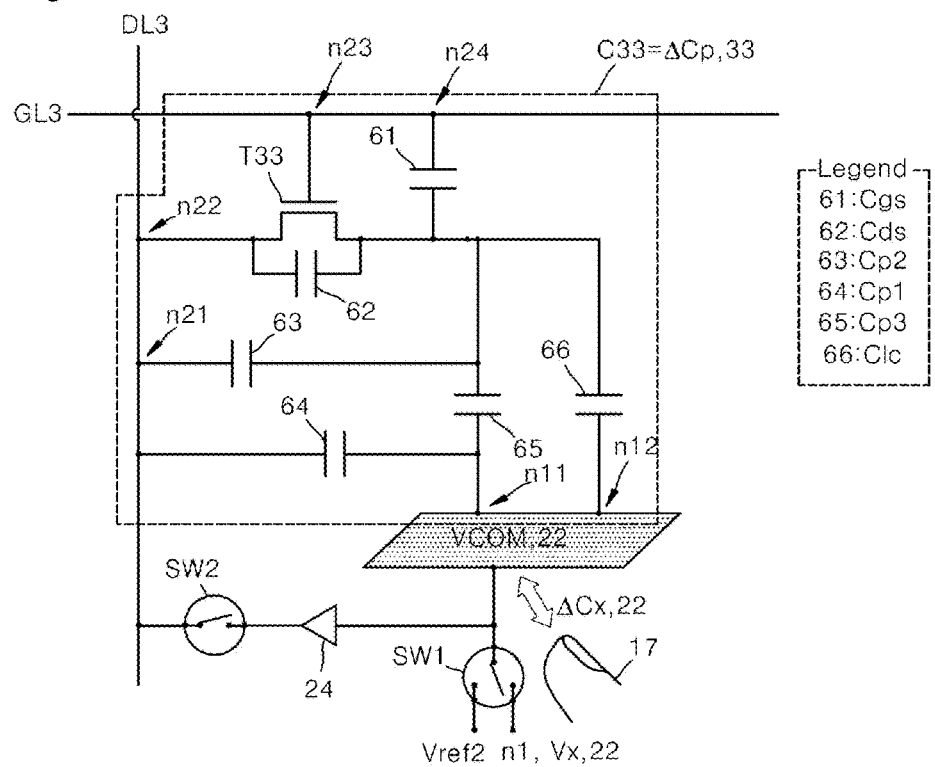

[Fig. 6a]
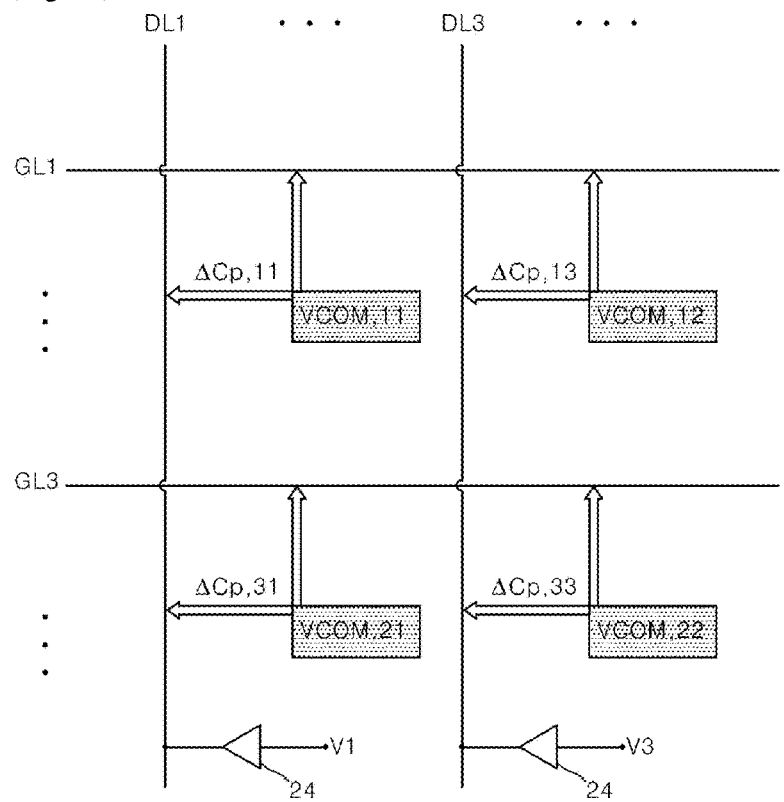
[Fig. 6b]
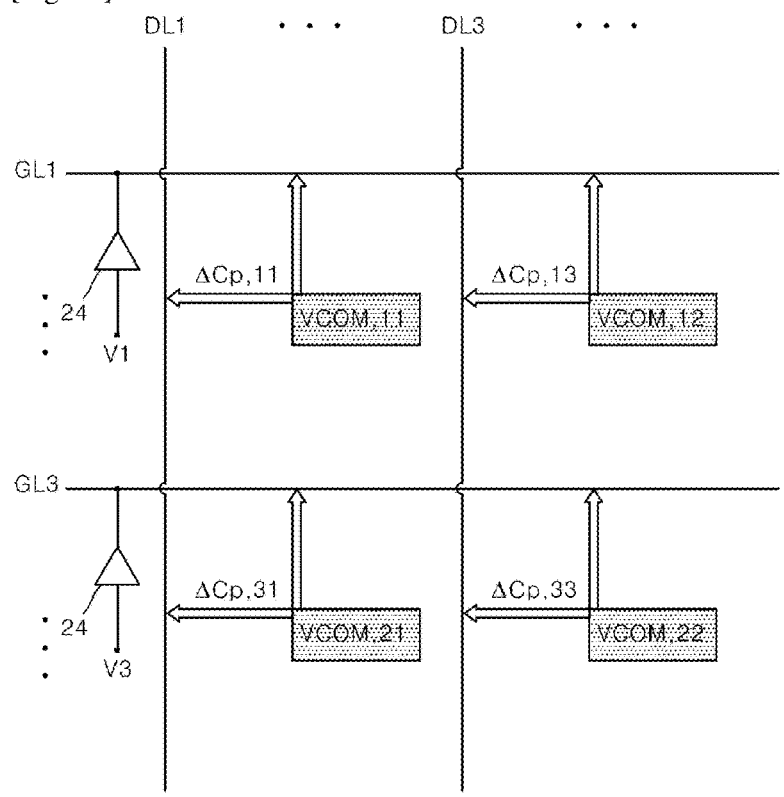

[Fig. 7a]
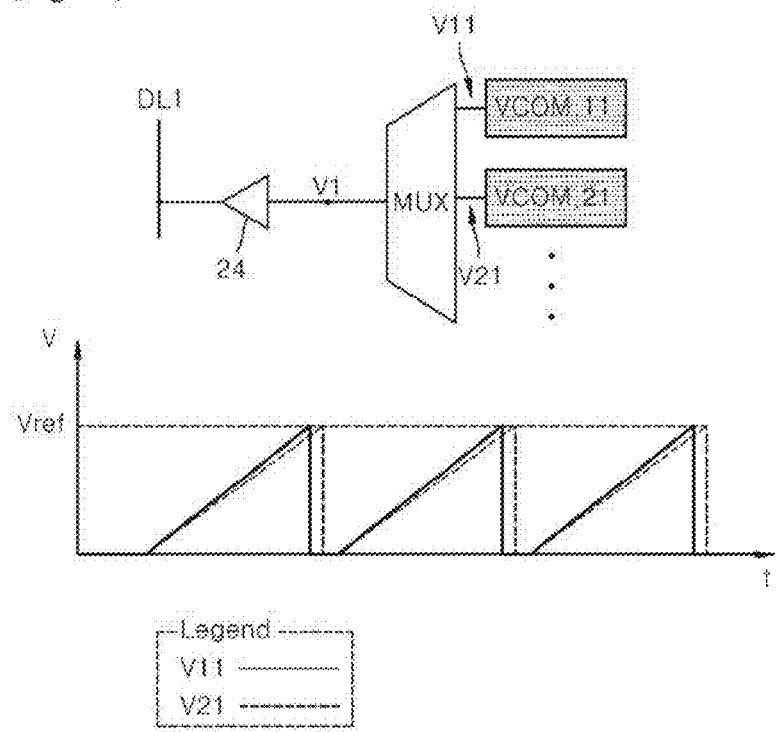
[Fig. 7b]
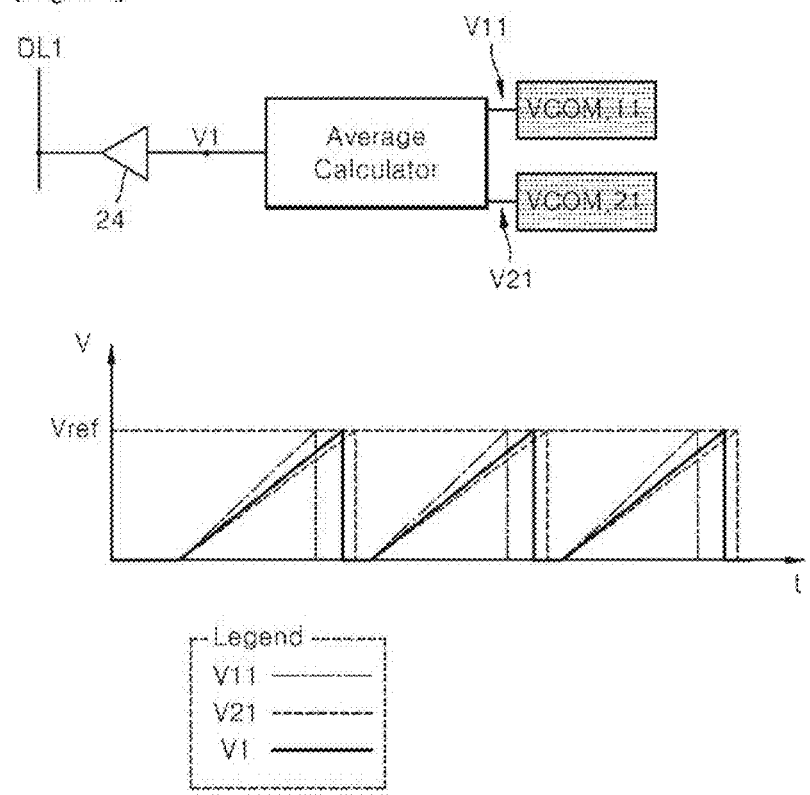

[Fig. 7c]
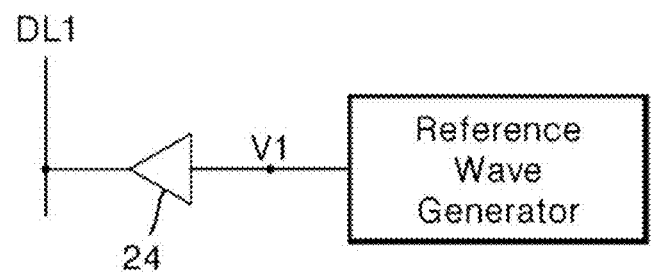
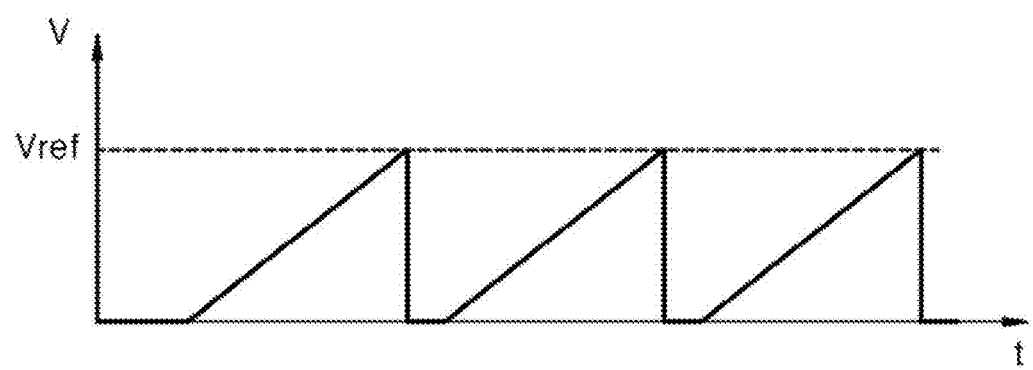

[Fig. 8]
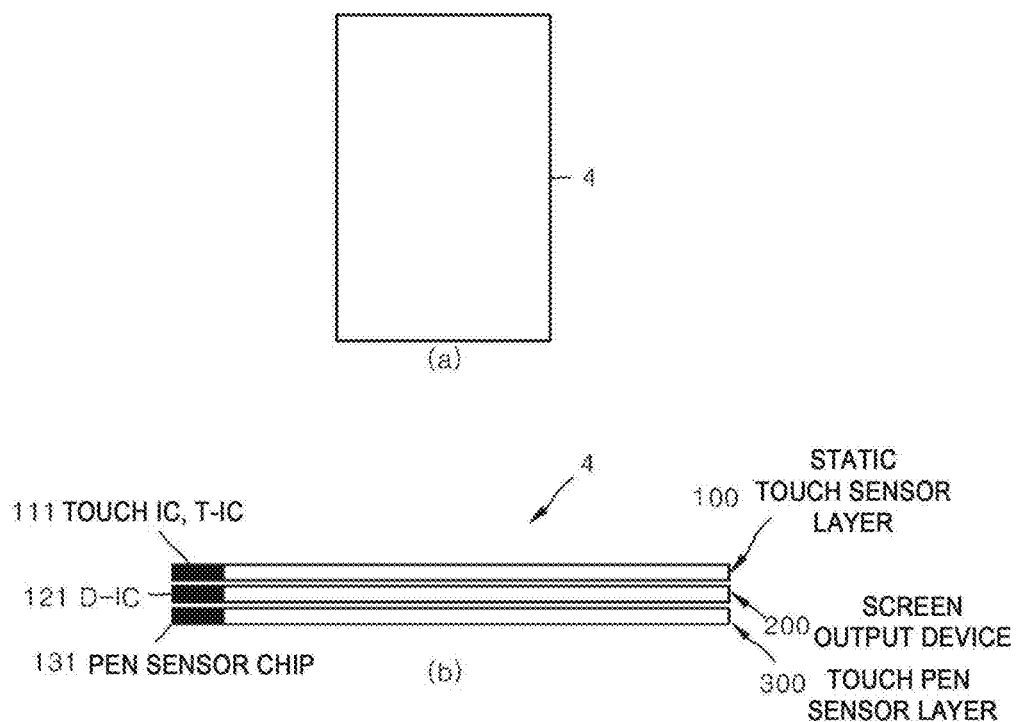

[Fig. 9]
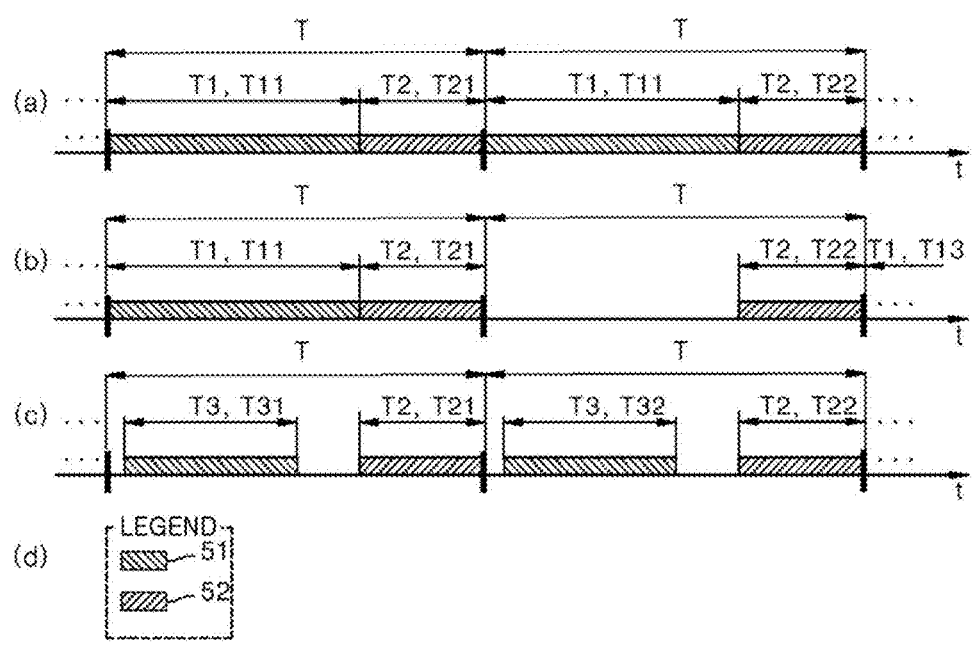

[Fig. 10]
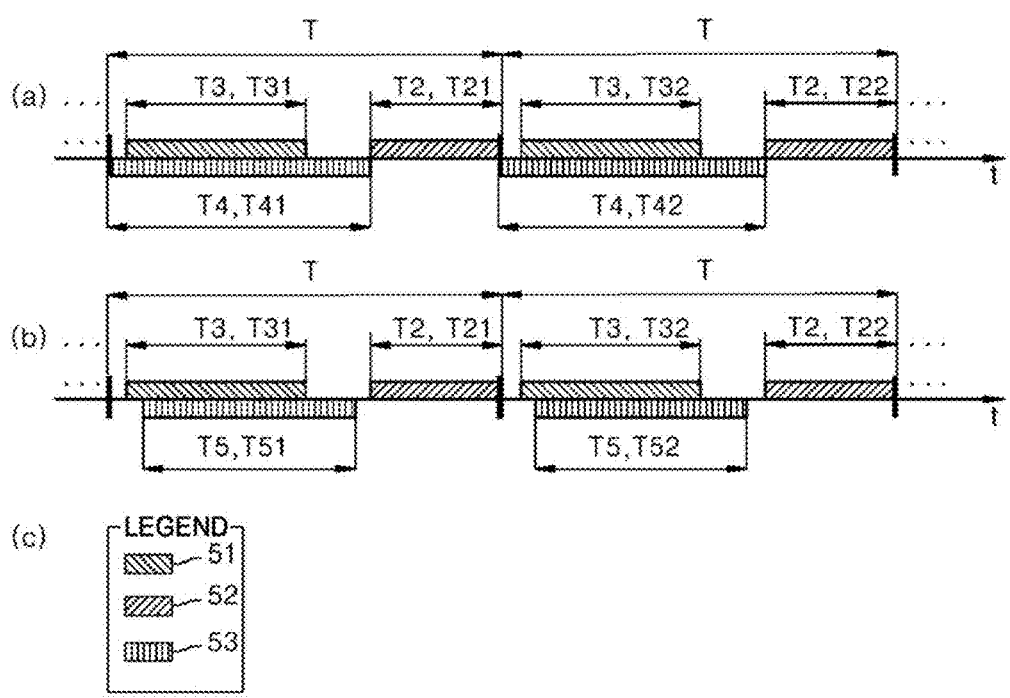

[Fig. 11]
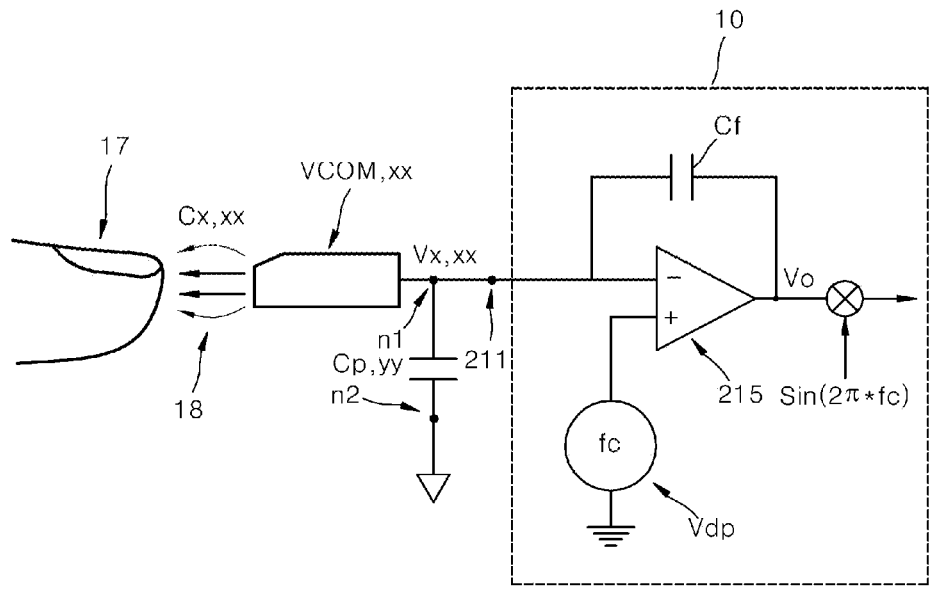
[Fig. 12]
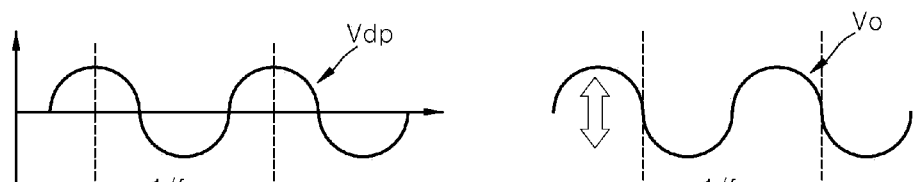
(a)
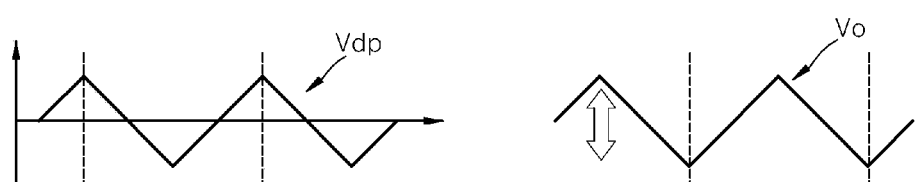
(b)
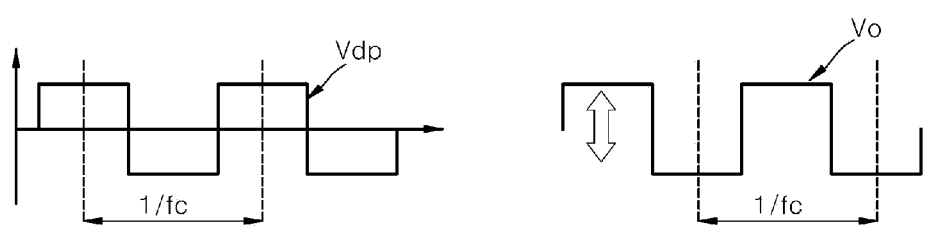
(c)

[Fig. 13]
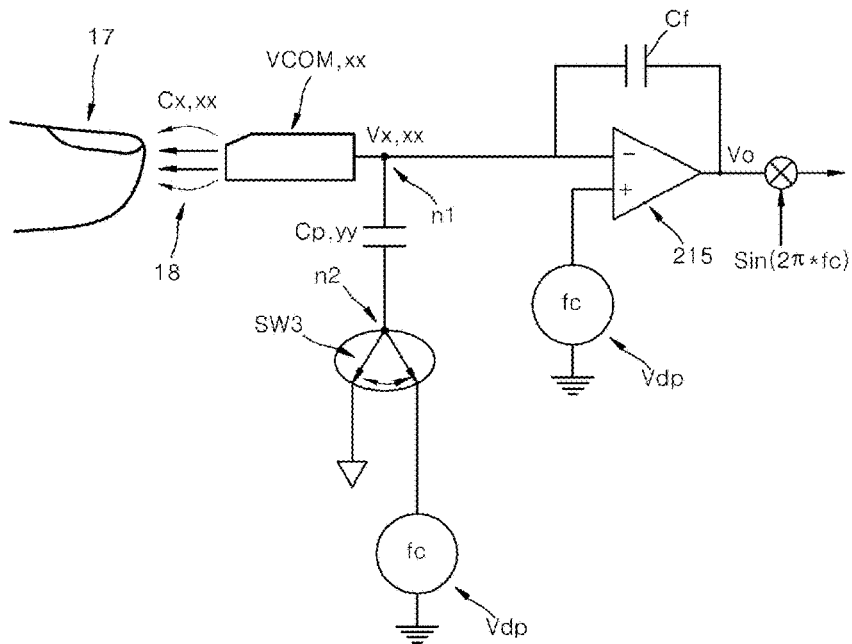
[Fig. 14a]
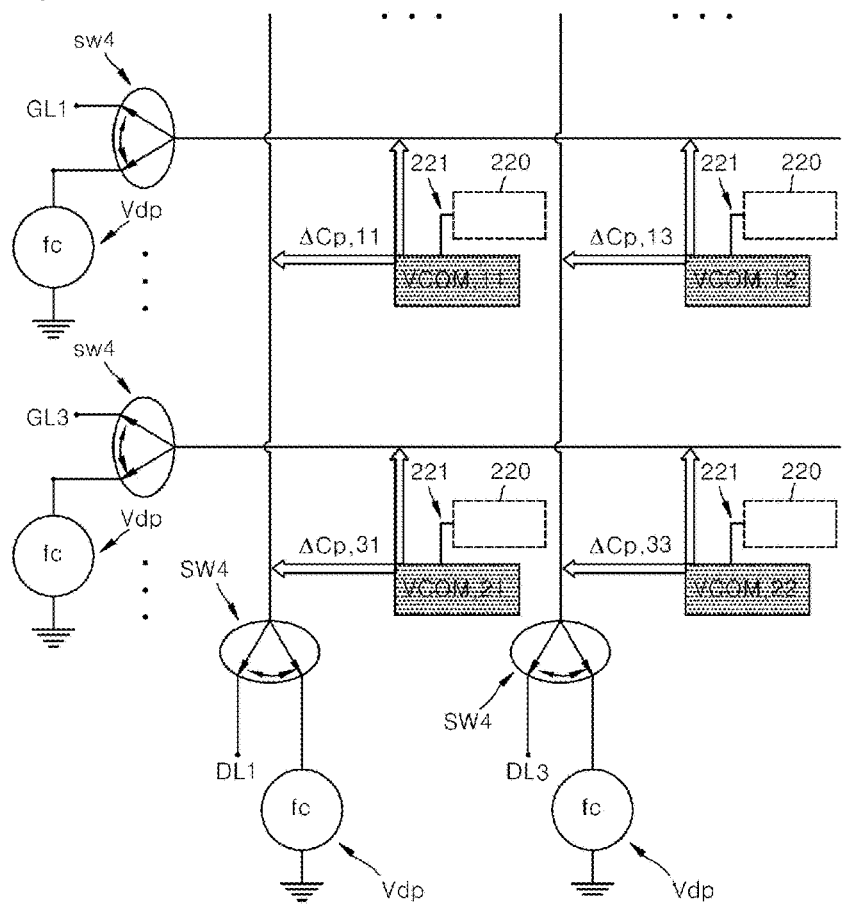

[Fig. 14b]
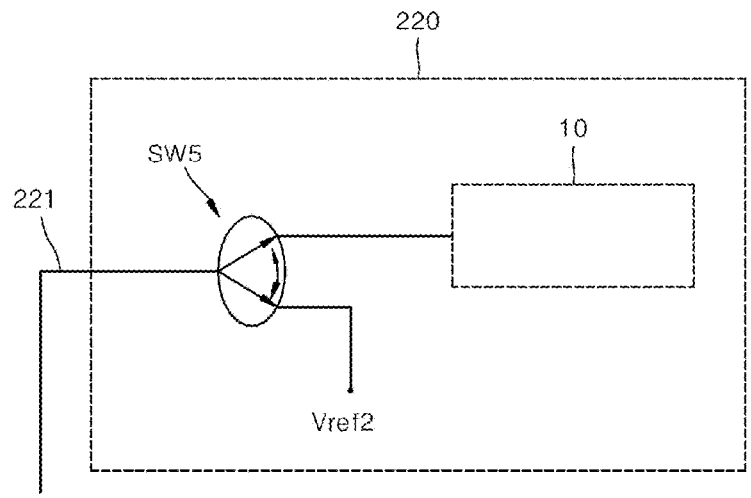
[Fig. 15]
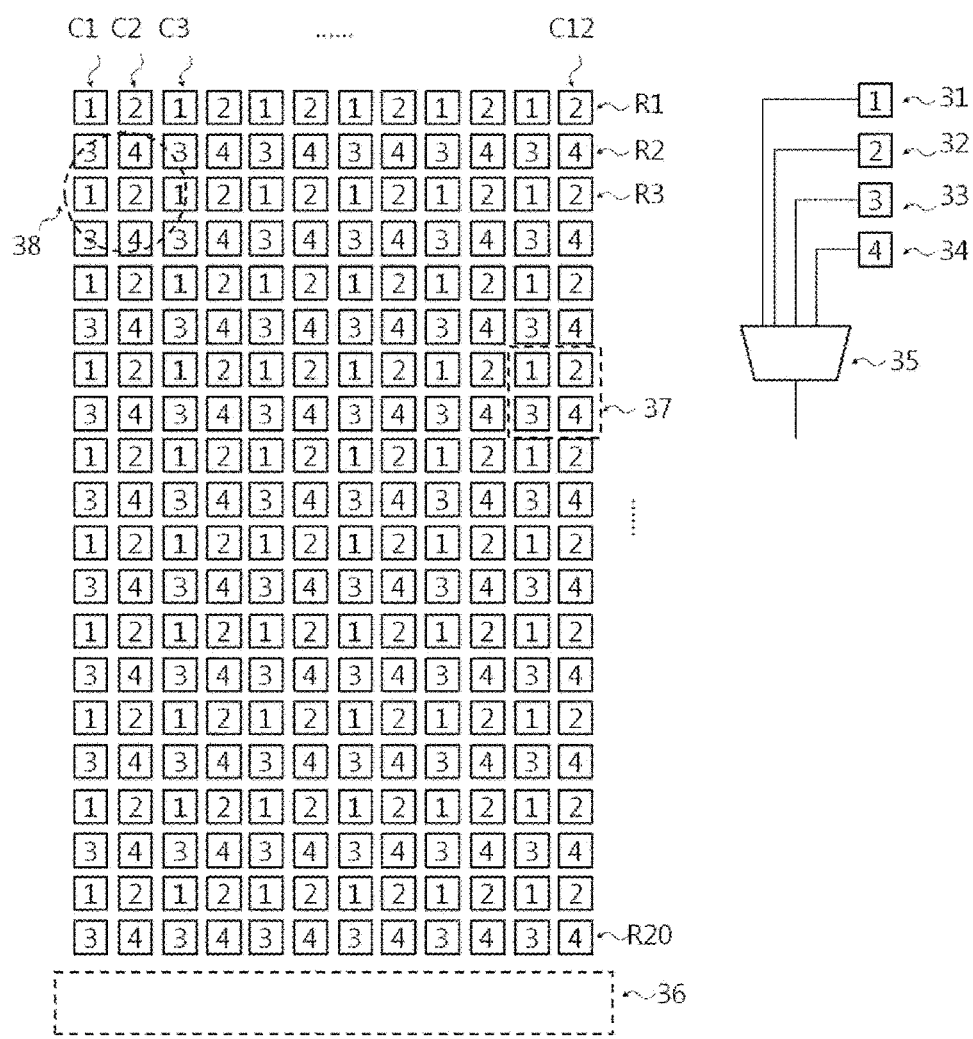

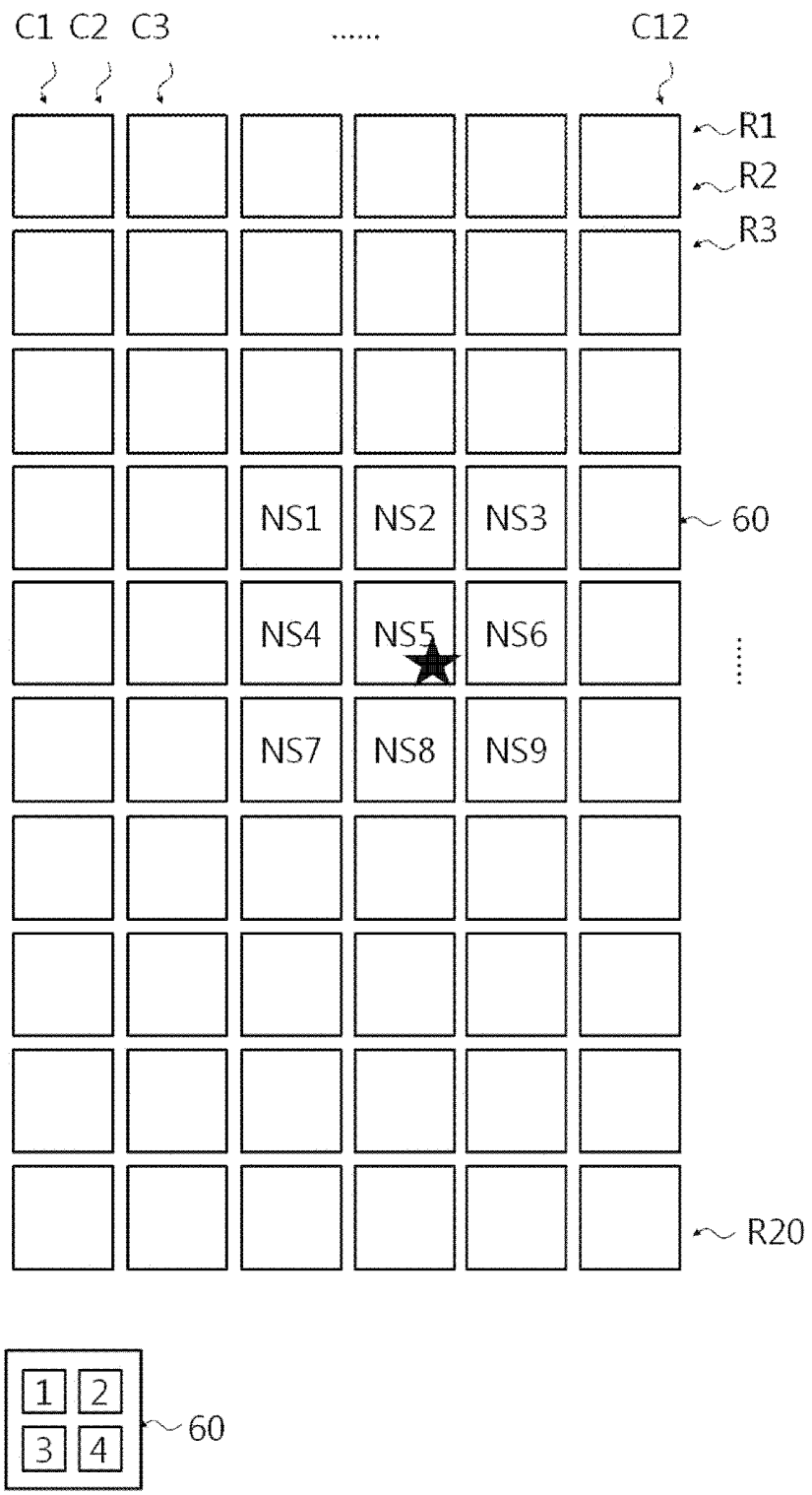
[Fig. 16a]

[Fig. 16b]
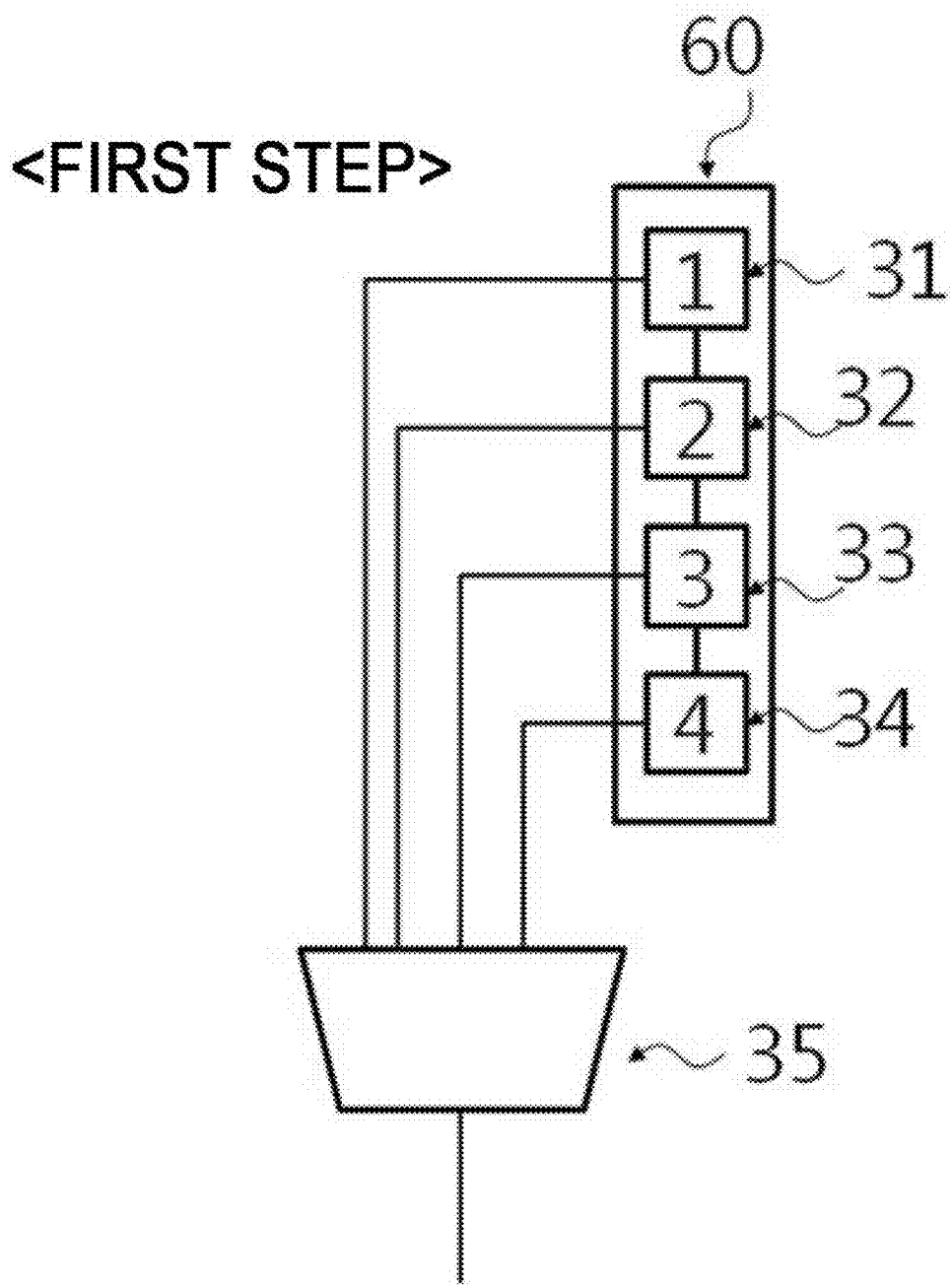

[Fig. 16c]
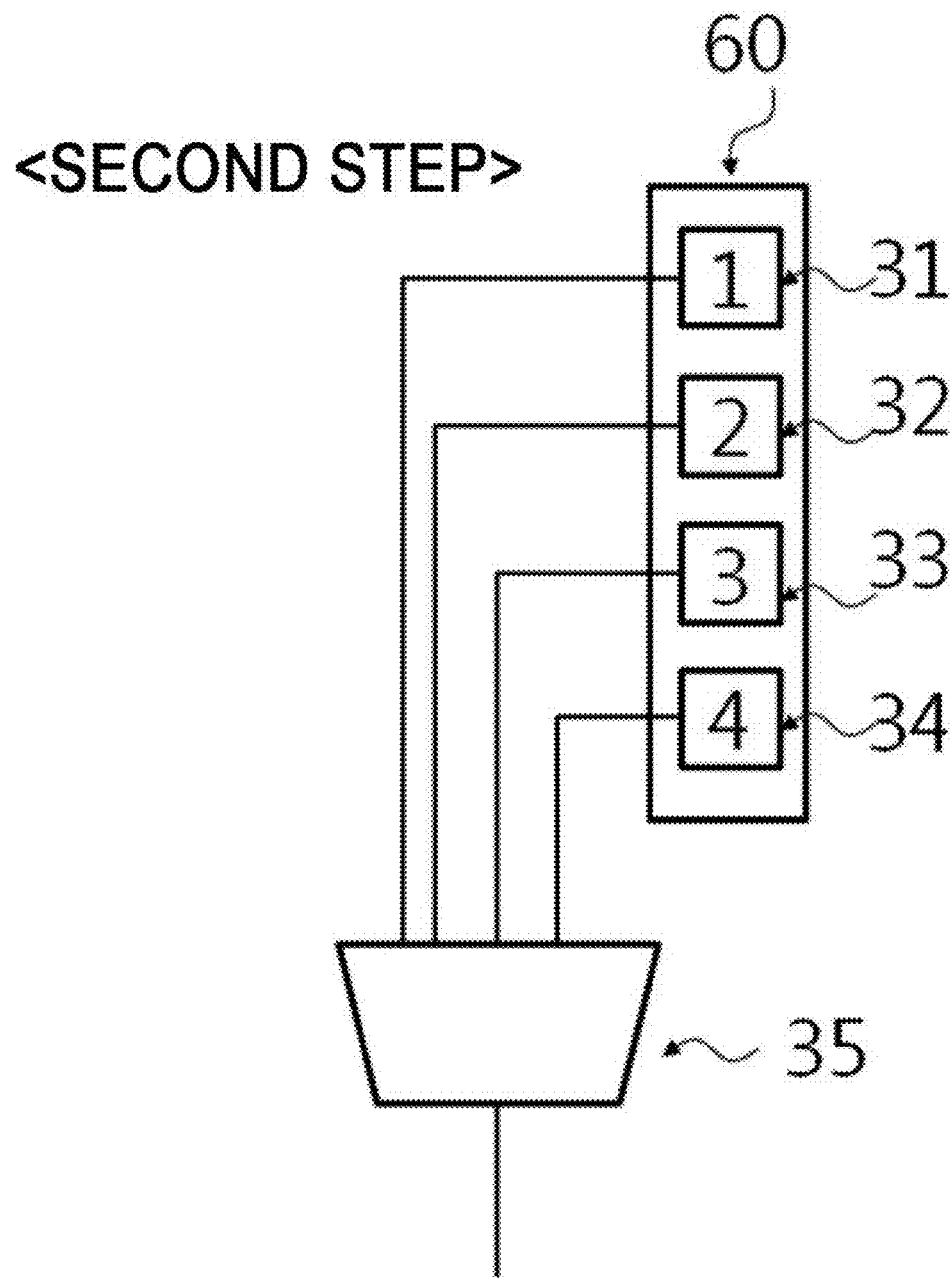

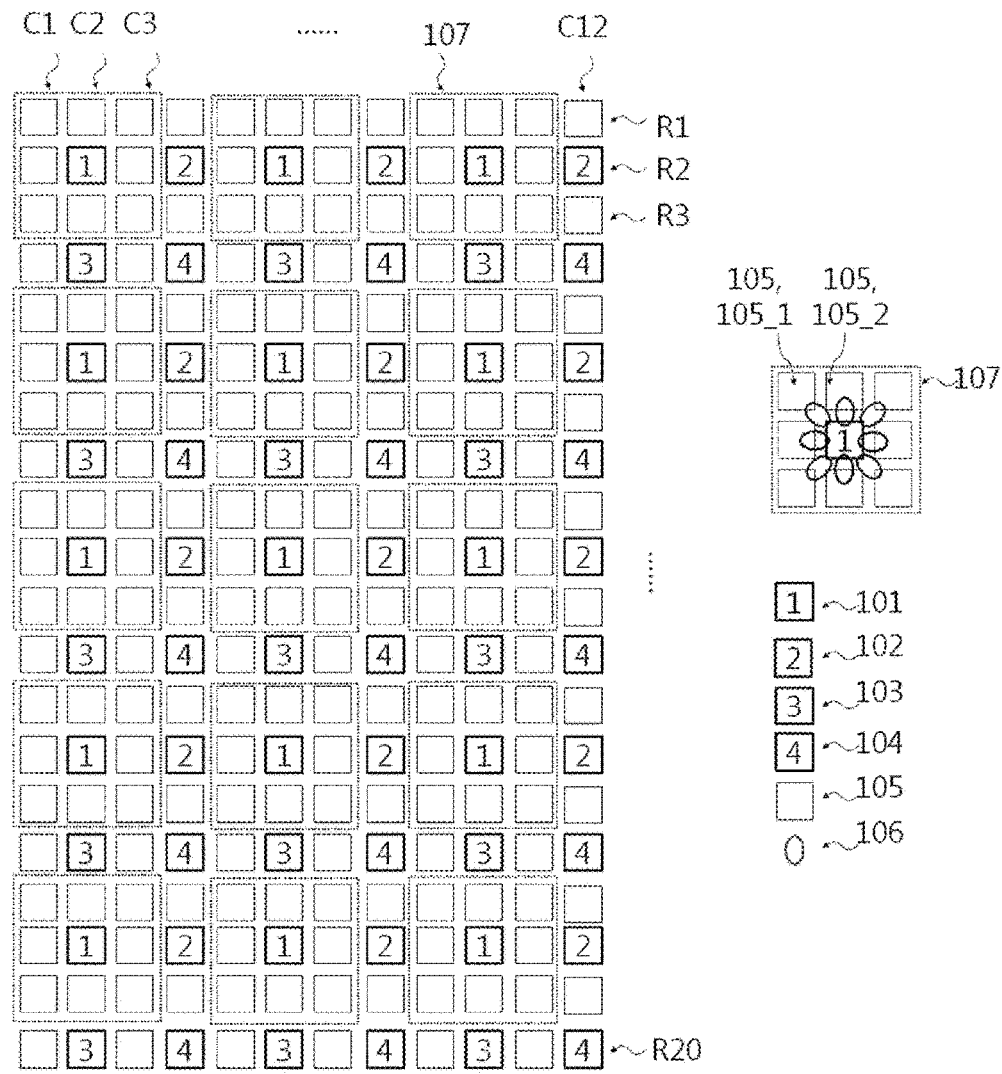
[Fig. 17a]

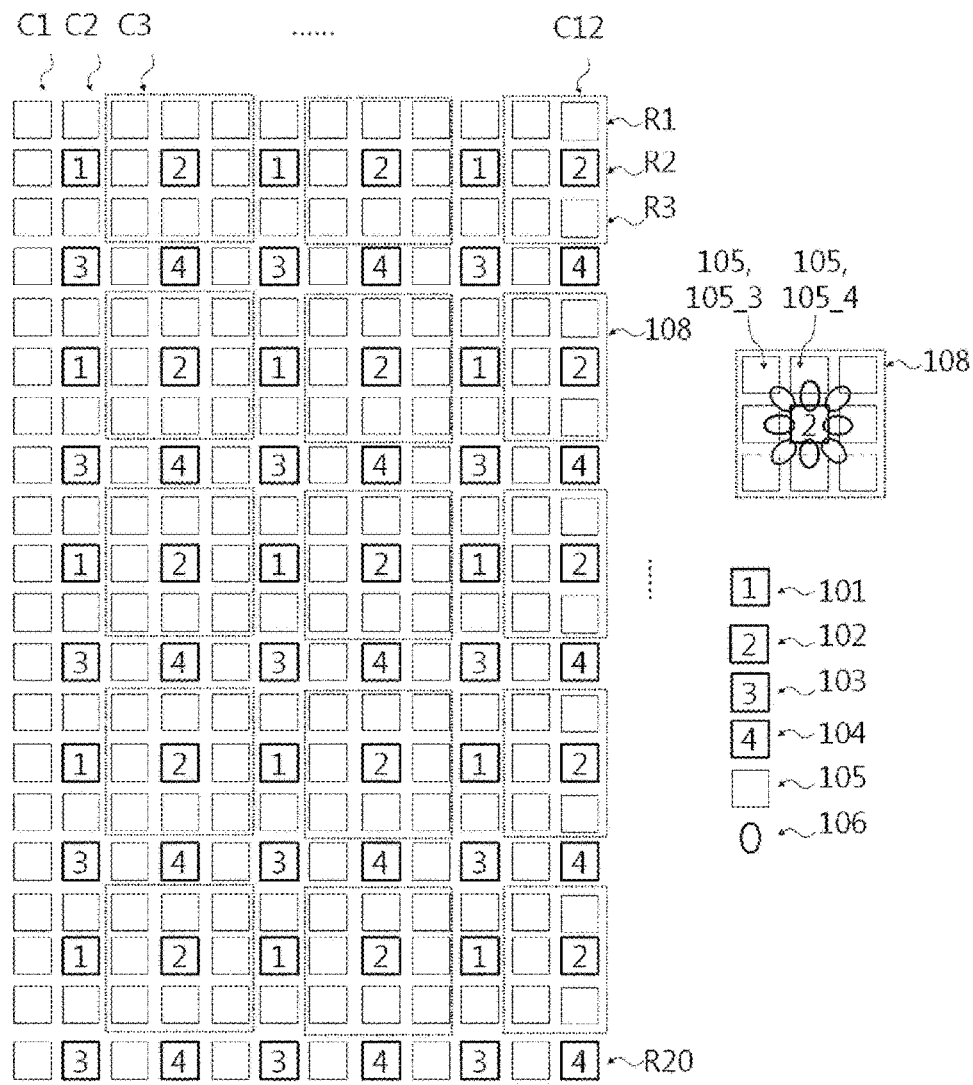
[Fig. 17b]

[Fig. 17c]
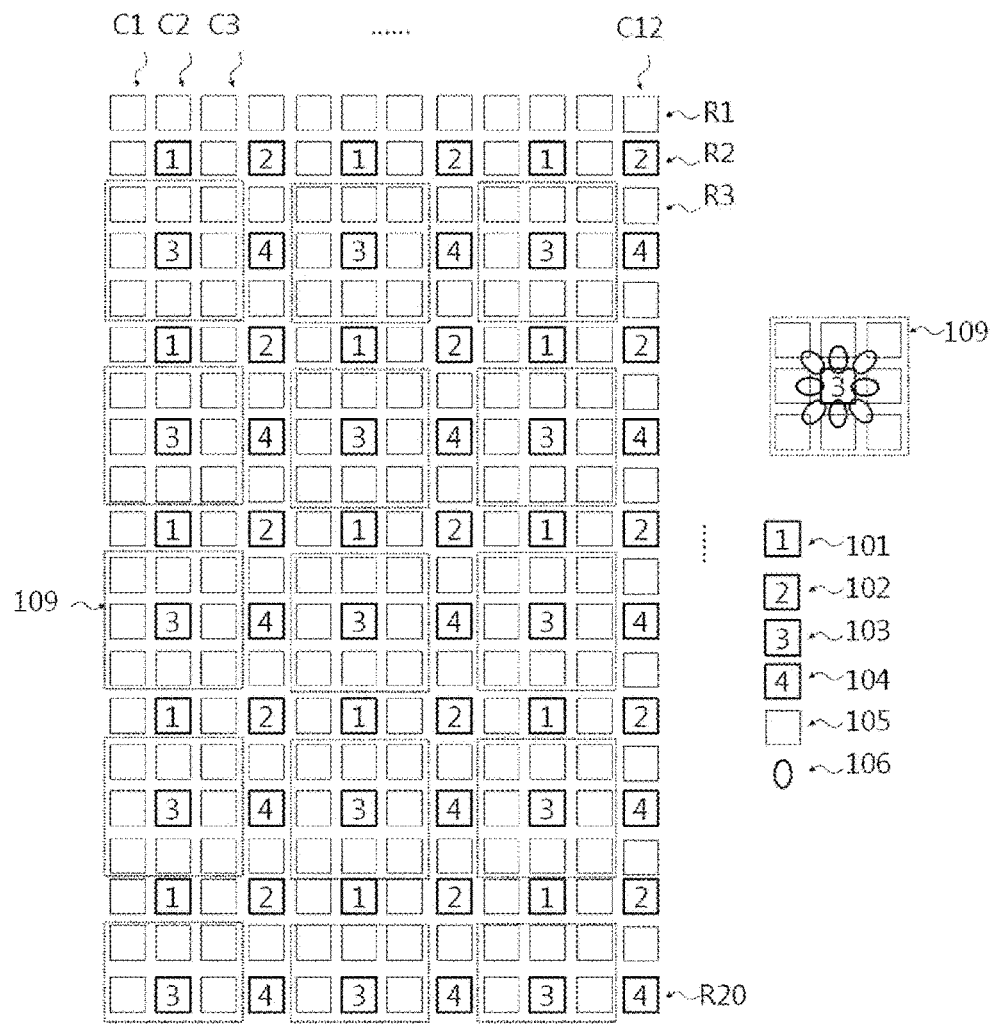

[Fig. 17d]
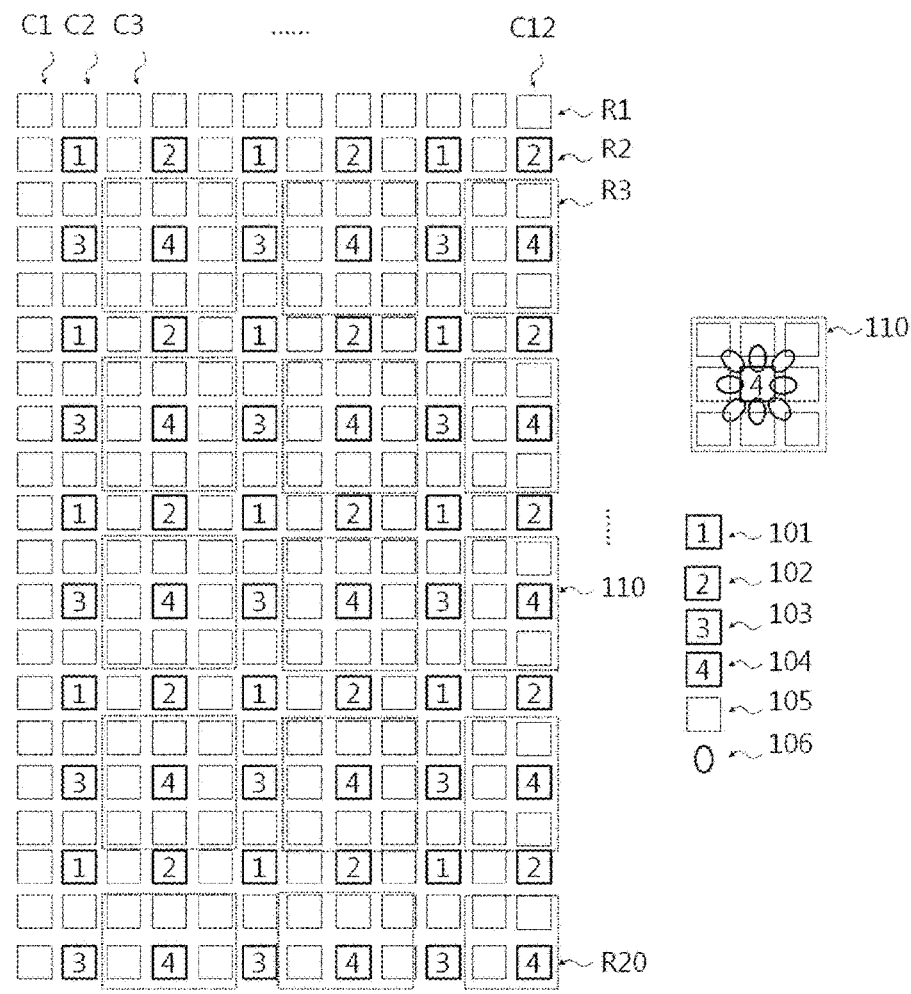
[Fig. 17e]
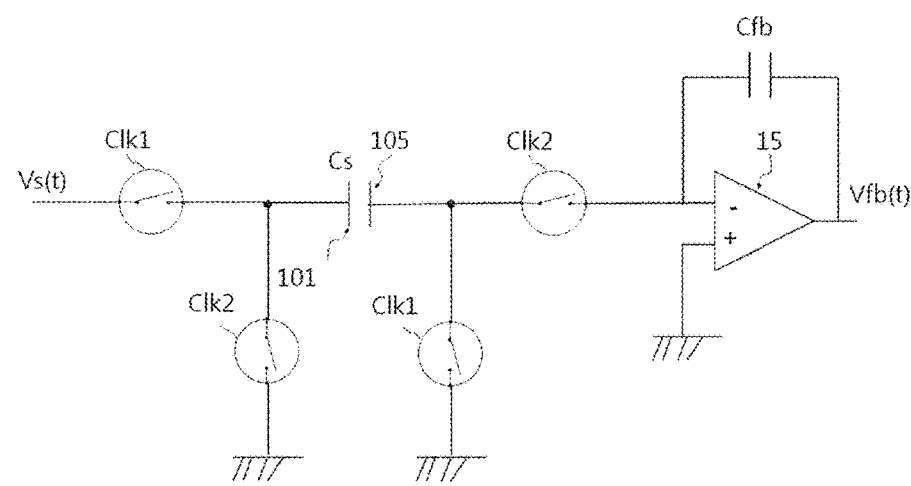

[Fig. 17f]
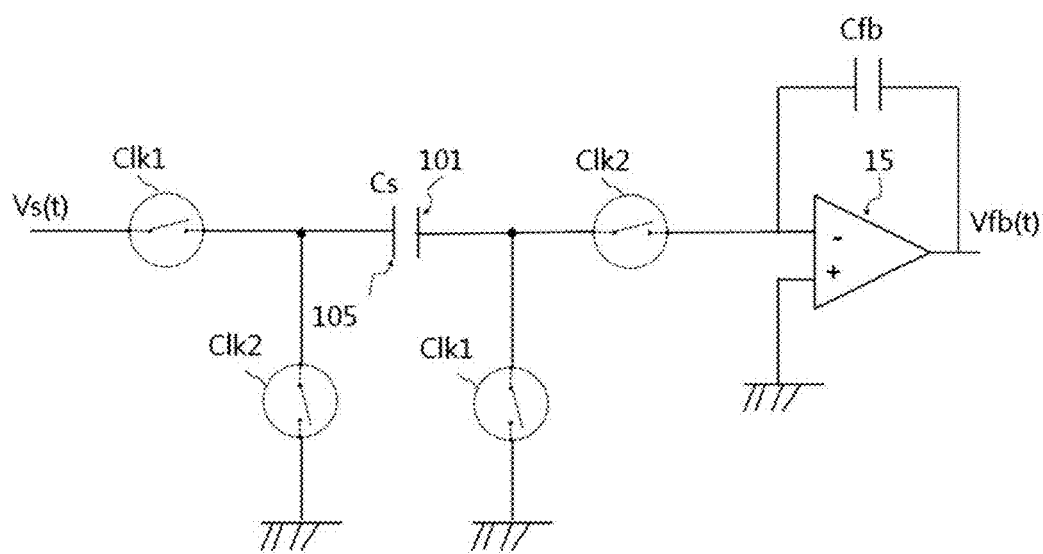

[Fig. 18a]
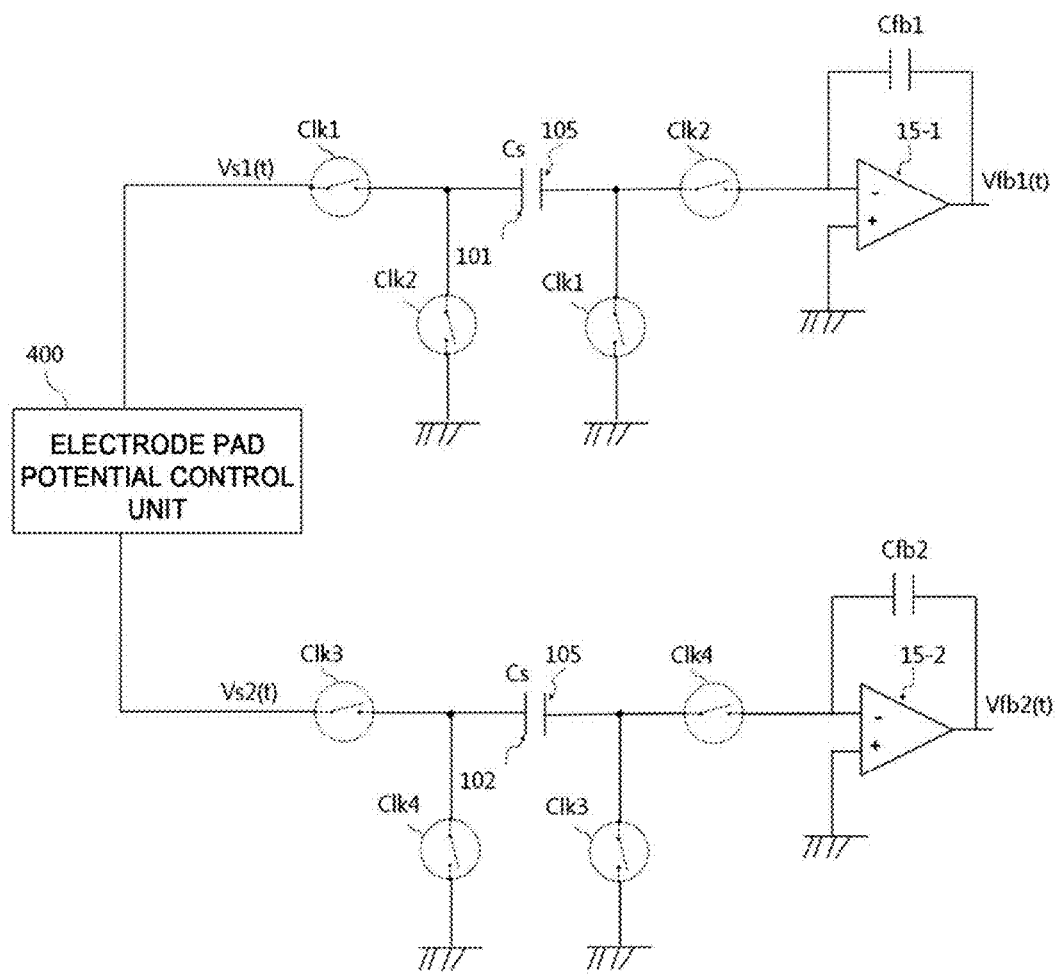

[Fig. 18b]
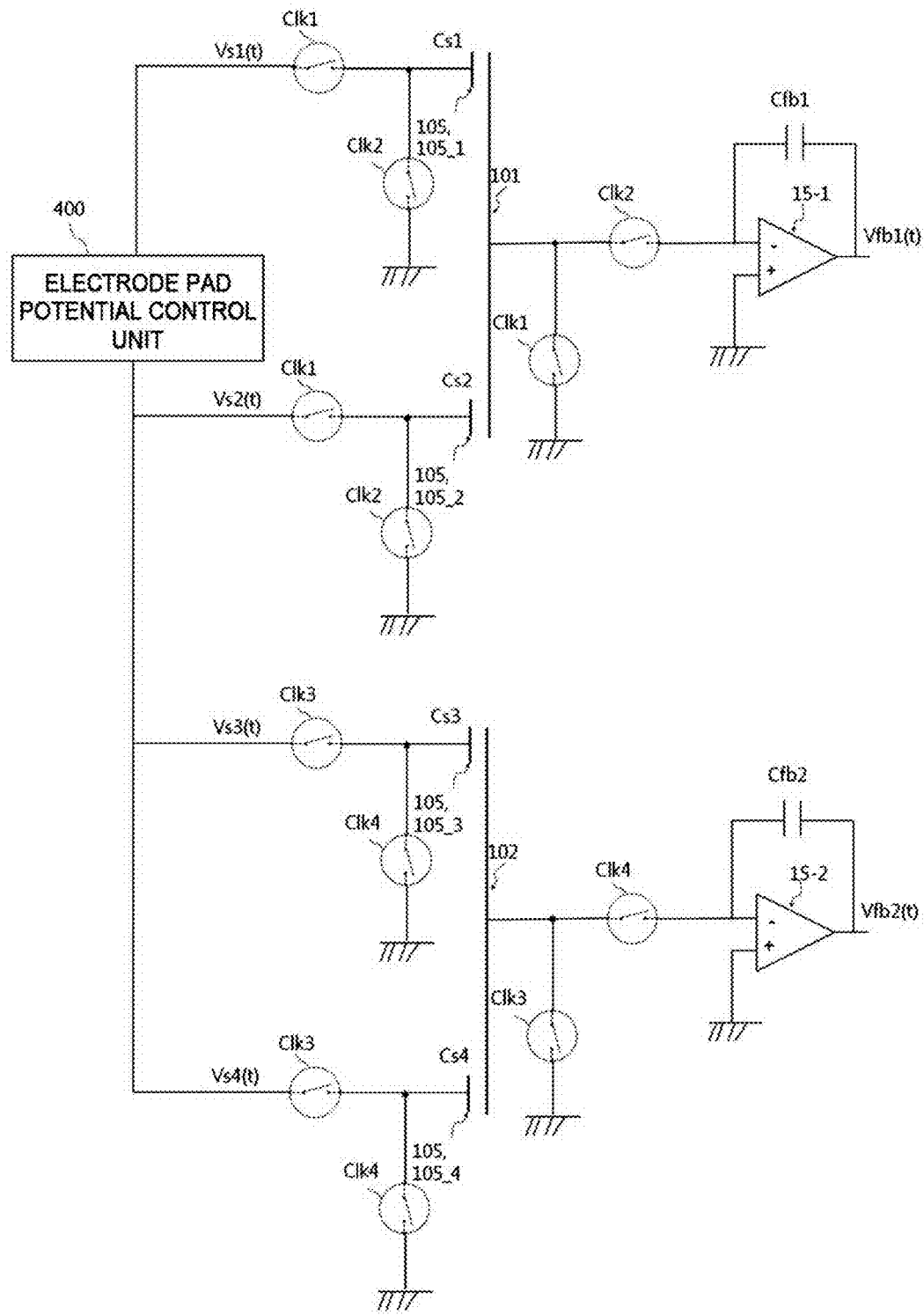

[Fig. 19]
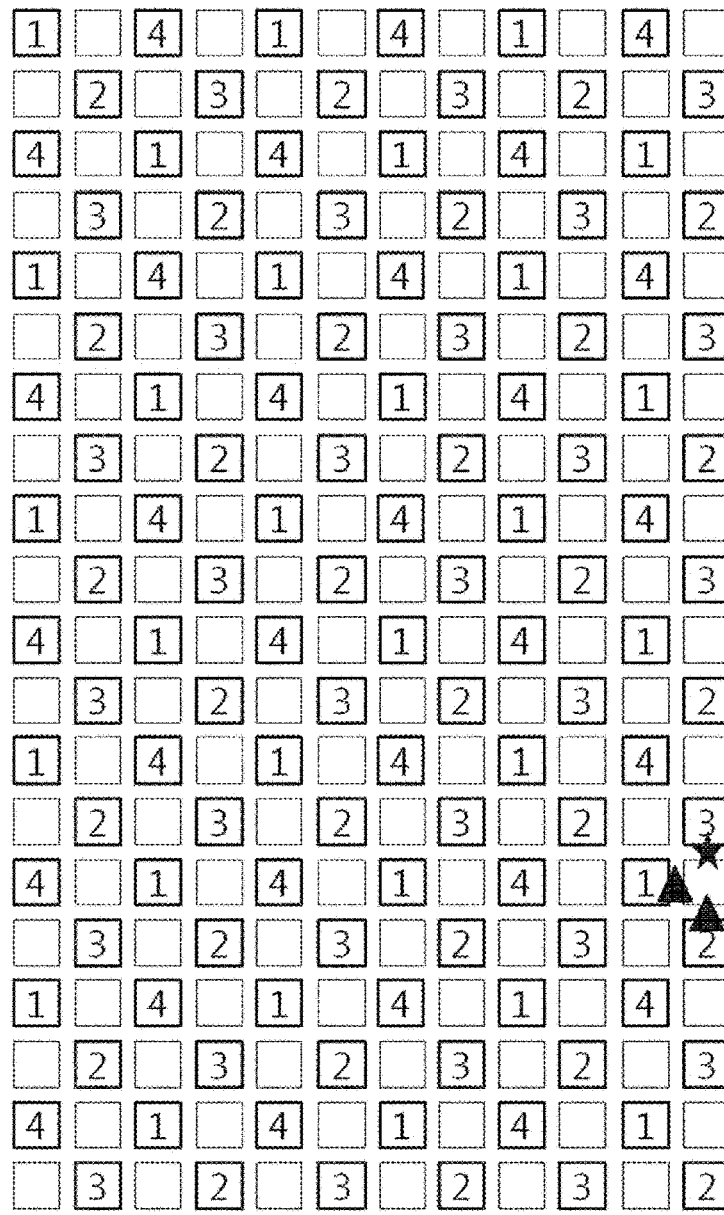
[Fig. 20a]
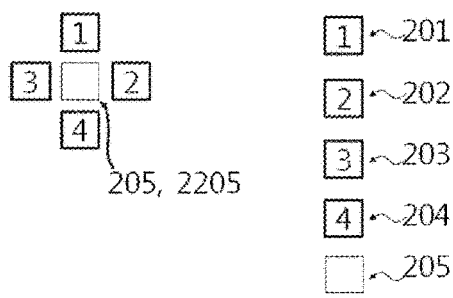

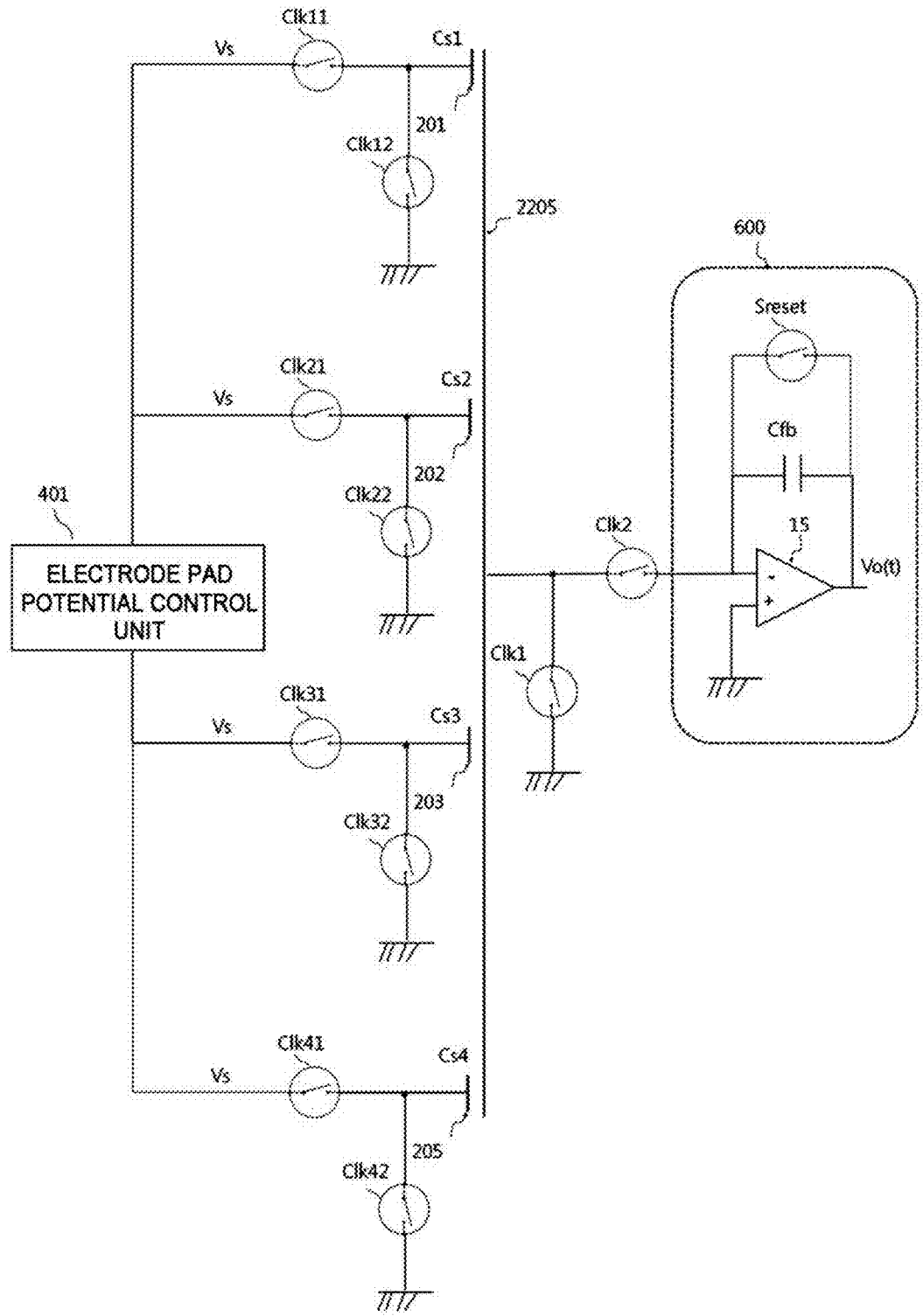
[Fig. 20b]

[Fig. 20c]
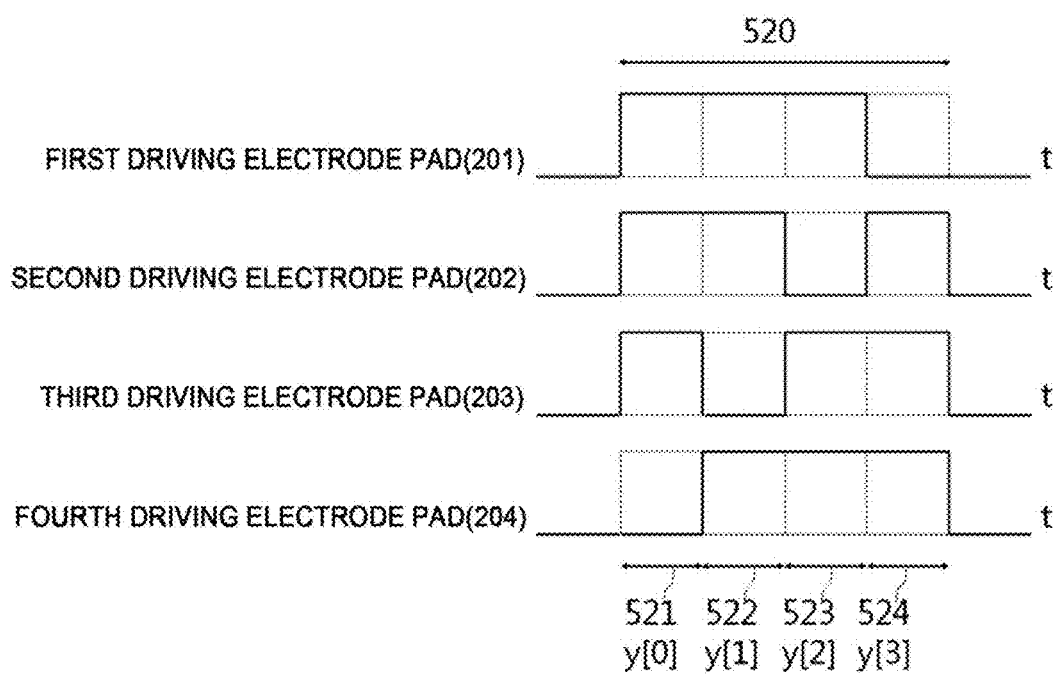

[Fig. 20d]
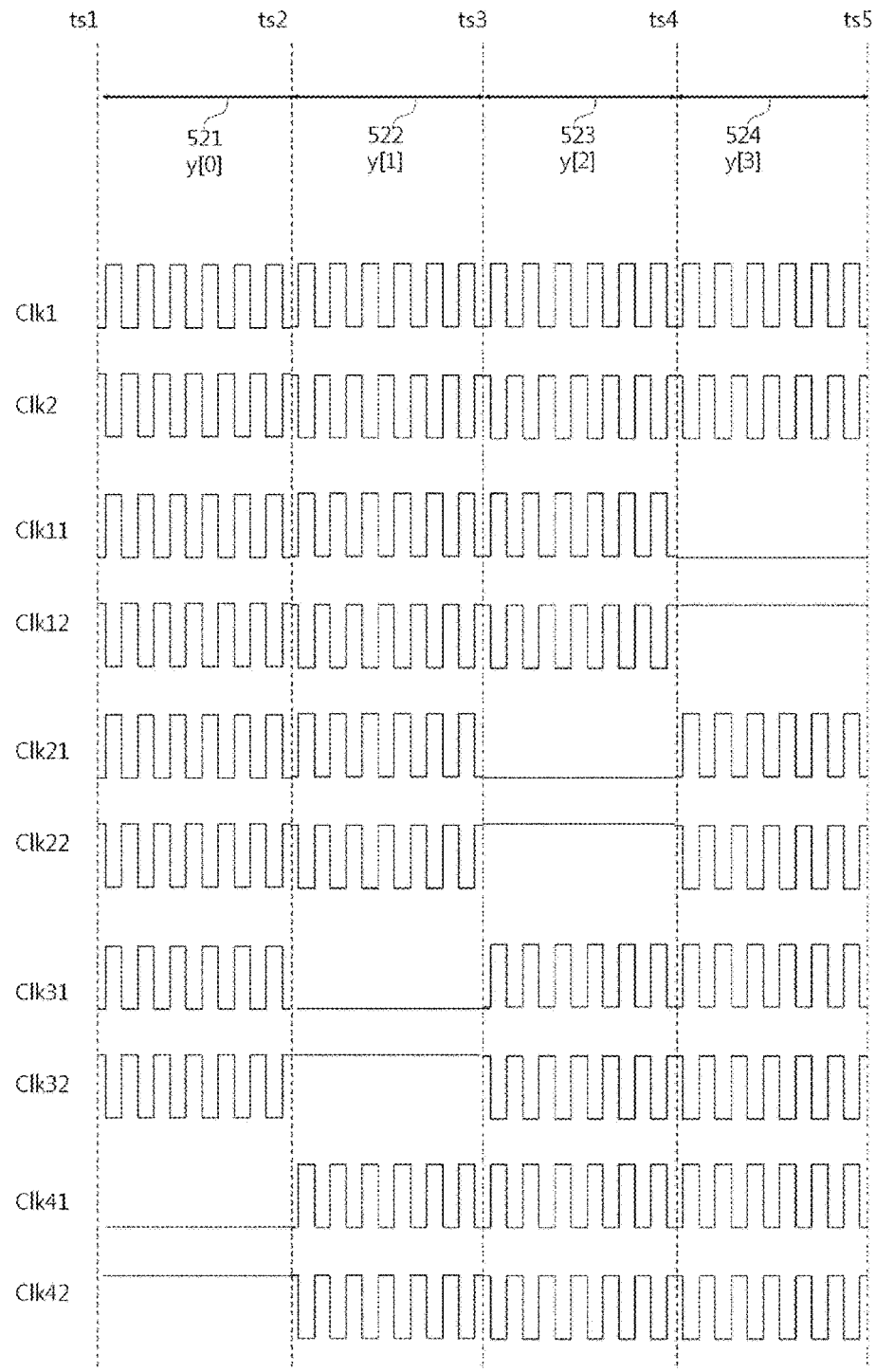

[Fig. 21a]

|  | C1 | C2 | C3 |  |  |  |  |  |  |  | C12 |  |
|---|---|---|---|---|---|---|---|---|---|---|---|---|
|  | 1 | 2 | 1 | 4 | 1 | 6 | 1 | 8 | 1 | A | 1 | C | ~R1
|  | 2 | 1 | 4 | 1 | 6 | 1 | 8 | 1 | A | 1 | C | 1 | ~R2
|  | 3 | 2 | 3 | 4 | 3 | 6 | 3 | 8 | 3 | A | 3 | C | ~R3
|  | 2 | 3 | 4 | 3 | 6 | 3 | 8 | 3 | A | 3 | C | 3 |
|  | 5 | 2 | 5 | 4 | 5 | 6 | 5 | 8 | 5 | A | 5 | C |
|  | 2 | 5 | 4 | 5 | 6 | 5 | 8 | 5 | A | 5 | C | 5 |
|  | 7 | 2 | 7 | 4 | 7 | 6 | 7 | 8 | 7 | A | 7 | C |
|  | 2 | 7 | 4 | 7 | 6 | 7 | 8 | 7 | A | 7 | C | 7 |
|  | 9 | 2 | 9 | 4 | 9 | 6 | 9 | 8 | 9 | A | 9 | C |
|  | 2 | 9 | 4 | 9 | 6 | 9 | 8 | 9 | A | 9 | C | 9 |
|  | B | 2 | B | 4 | B | 6 | B | 8 | B | A | B | C |
|  | 2 | B | 4 | B | 6 | B | 8 | B | A | B | C | B |
|  | D | 2 | D | 4 | D | 6 | D | 8 | D | A | D | C |
|  | 2 | D | 4 | D | 6 | D | 8 | D | A | D | C | D |
|  | E | 2 | E | 4 | E | 6 | E | 8 | E | A | E | C |
|  | 2 | E | 4 | E | 6 | E | 8 | E | A | E | C | E |
|  | F | 2 | F | 4 | F | 6 | F | 8 | F | A | F | C |
|  | 2 | F | 4 | F | 6 | F | 8 | F | A | F | C | 5 |
|  | G | 2 | G | 4 | G | 6 | G | 8 | G | A | G | C |
|  | 2 | G | 4 | G | 6 | G | 8 | G | A | G | C | 6 | ~R20

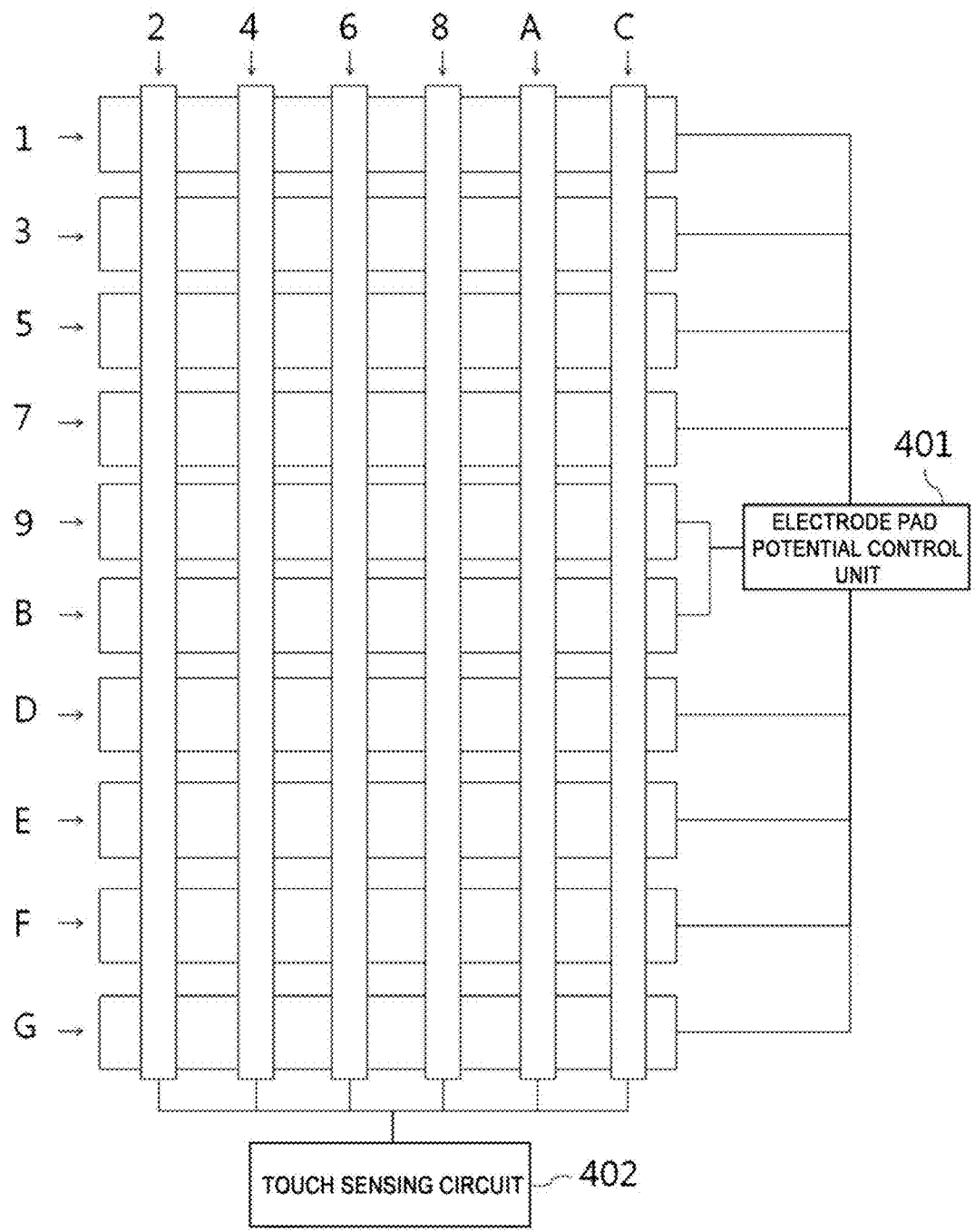
[Fig. 21b]

[Fig. 21c]

[Fig. 22a]
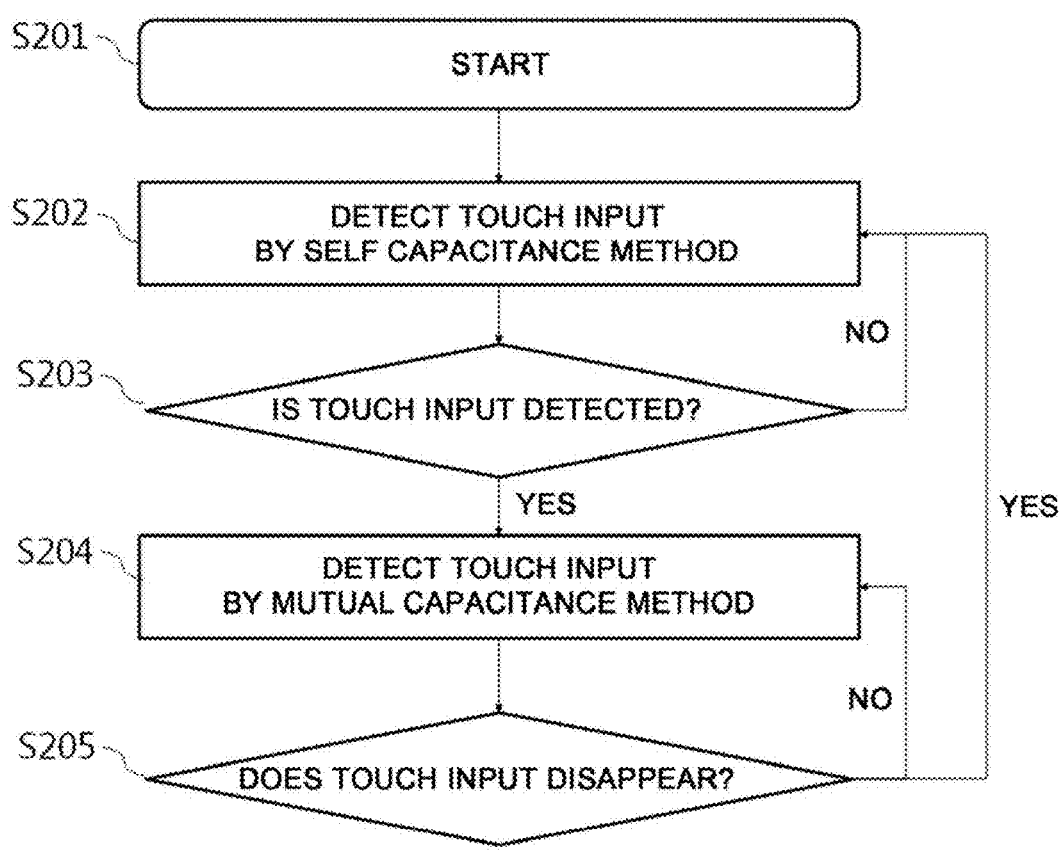

[Fig. 22b]
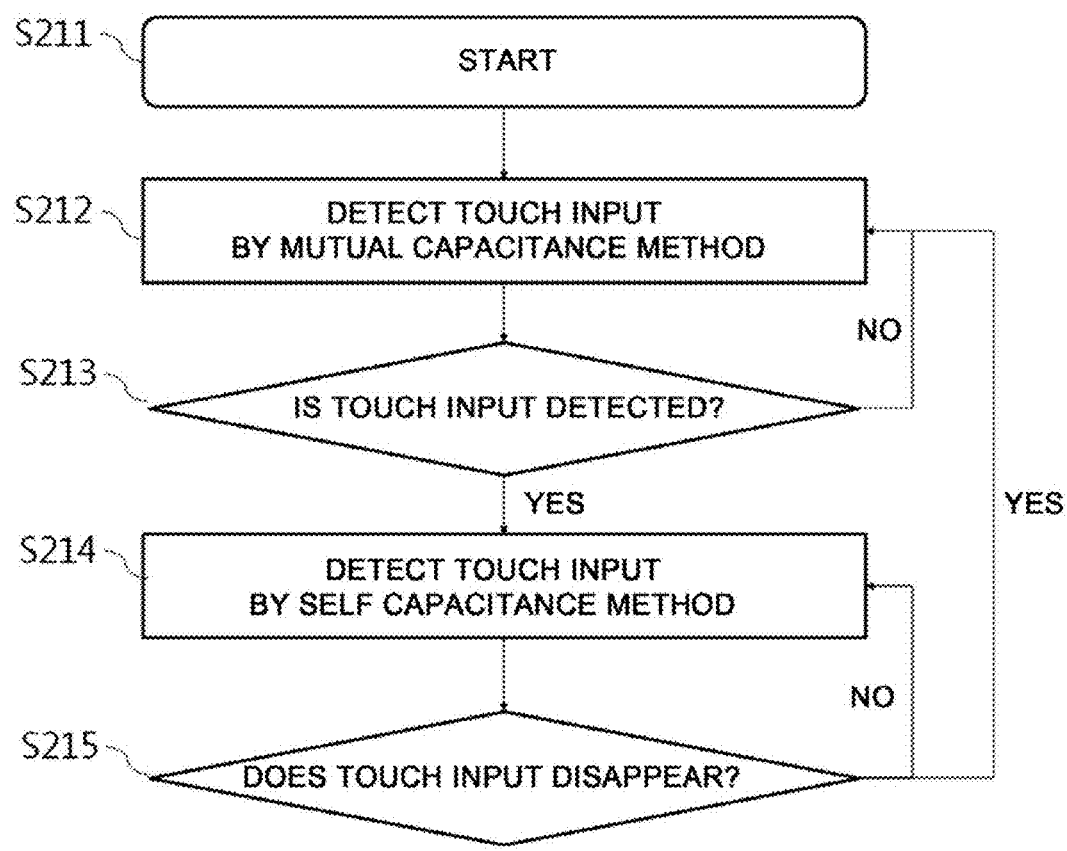

[Fig. 22c]
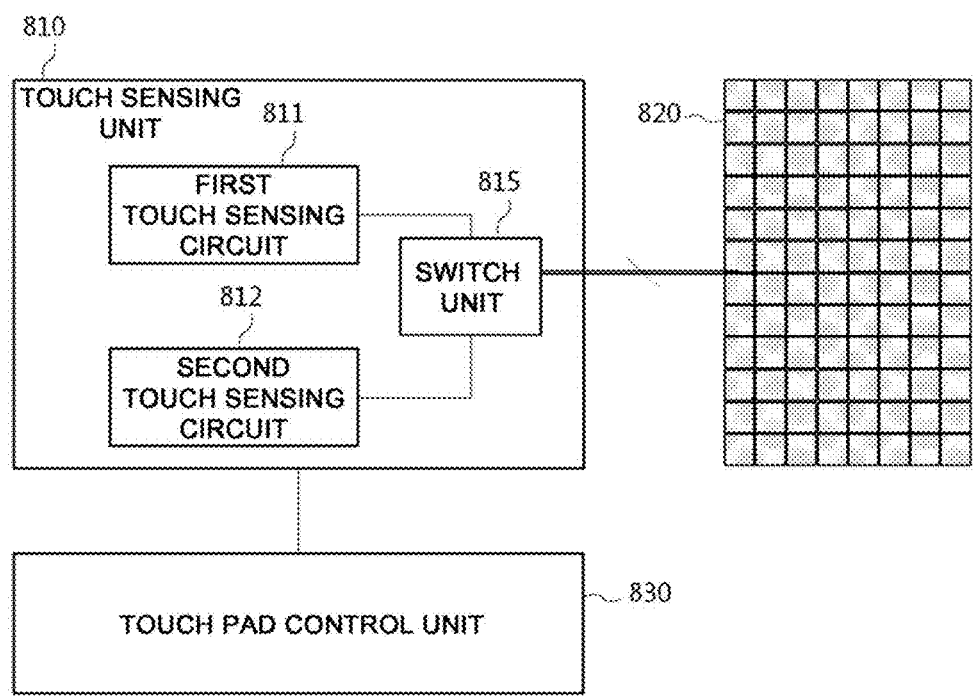

TOUCH INPUT SENSING METHOD FOR REDUCING INFLUENCE OF PARASITIC CAPACITANCE AND DEVICE THEREFOR

TECHNICAL FIELD

The present invention relates to a capacitive touch input control method.

BACKGROUND ART

FIGS. 1A and 1B are examples of a touch input circuit for describing a principle of self capacitive touch input. The touch input circuit may be an component of a electronic device.

To a node n1, ① an 'equivalent capacitance' formed by a capacitance Cf 18, a parasite capacitance Cp 20, and other capacitance Ce 23, ② a resistor Rref 12, ③ a non-inversion input terminal of an operation amplifier 15, ④ a switch 14, and ⑤ an electrode pad 16 may be connected. The electrode pad 16 may be a transparent or opaque conductive material. A reference potential Vref may be supplied to an inversion input terminal (−) of the operation amplifier 15. In one exemplary embodiment, the reference potential Vref may be larger than a ground potential.

In this case, when a conductor such as a finger is close to the electrode pad 16 when voltage is applied to the electrode pad 16, the capacitance Cf 18 as an element configuring the 'equivalent capacitance' is generated by forming an electric field between the capacitance Cf 18 and the conductor. That is, a value of the capacitance Cf 18 is changed according to whether a touch is input, and whether the touch is input may be verified by measuring the changed value.

Meanwhile, the parasite capacitance Cp 20 may be a capacitance which is not intently designed and formed between other parts of the electronic device and the electrode pad 16. Accordingly, the value of the parasite capacitance Cp 20 may be a value which may not be known in advance by the designer of the touch input circuit.

In this case, only when the value of the parasite capacitance Cp 20 is sufficiently small or not present, a change amount of the capacitance Cf 18 may be easily measured.

Further, noise which is generated or input from other parts of the electronic device is transferred to the node n1 through a node n2 which is present at one end of the parasite capacitance Cp. Other capacitance Ce 23 formed at another part of the electronic device may be further connected to the node n2.

An on/off state of the switch 14 may be determined on the basis of a difference value between reference voltage Vref applied to the inversion input terminal (−) of the operation amplifier 15 and voltage Vx of the node n1 applied to the non-inversion input terminal (+).

As illustrated in FIG. 1B, the voltage Vx of the node n1 may vary according to a change of the on/off state of the switch 14. 'Off' disclosed in a lateral axis of FIG. 1B means a time period for which the switch 14 maintains the off state, and 'On' may mean a time period for which the switch 14 maintains the on state.

When the switch 14 is in the on state, a change rate of the voltage Vx may be determined by a time constant τ which is determined by the 'equivalent capacitance' and the resistor Rref 12. When the switch 14 is in the off state, the voltage Vx drops to the reference potential again.

According to how much a finger 17 is close to the electrode pad 16, the magnitude of the capacitance Cf 18 may be changed, and as a result, the magnitude of the 'equivalent capacitance' may be changed. Accordingly, the value of the time constant τ may be changed according to the change amount of the capacitance Cf. The change of the time constant τ influences the change rate of the voltage Vx in the time period when the switch 14 maintains the on state as illustrated in FIG. 1B. Accordingly, information regarding the size of the time constant τ, the magnitude of the capacitance Cf 18, and how much the finger 17 influences the electrode pad 16 may be reversely calculated by using a value for a voltage Vx graph. As a result, it may be determined whether the touch input is performed.

For example, when the finger 17 is not present around the electrode pad 16, the capacitance Cf 18 is not present, and as a result, it may be assumed that the value of the 'equivalent capacitance' is Ce1. Thus, when the finger 17 is present around the electrode pad 16, the capacitance Cf 18 is present, and as a result, when the value of the equivalent capacitance' is Ce2, a relationship of Ce2>Ce1 may be satisfied. As a result, a time constant tau1 when the finger 17 is not present around the electrode pad 16 is smaller than a time constant tau2 when the finger 16 is present around the electrode pad 16. In FIG. 1B, when the finger 17 is not present around the electrode pad 16, the voltage Vx may more rapidly increased as compared with the finger 16 is present around the electrode pad 16. When using the phenomenon, for example, it may be determined whether the finger 16 is present around the electrode pad 16 by measuring a time taken for the voltage Vx to increase from 0 to Vref.

FIGS. 1C and 1D illustrate a circuit in which the resistor Rref 12 of FIG. 1A is replaced with a constant current source Iref 12_1 as the circuits corresponding to FIGS. 1A and 1B and a change according to a time of the voltage Vx at this time. An operation of the circuit according to FIGS. 1C and 1D can be easily understood by a person who understands the operational principle described in FIGS. 1A and 1B.

FIGS. 1E and 1F are examples of a touch input circuit for describing a principle of a mutual capacitive touch input. The touch input circuit may be a component of a electronic device.

Referring to FIG. 1E, a first electrode pad VCOM 11 and a second electrode pad VCOM 12 are insulated from each other by an insulator 511 on a substrate 512. In this case, when predetermined voltage is applied to the first electrode pad VCOM 11, a magnetic flux 510 generated in the first electrode pad VCOM 11 is directed to the second electrode pad VCOM 12. In this case, a mutual capacitance Cs is formed between the first electrode pad VCOM 11 and the second electrode pad VCOM 12 by the magnetic flux 510. In this case, when a touch input tool such as a finger is present in a space where the magnetic flux 510 discharged outside the insulator is included, the magnetic flux 510 discharged outside is not input to the second electrode pad VCOM 12. Accordingly, the value of the mutual capacitance Cs is changed. The mutual capacitive touch input circuit determines the touch input or not by measuring the value of the aforementioned mutual capacitance Cs. Like the first electrode pad VCOM 11 of FIG. 1E, an electrode to which the predetermined voltage is applied may be called a driving electrode pad and the second electrode pad VCOM 12 may be called a sensing electrode pad.

FIG. 1F illustrates an example of the mutual capacitive touch input circuit and an example of a switched capacitor integrated circuit. In FIG. 1F, two switches shift on/off states according to a first clock Clk1 and a second clock Clk2, respectively, and do not share the time period of the on-state. Current provided from a power source Vs(t) is charged in the capacitance Cs and then the charged charge is stored in an integral capacitance Cfb which is connected to the operation amplifier. That is, the capacitance Cs allows charges to be continuously accumulated at two ends of the integral capacitance Cfb while charge and discharge are continuously repeated. As the value of the capacitance Cs is increased, more charges per unit time may be charged at the two ends of the integral capacitance Cfb. Accordingly, the magnitude of the capacitance Cs may be determined by verifying output voltage Vfb(t) of the operation amplifier. In this case, the two ends of the capacitance Cs of FIG. 1F may be designed to be the first electrode pad VCOM 11 and the second electrode pad VCOM 12 of FIG. 1E, respectively.

The aforementioned electrode pads 16 are disposed vertically and horizontally in plural to measure the touch input or not for the electrode pad by the self capacitive type illustrated in FIGS. 1A to 1D. In this case, as the number of electrode pads 16 is increased, power consumption of the circuit for sensing the touch input is increased. Alternatively, as the number of operation amplifiers is increased, complexity of the circuit is increased. For example, when arrangement of the electrode pads has a matrix structure of 20*12, a total of 240 electrode pads are provided. When the aforementioned operation amplifier needs to be connected to each electrode pad one by one, the complexity of the circuit is very increased.

DISCLOSURE

Technical Problem

An object of the present invention is to provide a touch input sensing technique having low complexity and high efficiency even though a plurality of electrode pads is used in a touch input sensing device having a plurality of electrode pads which is disposed in a matrix structure.

Technical Solution

<Touch Input Sensing Method for Reducing Influence of Parasitic Capacitance and Device Therefor>

According to an aspect of the present invention, in order to avoid an effect of the parasite capacitance connected to the electrode pad, the same voltage is applied to the two ends of the parasite capacitance or the same voltage is always applied to the two ends of the parasite capacitance. As the detailed method, when the electrode pad 16 is connected to one end n1 of the parasite capacitance Cp and another part of the circuit including a noise source and the like is connected to the other end n2, the voltage Vx of one end n1 is applied to the other end n2. As a result, since voltage between the two ends of the parasite capacitance Cp is 0 or uniformly applied, there is no charge that is charged and discharged by the parasite capacitance, and thus, the effect by the parasite capacitance Cp is excluded and only a change amount of the capacitance Cf 18 may be successfully measured.

Hereinafter, technical solutions of the present invention which are provided according to various aspects of the present invention will be described. For help in understanding, some terms to be described below designate some reference numerals in the accompanying drawings in this specification. The designated reference numerals are to be exemplified.

An aspect of the present invention provides a touch input sensing device comprising: a touch input sensing electrode; a touch sensing unit connected to one point of the touch input sensing electrode to measure a change in a touch capacitance formed by the touch input sensing electrode according to a touch input; a second node included in the touch input sensing device to form a capacitance between the one point and the second node; and a potential control unit for providing a potential value following the potential of the one point to the second node to decrease a potential difference between the one point and the second node.

Another aspect of the present invention provides a user device including a touch input sensing device and a screen output device. In this case, the touch input sensing device includes 1) a touch input sensing electrode; 2) a touch sensing unit connected to one point of the touch input sensing electrode to measure a change in a touch capacitance formed by the touch input sensing electrode according to a touch input; 3) a second node included in the touch input sensing device to form a capacitance between the one point and the second node; and 4) a potential control unit for providing a potential value following the potential of the one point to the second node to decrease a potential difference between the one point and the second node. In addition, the screen output device includes: 5) image pixels; 6) a control line transferring a signal for controlling light output of the image pixels; and 7) a common electrode of the image pixels. In addition, the common electrode is the touch input sensing electrode.

<Self Capacitive Touch Input Sensing Method Using a Plurality of Electrode Pads and Device Therefor>

In the present invention, in order to solve the aforementioned objects, a method including sensing a touch input or not in some electrode pads which are selected from the plurality of electrode pads by using a multiplexer.

The touch input sensing device provided according to an aspect of the present invention comprises: a plurality of first group electrode pads; a plurality of second group electrode pads which is interposed between the first group electrode pads; and a plurality of multiplexers in which the touch sensing unit is connected to the output terminal. In addition, one first group electrode pad and one second group electrode pad are connected to the input terminal of each multiplexer.

In this case, the touch input sensing device may further include a switch unit so that the first group electrode pad and the second group electrode pad which are connected to the input terminal of the multiplexer are short-circuited or opened with respect to each multiplexer.

In this case, the touch input sensing device may further include a second node included in the touch input sensing device to form a capacitance between the output terminal and the second node; and a potential control unit for providing a potential value following the potential of the output terminal to the second node. In addition, the touch sensing unit may measure a change in the touch capacitance which is formed by the first group electrode pad or the second group electrode pad according to a touch input.

In this case, the first group electrode pads and the second group electrode pads may be a common electrode of the screen output device, which includes image pixels, the control line transferring a signal for controlling light output of the image pixels, and the common electrode of the image pixels.

In this case, the screen output device may be a TFT-LCD.

In this case, the second node may be present in the control line of the screen output device, which includes the image pixels, the control line transferring a signal for controlling light output of the image pixels, and the common electrode of the image pixels.

In this case, the first group electrode pad and the second group electrode pad which are connected to the input terminal of each multiplexer may be adjacent to each other.

The method of sensing the touch input provided according to another aspect of the present invention uses the aforementioned touch input sensing device provided according to an aspect of the present invention. The method comprises: controlling an output terminal of each multiplexer to be connected to the first group electrode pads; identifying a first electrode pad in which the touch input is performed among the plurality of first group electrode pads by using the plurality of touch sensing units; controlling the output terminal of each multiplexer to be connected to the second group electrode pads; and identifying a second group electrode pad in which the touch input is performed among the plurality of second group electrode pads by using the plurality of touch sensing units.

The method of sensing the touch input provided according to yet another aspect of the present invention uses the aforementioned touch input sensing device provided according to one aspect of the present invention. The method comprises: controlling an output terminal of each multiplexer to be connected to the first group electrode pads; identifying a first electrode pad in which the touch input is performed among the plurality of first group electrode pads by using the plurality of touch sensing units; controlling the output terminal of each multiplexer to be connected to the second group electrode pads; and detecting a touch input or not for the second group electrode pad which is connected to the first multiplexer by using the touch sensing unit connected to the first multiplexer.

The method of sensing the touch input provided according to still another aspect of the present invention uses the aforementioned touch input sensing device provided according to one aspect of the present invention. The method comprises: controlling the switch unit to short-circuit the first group electrode pad and the second group electrode pad which are connected to the input terminal of the multiplexer with respect to each multiplexer; identifying a first sensing region which is determined that the touch input is performed by using the plurality of touch sensing units; controlling the switch unit to open the first group electrode pad and the second group electrode pad which are connected to the input terminal of the first multiplexer connected to the first sensing region; connecting the first group electrode pad connected to the first input terminal to the first output terminal of the first multiplexer and determining a touch input or not by using the first touch sensing unit which is connected to the first output terminal; and connecting the second group electrode pad connected to the first input terminal to the first output terminal and determining a touch input or not by using the touch sensing unit.

In this case, in the aforementioned touch input sensing method, the first group electrode pads and the second group electrode pads may belong to a plurality of divided common electrodes which is formed in the TFT-LCD including the image pixels, the control line transferring a signal for controlling light output of the image pixels, and the common electrode of the image pixels.

Still yet another aspect of the present invention provides a method of sensing a touch input by using a plurality of electrode pads which is arranged in a matrix form. In the method, among the plurality of electrode pads, sensing the touch input to the plurality of first group electrode pads and sensing the touch input to the plurality of second group electrode pads which is interlaced between the plurality of first group electrode pads are performed at different times. In this case, the first group electrode pads and the second group electrode pads may be connected to the input terminal of the multiplexer.

Still yet another aspect of the present invention provides a method of sensing a touch input by using a plurality of electrode pads which is arranged in a matrix form. In the method, among the plurality of electrode pads, a first step of making one node set by electrically connecting two or more adjacent electrode pads by using the switch unit and then sensing the touch input to the node set may be performed. Next, a second step of short-circuiting the electric connection between the two or more electrode pads included in one node set by using the switch unit and sensing the touch or not for each of the two or more electrode pads may be performed. In this case, the two or more electrode pads may be connected to the input terminal of the aforementioned multiplexer.

<Mutual Capacitive Touch Input Sensing Method Using Plurality of Electrode Pads and Device Therefor>

An aspect of the present invention provides a touch input sensing device including a plurality of electrode pads which is arranged in a matrix form in vertical and horizontal directions. The device comprises: a first electrode pad; a second electrode pad; fifth electrode pads in a first group which are adjacent to the first electrode pad to surround the first electrode pad; fifth electrode pads in a second group which are adjacent to the second electrode pad to surround the second electrode pad; a touch input sensing circuit in the first group that measures a value of the capacitance which is formed between the first electrode pad and the fifth electrode pads in the first group by using an integrator in the first group connected to the fifth electrode pads in the first group; a touch input sensing circuit in a second group that measures a value of the capacitance which is formed between the second electrode pad and the fifth electrode pads in the fifth group by using an integrator in the second group connected to the fifth electrode pads in the second group; and an electrode pad potential control unit to apply a reference potential to the other electrode pad while applying a first potential different from the reference potential to one electrode pad of the first electrode pad and the second electrode pad.

In this case, the first electrode pad, the second electrode pad, the fifth electrode pads in the first group, and the fifth electrode pads in the second group may be included in a plurality of divided common electrodes which is formed in a TFT-LCD including image pixels, a control line transferring a signal for controlling light output to the image pixels, and a common electrode of the image pixels.

In this case, at least one fifth electrode pad included in the fifth electrode pads in the first group may be included even in the fifth electrode pad in the second group.

Another aspect of the present invention provides a touch input sensing device including a plurality of electrode pads which is arranged in a matrix form in vertical and horizontal directions. The device comprises: a first electrode pad; eight fifth electrode pads that are adjacent to the first electrode pad to surround the first electrode pad; and a touch input sensing circuit to measure a value of a capacitance which is formed between the first electrode pad and the eight fifth electrode pads by using an integrator in the first group which is connected to the eight fifth electrode pads.

In this case, the first electrode pad and the eight fifth electrode pads may be included in a plurality of divided common electrodes, which is formed in the TFT-LCD including the image pixels, the control line transferring a signal for controlling light output of the image pixels, and the common electrode of the image pixels.

In this case, the touch input sensing circuit in the first group includes only one integrator, and the one integrator may be switched between the eight fifth electrode pads to be sequentially connected with the eight fifth electrode pads.

In this case, the touch input sensing circuit in the first group may include eight integrators which are connected to the eight fifth electrode pads.

Yet another aspect of the present invention provides a touch input sensing device including a plurality of electrode pads which is arranged in a matrix form in vertical and horizontal directions. The device comprises: a first electrode pad; a second electrode pad; fifth electrode pads in a first group which are adjacent to the first electrode pad to surround the first electrode pad; fifth electrode pads in a second group which are adjacent to the second electrode pad to surround the second electrode pad; a touch input sensing circuit to measure a value of a capacitance which is formed between the first electrode pad and the fifth electrode pads in the first group by using a first integrator connected to the first electrode pad; a touch input sensing circuit to measure a value of a capacitance which is formed between the second electrode pad and the fifth electrode pads in the second group by using a second integrator connected to the second electrode pad; and an electrode pad potential control unit to apply a reference potential to the other electrode pad while applying a first potential different from the reference potential to one electrode pad of the fifth electrode pad in the first group and the fifth electrode pad in the second group.

In this case, the first electrode pad, the second electrode pad, the fifth electrode pads in the first group, and the fifth electrode pads in the second group may be included in a plurality of divided common electrodes, which is formed in a TFT-LCD including image pixels, a control line transferring a signal for controlling light output to the image pixels, and a common electrode of the image pixels.

In this case, at least one fifth electrode pad included in the fifth electrode pads in the first group may be included even in the fifth electrode pad in the second group.

Still another aspect of the present invention provides a touch input sensing device including a plurality of electrode pads which is arranged in a matrix form in vertical and horizontal directions. The device comprises: a first electrode pad; eight fifth electrode pads in a first group which are adjacent to the first electrode pad to surround the first electrode pad; a touch input sensing circuit to measure a value of a capacitance which is formed between the first electrode pad and the eight fifth electrode pads in the first group by using a first integrator connected to the first electrode pad; and an electrode pad potential control unit to apply a reference potential to the other electrode pad while applying a first potential different from the reference potential to one electrode pad of the eight fifth electrode pads and apply the first potential sequentially to the eight fifth electrode pads.

In this case, the first electrode pad and the eight fifth electrode pads may be included in a plurality of divided common electrodes, which is formed in the TFT-LCD including the image pixels, the control line transferring a signal for controlling light output of the image pixels, and the common electrode of the image pixels.

<Mutual Capacitive Touch Input Sensing Method Using Code Division Scheme and Device Therefor>

A method of calculating touch input information provided according to an aspect of the present invention uses first information including definition for p time periods $T\_v$. In addition, the method uses second information which is defined to correspond to each of the p time periods $T\_v$ and includes definition for p driving electrode sets $TEC\_v$ configured by $N\_v$ driving electrode pads selected from a plurality (=M) of driving electrode pads. In addition, the method uses a touch sensing circuit including the plurality of driving electrode pads and a charge accumulating capacitor which is connected to a capacitively coupled sensing electrode pad. In this case, v is an integer of 1 to p and p is an integer of 2 or more.

In this case, each driving electrode set which belongs to the p driving electrode sets is configured by driving electrode pads of different sets. In addition, the method includes acquiring an output value $TO\_v$ from the touch sensing circuit by applying a driving voltage only to all the driving electrode pads which belongs to the driving electrode set $TEC\_v$ for the time period $T\_v$; and calculating information on a touch input to a region between the plurality of driving electrode pads and the sensing electrode pad by using the p output values $TO\_v$.

In this case, the plurality of driving electrode pads is p, p is an integer of 3 or more, and $N\_v$ satisfies $N\_v=p-1$ and may be an integer of 2 or more.

In this case, the plurality of driving electrode pads and the sensing electrode pad may be arranged in a matrix form.

In this case, the plurality of driving electrode pads and the sensing electrode pad are provided separately from a display panel to be disposed on the display panel. In this case, the display panel may be one of a TFT panel and an IPS panel.

Alternatively, the plurality of driving electrode pads and the sensing electrode pad may be a plurality of divided common electrodes which is used as a component of the display panel for an operation of the display panel.

In this case, for the p time periods $T\_v$, the plurality of driving electrode pads and the sensing electrode pad are connected to the touch sensing circuit. The plurality of driving electrode pads and the sensing electrode pad may be connected to a predetermined reference potential Vref2 for at least some periods of a time except for the time periods $T\_v$.

In this case, the sensing electrode pad is adjacent to all of the plurality of driving electrode pads, and other electrode pads which are present in the touch panel may not be disposed between the sensing electrode pad and the plurality of driving electrode pads at all.

A method of detecting a touch input provided according to another aspect of the present invention comprises a first step of acquiring a first output value from a touch sensing circuit connected to a sensing electrode pad which is capacitively coupled with M driving electrode pads by applying a driving signal only to a driving electrode pad in a first set which is selected from the M driving electrode pads. In addition, for a second time period, the method includes a second step of acquiring a second output value from the touch sensing circuit by applying the driving signal only to a driving electrode pad in a second set which is selected from the M driving electrode pads. In addition, the method includes a third step of calculating information on a touch input to a region between the first driving electrode pad among the M driving electrode pad and the sensing electrode pad by using the first output value and the second output value.

A touch input device provided according to another aspect of the present invention comprises: a sensing electrode pad; a plurality (=M) of driving electrode pads that is capacitively coupled with the sensing electrode pad; a touch sensing circuit including a charge accumulation capacitor which is connected to the sensing electrode pad; and an electrode pad potential control unit to apply a driving signal to the plurality of driving electrode pads by a predetermined rule.

In this case, the potential control unit uses (1) first information including definition for p time periods T_v and second information that is defined to correspond to each of the p time periods T_v and includes definition for p driving electrode sets TEC_v which are configured by N_v driving electrode pads selected from the plurality of driving electrode pads; and (2) the touch sensing circuit. However, v is an integer of 1 to p and p is an integer of 2 or more.

In addition, each driving electrode set which belongs to the p driving electrode sets is configured by driving electrode pads in a different set.

In addition, the potential control unit executes (3) acquiring an output value TO_v from the touch sensing circuit by applying a driving voltage only to all the driving electrode pads which belong to the driving electrode set TEC_v for the time period T_v with respect to v=1 to p; and calculating information on a touch input to a region between the plurality of driving electrode pads and the sensing electrode pad by using the p output values TO_v.

<Method of Sensing Touch Input by Mutual Capacitance Method by Using Electrode Pads Arranged in Matrix Form and Device Therefor>

An aspect of the present invention provides a touch input device to sense a touch input by a mutual capacitance method by using a plurality of electrode pads which is arranged on a first layer in a matrix structure. The touch input device comprises: a sensing electrode formed by electrically connecting electrode pads in an even-numbered row of a first column and electrode pads in an odd-numbered row in a second column adjacent to the first column among the plurality of electrode pads; a driving electrode formed by electrically connecting electrode pads in an odd-numbered row of the first column and electrode pads in an even-numbered row in the second column adjacent to the first column among the plurality of electrode pads; an electrode pad potential control unit to apply a driving signal to the driving electrode; and a touch sensing circuit in which a charge accumulation capacitor is connected to the sensing electrode.

In this case, four electrode pads are arranged in a matrix form in a region where the driving electrode crosses the sensing electrode, and when the driving signal is applied to the driving electrode, a mutual capacitance between two electrode pads in the sensing electrode among the four electrode pads and two electrode pads in the driving electrode among the four electrode pads may be formed.

In this case, the plurality of driving electrode pads and the sensing electrode pad are provided separately from a display panel to be disposed on the display panel. In this case, the display panel may be one of a TFT panel and an IPS panel.

Alternatively, the plurality of driving electrode pads and the sensing electrode pad may be a plurality of divided common electrodes which is used as a component of the display panel for an operation of the display panel. In this case, for a first time period, all of the plurality of electrode pads are connected to the electrode pad potential control unit or the touch sensing circuit, and for at least some time periods except for the first time period, all of the plurality of electrode pads may be connected to a predetermined reference potential Vref2.

<Touch Input Method of Switching Mutual Capacitance Method and Self Capacitance Method and Touch Input Device Therefor>

An aspect of the present invention provides a touch input device comprising: a touch sensing unit to sense a touch input by selecting any one of a mutual capacitance method and a self capacitance method; a plurality of electrode pads which is electrically connected to the touch sensing unit and arranged in a matrix form; and a touch pad control unit controlling the touch sensing unit to perform touch sensing for the plurality of electrode pads by the self capacitance method in a first mode and perform the touch sensing for the plurality of electrode pads by the mutual capacitance method in a second mode.

In this case, the touch sensing unit includes a first touch sensing circuit sensing the touch input by the self capacitance method, a second touch sensing circuit sensing the touch input by the mutual capacitance method, and a switch unit. The touch pad control unit may selectively connect the plurality of electrode pads to the first touch sensing circuit or the second touch sensing circuit by controlling the switch unit according to the first mode and the second mode.

In this case, the touch pad control unit may perform the touch sensing for the plurality of electrode pads by the self capacitance method while the touch input to the plurality of electrode pads is not sensed and perform the touch sensing for the plurality of electrode pads by the mutual capacitance method while the touch input to the plurality of electrode pads is sensed.

In this case, the touch pad control unit may perform the touch sensing for the plurality of electrode pads by the mutual capacitance method while the touch input to the plurality of electrode pads is not sensed and perform the touch sensing for the plurality of electrode pads by the self capacitance method while the touch input to the plurality of electrode pads is sensed.

In this case, the plurality of electrode pads may be provided separately from a display panel to be arranged on the display panel. In this case, the display panel may be one of a TFT panel and an IPS panel.

Alternatively, the plurality of electrode pads may be a plurality of divided common electrodes which is used as a component of the display panel for an operation of the display panel. In this case, for a first time period, all of the plurality of electrode pads are connected to the touch sensing unit, and for at least some time periods except for the first time period, all of the plurality of electrode pads may be connected to a predetermined reference potential Vref2.

Another aspect of the present invention may provide a method of sensing a touch input in the touch input device including the plurality of electrode pads. The method may comprise detecting a touch input or not for the plurality of electrode pads by using a first sensing method when the touch input device is initialized; detecting a touch input or not for the plurality of electrode pads by using a second sensing method when it is determined that the touch input to the plurality of electrode pads is performed; and detecting a touch input or not for the plurality of electrode pads by using the first sensing method when it is determined that the touch input to the plurality of electrode pads disappears.

In this case, the first sensing method is the self capacitance method and the second sensing method is the mutual capacitance method. Alternatively, the first sensing method may be the mutual capacitance method and the second sensing method may be the self capacitance method.

Advantageous Effects

The present invention may provide a touch input sensing technique having low complexity and high efficiency even though a plurality of electrode pads is used in a touch input sensing device having a plurality of electrode pads which is arranged in a matrix structure.

DESCRIPTION OF DRAWINGS

FIGS. 1A and 1B are examples of a touch input circuit for describing a principle of a self capacitive touch input.

FIGS. 1C and 1D illustrate a circuit in which the resistor Rref 12 of FIG. 1A is replaced with a constant current source Iref 12_1 as the circuits corresponding to FIGS. 1A and 1B and a change according to a time of the voltage Vx at this time.

FIGS. 1E and 1F are examples of a touch input circuit for describing a principle of a mutual capacitive touch input.

FIG. 2A illustrates a self capacitive touch input circuit according to an exemplary embodiment of the present invention.

FIG. 2B is a circuit corresponding to FIG. 2A and illustrates an example of a circuit in which the resistor Rref 12 of FIG. 2A is replaced with a static current source Iref 12_1.

FIG. 3 illustrates an integrated input/output device 1 formed integrally while a 'capacitive touch sensor layer' and a 'screen output device' share one or more kinds of components. In the integrated input/output device 1, a touch IC T-IC 3 and a screen output control chip (display driver ID (DDI)) 12.

FIG. 4 illustrates a configuration around four VCOM electrodes which is disposed at the upper left of FIG. 3 in more detail.

FIGS. 5A to 5C illustrate structures in three image pixels N11, N31, and N33 illustrated in FIG. 4 in more detail, respectively.

FIG. 6A schematically illustrates problems described in FIGS. 5A to 5C and FIG. 6B is an example modified from FIG. 6A.

FIGS. 7A to 7C illustrate a structure of a circuit for removing an effect on a parasite capacitor according to three different exemplary embodiments.

FIG. 8A illustrates a plan view of an integrated input/output device 4 provided according to an exemplary embodiment of the present invention. FIG. 8B schematically illustrates an exploded cross-sectional view of the integrated input/output device 4 illustrated in FIG. 8A.

FIG. 9 illustrates several examples of a timing diagram of a static driving signal (a driving signal for sensing a capacitive touch sensor) and a pen driving signal (a driving signal for sensing a stylus pen) according to the exemplary embodiment of the present invention.

FIG. 10 is a timing diagram of a static driving signal, a pen driving signal, and a display unit driving signal according to the exemplary embodiment of the present invention.

FIG. 11 illustrates a technique of recognizing a touch input gesture according to another exemplary embodiment of the present invention.

FIG. 12 illustrates examples of a case where a waveform of the periodic voltage signal Vdp is provided in a periodic AC waveform without a DC component.

FIG. 13 illustrates a circuit structure that removes an influence on a parasite capacitance Cp,yy according to the exemplary embodiment of the present invention in the circuit of FIG. 12.

FIGS. 14A and 14B illustrate a configuration of applying a signal having the same voltage to a touch input device and a display device according to the exemplary embodiment of the present invention.

FIG. 15 is a diagram for describing an arrangement of the electrode pads a method of sensing a touch input by a self capacitance method by using the arrangement according to the exemplary embodiment of the present invention.

FIGS. 16A to 16C are diagrams for describing a method of sensing a touch input by a self capacitance method by using a plurality of electrode pads according to another exemplary embodiment of the present invention.

FIGS. 17A to 17F illustrate a structure of a circuit to which a method of sensing a touch input by a mutual capacitance method by using electrode pads arranged in a tile structure according to an exemplary embodiment of the present invention may be applied.

FIGS. 18A and 18B illustrate an example of a touch sensing circuit provided according to the exemplary embodiment of the present invention.

FIG. 19 illustrates a structure to which a method of sensing a touch input by a mutual capacitance method by using electrode pads arranged in a tile structure according to another exemplary embodiment of the present invention may be applied.

FIGS. 20A to 20D are diagrams for describing a method of detecting whether a touch input event occurs in a specific electrode pad according to another exemplary embodiment of the present invention.

FIGS. 21A to 21C illustrate a structure to which a method of sensing a touch input by a mutual capacitance method by using electrode pads arranged in a tile structure according to another exemplary embodiment of the present invention may be applied.

FIGS. 22A and 22B illustrate a switching order of the touch input method of the touch input device according to the exemplary embodiment of the present invention.

FIG. 22C illustrates a configuration of the touch input device according to the exemplary embodiment of the present invention.

MODES OF THE INVENTION

In order to sufficiently understand an operating advantage of the present invention and an object achieved by the present invention and exemplary embodiments of the present invention, the accompanying drawings illustrating the exemplary embodiments of the present invention and contents disclosed in the accompanying drawings should be referred. The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. It is to be understood that the terminology used therein is for the purpose of describing particular embodiments only and is not intended to be limiting. It must be noted that, as used in the specification and the appended claims, the singular forms include plural references unless the context clearly dictates otherwise.

Exemplary Embodiment: Touch Input Sensing Method for Reducing Influence of Parasitic Capacitance and Device Therefor FIG. 2A illustrates a self capacitive touch input circuit according to an exemplary embodiment of the present invention. To a node n1, ① an 'equivalent capacitance' formed by a touch capacitance Cx,xx, a parasite capacitance Cp,yy, and other capacitance Ce 23, ② a resistor Rref 12, ③ a non-inversion input terminal (+) of an operation amplifier 15, ④ a switch 14, and ⑤ an electrode pad VCOM,xx may be connected. The electrode pad VCOM,xx may be a transparent or opaque conductive material. A reference potential Vref may be supplied to an inversion input terminal (−) of the operation amplifier 15. In the exemplary embodiment, the reference potential Vref may be larger than a ground potential. In this case, when the electrode pad VCOM,xx is close to a dielectric field such as a finger, the touch capacitance Cx,xx of the equivalent capacitance is generated by forming an electric field between the electrode pad and the dielectric material. That is, a value of the touch capacitance Cx,xx is changed according to a touch input or not, and the touch input may be verified by measuring the changed value. Meanwhile, the parasite capacitance Cp,yy may be an undesired capacitance formed between the electrode pad VCOM,xx and other different circuits. In this case, only when the value of the parasite capacitance Cp,yy is sufficiently small or not present, a change amount of the touch capacitance Cx,xx may be easily measured. Further, in any case, the parasite capacitance Cp,yy may be dynamically changed over time. Further, the node n2 as one end of the parasite capacitance Cp,yy has side effects in which noise input from another part of the circuit is transferred to the node n1. Other capacitance Ce 23 formed at another part of the circuit may be further connected to the node n2. An on/off state of the switch 14 may be determined according to a difference value between reference voltage Vref applied to an inversion input terminal of the operation amplifier 15 and voltage Vx,xx of the node n1 applied to the non-inversion input terminal.

FIG. 2B is a circuit corresponding to FIG. 2A and illustrates an example of a circuit in which the resistor Rref 12 of FIG. 2A is replaced with a static current source Iref 12_1.

In the circuit of FIGS. 2A and 2B, an amplifier 24 is further disposed between the node n1 and the node n2. The amplifier 24 functions to allow the voltage Vx,xx and the voltage Vy,yy to be forcibly the same as each other or substantially the same as each other, or functions to largely reduce a difference between the voltage Vx,xx and the voltage Vy,yy. As a result, voltage between two ends of the parasite capacitance Cp becomes 0 or a value close to 0. As a result, current from the node n1 to the node n2 never or hardly flows and thus, the effect of the parasite capacitance Cp is lost. As a result, only the capacitance Cx,xx configures the 'equivalent capacitance'. Accordingly, according to the circuit in FIGS. 2A and 2B, only the change amount of the capacitance Cx,xx may be successfully measured.

FIG. 3 illustrates an integrated input/output device 1 formed integrally while a 'capacitive touch sensor layer' and a 'screen output device' share one or more kinds of components. In the integrated input/output device 1, a touch IC T-IC 3 and a screen output control chip (display driver ID (DDI)) 12.

Herein, the capacitive touch sensor layer may mean a device in which transparent electrodes are disposed on a signal layer or two layers.

In addition, the screen output device may be a liquid crystal display and preferably, a TFT-LCD panel. The TFT-LCD panel may include constitute elements such as an LCD panel, a diffusion plate, a light guide plate, a reflection plate, a light source, a glass substrate, an LC layer, a black matrix, color filters, a common electrode VCOM, an alignment film, a polarizing film, a spacer, and a plurality of control lines (a data control line and/or a gate control line), and this technique is well known. The common electrode VCOM is formed and provided as a wide single substrate over the entire area of the TFT-LCD panel or may be segmented and divided in an M*N matrix.

In the screen output control chip 2, terminals DL connected to the plurality of data control lines provided in the screen output device, terminals CL connected to the plurality of gate control lines provided in the screen output device, and terminals VCOM[M*N] connected to the plurality of VCOM electrodes divided in the M*N matrix among the components configuring the screen output device are provided. In the exemplary embodiment of FIG. 3, M=12 and N=8.

In the touch IC 3, the terminals VCOM[M*N] connected to the plurality of VCOM electrodes are similarly provided. In FIG. 3, terminals VCOM[12*8] connected to the screen output control chip 2 and the terminals VCOM[M*N] connected to the touch IC 13 are the same as each other.

In the exemplary embodiment of the present invention, in the VCOM electrodes, the touch IC 3 and the screen output control chip 2 dividedly had a control zone over time.

That is, in the integrated input/output device 1 of FIG. 3, the "capacitive touch sensor layer' and the 'screen output device' share at least the plurality of VCOM electrodes as a common component. Herein, each of the plurality of VCOM electrodes may correspond to the VCOM,xx electrode (that is, the aforementioned electrode pad) illustrated in FIG. 2A.

FIG. 4 illustrates a configuration around four VCOM electrodes which is disposed at the upper left of FIG. 3 in more detail.

The plurality of data control lines DL1, DL2, DL3, . . . is extended vertically in the drawing and the plurality of gate control lines CL1, CL2, CL3, . . . is extended laterally in the drawing. The image output from the image pixels which are present at cross points of the control lines may be controlled by controlling potentials of the data control lines DL1, DL2, DL3, . . . and the gate control lines CL1, CL2, CL3, . . . . Herein, the image pixels which are present at cross points are represented by reference numeral of Nyy. For example, the image pixel in the node where the data control line DL1 and the gate control line GL1 cross each other is represented by N11.

Herein, the image pixel may represent one pixel binding RGB, that is, one pixel unit. In one image pixel, three data lines and one gate line for 'R', 'G', and 'B' may be provided. In all the image pixels, the aforementioned common electrodes VCOM are closely disposed. The technique is well known.

In FIG. 4, two data control lines and two gate control lines pass through one VCOM electrode, but the number may be larger or smaller.

FIGS. 5A to 5C illustrate structures in three image pixels N11, N31, and N33 illustrated in FIG. 4 in more detail, respectively.

Referring to FIG. 5A, an electric signal applied through the data control line DL1 influences a transistor T11, and in this case, the gate control line GL1 adjusts the gate voltage of the transistor T11. The screen output device illustrated in FIGS. 3 and 4 includes the electrode of VCOM,xx. In this case, various capacitors 61 to 66 (that is, capacitance components) are present among the data control line DL1, the gate control line GL1, the transistor Tyy (for example, T11), and the VCOM,xx electrode (for example, the VCOM,11 electrode). Some of the capacitors 61 to 66 are intentionally formed and other capacitors may be parasite capacitors which are unintentionally generated. In FIG. 5A, the capacitors 61 to 66 are modeled as total six, but may be modeled with a different number. Hereinafter, the present invention will be described on the assumption of an example of six modeled capacitors.

The VCOM,11 electrode is an electrode used as a sensor for the self-capacitive touch input as described in FIG. 2A. That is, the VCOM,11 is a component which commonly uses the touch IC 3 and the screen output control chip 2 of FIG. 3. To this end, in the exemplary embodiment of the present invention, the VCOM,11 may be used by time-dividing the touch IC 3 and the screen output control chip 2. VCOM,xx other than VCOM,11 is the same.

It is not easy to calculate the equivalent capacitor by the capacitors 61 to 66. Nevertheless, it can be understood that an amount of the charges flowing through the capacitors 64, 65, and 66 which are directly connected to the VCOM,11 electrode, and a touch input sensing characteristic by a capacitance ΔCx,11 formed between the VCOM,11 electrode and a touch input tool 17. In terms of the touch IC 3, the capacitors 61 to 66 and the like may be integrally considered as the parasite capacitor C11.

The parasite capacitor C11 may be referred to as a capacitor that sets nodes n11 to n12 as the first electrode and nodes n21 to n24 as the second electrode.

In a circuit model illustrated in FIG. 5A, the parasite capacitor C11 is connected to total three points of the VCOM,11 electrode, the data control line DL1, and the gate control line GL1, but since the amount of charges moving through a dual gate control line GL1 is small, two terminals of the parasite capacitor C11 may approximate the VCOM, 11 electrode and the data control line DL1.

Herein, the capacitance ΔCx,11 varies according to the touch input tool 17 or proximity and represented by using a mark of Δ. Further, the amount of the charges flowing between the VCOM,11 electrode and the capacitors 64, 65, and 66 varies according to a variable electric characteristic of the data control line DL1 and the gate control line GL1, and the parasite capacitor ΔCp,11 is represented by using a mark of Δ.

Like the circuit illustrated in FIG. 2A, the voltages at both sides of the parasite capacitor are the same as each other or almost similar to each other to minimize the effect by the parasite capacitor. As a result, the voltage of the VCOM,11 electrode may be applied to the data control line DL1 as 1:1 by using the amplifier 24 so that the voltages of the VCOM, 11 electrode and the data control line DL1 which are two terminals of the parasite capacitor C11 are almost the same as each other.

As described above, some components of the capacitive touch sensor layer and the screen output device are shared, and the data control lines DL1, DL2, DL3, . . . may be shared. In the exemplary embodiment of the present invention, a time period of outputting the screen and a time period of sensing the capacitive touch input are exclusively divided. In the time period of outputting the screen, the electric signal corresponding to the image output data is applied to the data control lines DL1, DL2, DL3, . . . , but in the time period of sensing the capacitive touch input, in order to minimize an error of the capacitive touch input by the parasite capacitors ΔCp,11, ΔCp,12, ΔCp,13, . . . , the output of the amplifier 24 may be applied to the data control lines DL1, DL2, DL3, . . . .

Referring FIGS. 5A and 5B, in FIG. 5A, the VCOM electrode connected to the transistor T11 is the VCOM,11 electrode, and in FIG. 5B, the VCOM electrode connected to a transistor T31 is a VCOM,21 electrode. In this case, as described in FIG. 5A, the voltage of the VCOM,21 electrode may be applied to the data control line DL1 one to one by using the amplifier 24 so that the voltages of the VCOM,21 electrode and the data control line DL1 as two terminals of the parasite capacitor C31 are almost the same as each other. However, this may not be simply configured above. The reason is that an image pixel N11 and an image pixel N31 share the data control line DL1, the VCOM electrodes connected to the image pixel N11 and the image pixel N31 are different from each other as the VCOM,11 electrode and the VCOM,21 electrode, and the voltages of the VCOM,11 electrode and the VCOM,21 electrode may be different from each other. Accordingly, voltages of two terminals having different voltages may not be simultaneously applied to one data control line. A method of solving the problem will be described with reference to FIGS. 7A to 7C.

In order to describe an image pixel N33 again, referring to FIG. 5C, it is verified that the VCOM electrode becomes the VCOM,22 electrode. In this case, since the data control line DL3 is connected to the image pixel N33, the amplifier 24 is not connected between the VCOM,22 electrode and the data control line DL3 due to at least the data control line DL1 of FIGS. 5A and 5B.

In FIGS. 5A to 5C, the configuration in which the output terminal of the amplifier 24 is connected to the data control line DL is exemplified, but in another example, it can be easily understood that the output terminal of the amplifier 24 may be connected to the gate control line GL.

In the structure of FIGS. 5A to 5C, a switch SW1 may be connected to the VCOM,xx electrode. The switch SW1 is connected to Vref2 in a period when the display unit driving signal 53 of FIG. 10 to be described below is activated and may be connected to the node n1 in a period when the static driving signal 52 is activated. Herein, the Vref2 may be a GND, and may be a reference potential at which all the VCOM,xx electrodes are commonly connected while an image control signal is applied to the data control line DL and the gate control line GL. In addition, the node n1 may be a node corresponding to the node n1 illustrated in FIG. 2A. That is, the node n1 may be a node connected to the touch sensing sensor which uses the VCOM,xx electrode as the touch sensing sensor.

In addition, a switch SW2 may be connected between the data control line DL and the amplifier 24. The switch SW2 becomes an off state in the period when the display unit driving signal 53 is activated and may become an on state in the period when the static driving signal 52 is activated.

TABLE 1

| | SW1 | SW2 |
|---|---|---|
| Period when the display unit driving signal 53 is activated | Connected to Vref2 | OFF |
| Period when the static driving signal 52 is activated | Connected to n1 | ON |

FIG. 6A schematically illustrates the problems described in FIGS. 5A to 5C.

Referring to FIG. 6A, voltages of two or more VCOM,xx electrodes (the VCOM,11 electrode and the VCOM,21 electrode) having different voltages may be applied to one data control line DL1. In this case, of course, first voltage of the VCOM,11 electrode and second voltage of the VCOM,21 electrode may not be simultaneously applied to the data control line DL1. Anyway, in order to apply any potential to one data control line DL1, only the output of one amplifier 24 needs to be connected to one data control line DL1.

This is applied to another data control line DL3 illustrated in FIG. 6A.

FIG. 6A is a structure in which the data control line much more influences forming the parasite capacitance ΔCp,yy than the gate control line. On the contrary, in the case where the gate control line much more influences forming the parasite capacitance ΔCp,yy than the data control line, a structure illustrated in FIG. 6B may be applied.

FIGS. 7A to 7C illustrate a structure of a circuit for removing an effect on a parasite capacitor according to three different exemplary embodiments.

FIG. 7A illustrates a circuit structure in which voltage corresponding to the VCOM voltage is applied to the data control line according to the exemplary embodiment of the present invention.

In FIG. 7A, a structure in which any one of a plurality of VCOM,x1 electrodes (VCOM,11 electrode, VCOM,21 electrode, VCOM,31 electrode, . . . ) which may be connected to the data control line DL1 is selected randomly or by a predetermined rule to apply the selected VCOM,x1 voltage to the data control line DL1. In FIG. 7A, the VCOM,x1 electrode is selected by a multiplexer, but unlike this, the input terminal of the amplifier 24 may be directly connected to the specific VCOM electrode.

As illustrated in FIG. 7A, potentials of the VCOM,11 electrode and the VCOM,21 electrode depending on time may not fundamentally be the same as each other at all times, the potentials cannot but be different from each other.

FIG. 7B illustrates a circuit structure in which voltage corresponding to voltage of VCOM is applied to a data control line according to another exemplary embodiment of the present invention.

In FIG. 7B, in the data control line DL1, used is a structure in which potentials shown in a plurality of VCOM, x1 electrodes (a VCOM,11 electrode, a VCOM,21 electrode, . . . ) which may be connected to the data control line DL1 are averaged to be applied to the data control line DL1. To this end, an average value calculating circuit that makes an average of different voltages may be used. The average value calculating circuit may be implemented by using, for example, a principle of a differential amplifier that receives multiple inputs of one phase through a differential input terminal.

In FIG. 7B, although not strictly illustrated, an example of a waveform acquired by averaging voltages of the VCOM, 11 electrode and the VCOM,21 electrode depending on time is illustrated.

FIG. 7C illustrates a circuit structure in which voltage corresponding to voltage of VCOM is applied to a data control line according to yet another exemplary embodiment of the present invention.

In FIG. 7C, in the data control line DL1, a configuration is taken, in which voltage provided by a predetermined method is output in a reference wave generator to be applied to the data control line DL1. FIG. 7C illustrates an example of an output of the reference wave generator. In this case, the output of the reference wave generator may be a periodic signal. In addition, the period may be the same as, for example, a period during which the switch 14 is opened and closed.

In an exemplary embodiment, the data control line DL, the gate control line GL, and VCOM,xx described in FIGS. 2 to 6 may be used for a function of a screen output control chip 2 during a period in which a display unit driving signal 53 illustrated in FIG. 10 is activated or used for a function of a touch IC (T-IC) 3 during a period in which a static driving signal 52 illustrated in FIG. 10 is activated. To this end, in an exemplary embodiment, when a capacitor which is artificially made is present among the capacitors 64, 65, and 66 of FIG. 5A, a switch not illustrated in FIGS. 5A, 5B, and 5C may be provided on a path between the capacitor and VCOM,xx. In addition, the switch SW2 may be provided even on a path between the data control line DL1 and the output terminal of the amplifier 24.

FIG. 8A illustrates a plan view of an integrated input/output device 4 provided according to an exemplary embodiment of the present invention. FIG. 8B schematically illustrates an exploded cross-sectional view of the integrated input/output device 4 illustrated in FIG. 8A. Hereinafter, the integrated input/output device 4 will be described with reference to FIGS. 8A and 8B together.

The integrated input/output device 4 may be a device in which the static touch sensor layer 100, the screen output device 200, and the touch pen sensor layer 300 are combined.

A screen output control chip (D-IC) 121 that processes a display signal together with a material for display may be included in or connected to the screen output device 200. In this case, the screen output control chip 121 may be a device including a display driver IC (DDI). In an exemplary embodiment, the DDI may serve to adjust a transistor attached to a subpixel displaying RGB which are three primary colors among respective pixels provided on a display screen and be divided into a gate IC and a source IC.

In an exemplary embodiment, the DDI is connected with a timing controller (T-CON) and used together with the T-CON to control a display device.

A touch IC (T-IC) 111 that processes a signal for static touch input detection together with a material for the static touch input detection may be included in or connected to the static touch sensor layer 100 and a pen sensor chip 131 for processing a signal for pen touch input detection together with a material for pen touch input detection may be included in or connected to the touch pen sensor layer 300.

In this case, an order in which the three devices are stacked need not be determined as a specific order, but in an exemplary embodiment, the touch pen sensor layer 300 may be disposed on a lowermost layer, the screen output device 200 may be disposed on a middle layer, and the static touch sensor layer 100 may be disposed on an uppermost layer.

Further, for example, in the exemplary embodiment of the present invention, which is illustrated in FIGS. 3 to 7, the screen output device 200 and the static touch sensor layer 100 are integrally formed to share some components (e.g., the VCOM electrode).

Further, in another exemplary embodiment, two or more predetermined devices among the static touch sensor layer 100, the screen output device 200, and the touch pen sensor layer 300 may share the component with each other. When the component is shared as described above, the case may be called a name of 'integrated' or 'hybrid'.

The screen output device 200 may be provided by using devices such as LCD, PDP, AMOLED, and OLED. When the static touch sensor layer 100 or the touch pen sensor layer 300 covers the screen output device 200, the touch panel covering the screen output device 200 may be configured to be substantially transparent with respect to an eye of a person so as to visually verify the output of the screen output device 200 when the static touch sensor layer 100 or the touch pen sensor layer 300 covers the screen output device 200.

The static touch sensor layer 100 and the touch pen sensor layer 300 may be provided to cover an emission area of the screen output device 200. When the person takes input gesture for a specific coordinate on the screen output device 200, touch panels need to be able to accurately detect a coordinate where the input gesture is taken.

In an exemplary embodiment, when display resolution of the screen output device 200 is represented by R1, user input resolution of the touch pen sensor layer 300 is represented by R2, and user input resolution of the static touch sensor layer 100 is represented by R3, for example, a relationship of R1>R2>R3 may be established. When R2 and R3 come close to R1, a further improved user input experience may be provided.

FIG. 9A is a timing diagram of a static driving signal (that is, a driving signal for sensing a capacitive touch sensor) and a pen driving signal (that is, a driving signal for sensing a stylus pen) according to the exemplary embodiment of the present invention. In an exemplary embodiment of the present invention, the static driving signal 52 may be intermittently (that is, meaning cut-off in the middle) at a predetermined period T on a time axis. In this case, the static driving signal 52 may be continued as long as a predetermined second continuous period T2. Patterns of the static driving signals 52 during respective second continuous periods T21 and T22 may be the same as each other or different from each other. In this case, the pen driving signal 51 may be generated so as not to overlap with the static driving signal 52 in terms of a generation time period. In FIG. 9, it is illustrated that during the first continuous periods T1, T11, and T22 which are all periods other than the second continuous period T2 where the static driving signal 52 is generated, the pen driving signal 51 is generated.

The static driving signal may be an internal signal meaning that sensing of the capacitive touch sensor is allowed to be achieved and the pen driving signal may be an internal signal meaning that sensing of the stylus pen is allowed to be achieved.

FIG. 9B illustrates a timing diagram modified from FIG. 9A. In FIG. 9B, the pen driving signal 51 may be generated between the second continuous periods 52 which are periods in which the static driving signal 52 is generated or otherwise.

FIG. 9C illustrates another timing diagram modified from FIG. 9A. A temporal gap may be present between the first continuous periods T3 of the pen driving signal 51 and the second continuous period T2 of the static driving signal 52.

In FIG. 9, three examples are described, but if the generation periods of the pen driving signal 51 and the static driving signal 52 may be made not to overlap with each other on the time axis, a modified example having any form will also be included in the scope of the present invention.

FIGS. 10A and 10B are timing diagrams of a static driving signal, a pen driving signal, and a display unit driving signal according to the exemplary embodiment of the present invention. The static driving signal and the pen driving signal of FIGS. 10A and 10B show the same example as those illustrated in FIG. 9C. In addition, herein, the display unit driving signal may be, for example, a driving signal of the DDI, that is, a DDI driving signal.

The timing diagram of FIG. 10A may be applied when the screen output device 200 and the static touch sensor layer 100 are separately provided on different layers.

In particular, the timing diagram of FIG. 10A may be applied when the screen output device 200 and the static touch sensor layer 100 are integratively provided. When the screen output device 200 and the static touch sensor layer 100 are integrated, a component which both devices share with each other may be present and in this case, both devices may temporally divide a control right for an input/output characteristic or an electric state of the component at predetermined different times. As a result, as illustrated in FIG. 10A, a fourth period continuous period T4 which is a generation period of the display unit driving signal 53 may not overlap with the second continuous period T2 which is the generation period of the static driving signal 52.

FIG. 10B illustrates a modified example of FIG. 10A. In FIG. 10A, it is illustrated that the third continuous period T3 which is the generation period of the pen driving signal 51 is included in the fourth period continuous period T4 which is the generation period of the display unit driving signal 53, but in FIG. 10B, it is illustrated that the third continuous period T3 which is the generation period of the pen driving signal 51 and a fifth continuous period T5 which is the generation period of the display unit driving signal 53 partially overlap with each other.

Although not illustrated, the generation period of the pen driving signal 51 and the generation period of the display unit driving signal 53 may not overlap with each other.

The timing diagrams illustrated in FIG. 10 may be modified as much as you want when a first condition in which the continuous period of the static driving signal 52 does not overlap with the continuous period of the pen driving signal 51 and a second condition in which the continuous period of the static driving signal 52 does not overlap with the continuous period of the display unit driving signal 53 are simultaneously satisfied.

FIG. 11 illustrates a technique of recognizing a touch input gesture according to another exemplary embodiment of the present invention.

A touch input sensing circuit 10 presented in FIG. 11 may include an operational amplifier 215 and an integral capacitor Cf connected between inverse input and output terminals of the operational amplifier 215. A voltage signal Vdp may be input in a non-inverse input terminal of the operational amplifier 210. In addition, for easy description, an input terminal 211 of the touch input sensing circuit 10 may be defined and the input terminal 211 may be a terminal which is the same as the inverse input terminal of the operational amplifier 215.

The voltage signal Vdp may be a signal having periodicity. Furthermore, the voltage signal Vdp may be a periodic signal of which a DC component is 0, that is, an AC periodic signal. Alternatively, the voltage signal Vdp may be not the periodic signal but a signal including a component of a frequency fc.

In FIG. 11, a magnitude of current that flows through a node Vx,xx may be influenced by a magnitude of an equivalent capacitance in which a capacitance Cx,xx formed between the electrode pad VCOM,xx and a finger 17 and a parasitic capacitance Cp,yy are coupled to each other. The equivalent capacitance may be called Cxe.

The input terminal 211 of the touch input sensing circuit 10 may be connected to VCOM,xx illustrated in FIG. 4.

FIG. 12 illustrates an example of a case where a waveform of the periodic voltage signal Vdp is provided in a periodic AC waveform without a DC component.

FIG. 12A illustrates an AC sine wave, FIG. 12B illustrates an AC triangular wave, and FIG. 12C illustrates an AC square wave. In each case, output voltage Vo of the operational amplifier 215 of FIG. 11 outputs the same or similar waveform as the AC sine wave, the AC triangular wave, and the AC square wave. The output voltage Vo may have a frequency component different from the center frequency fc and the different frequency component may be (1) a frequency component included in the voltage signal Vdp, (2) a frequency component distorted and generated from the voltage signal Vdp according to a non-linear transfer function, or (3) a frequency component provided by noise input from the outside.

In this case, an amplitude of the output voltage Vo may show a tendency to be in proportion to the magnitude of the equivalent capacitance Cxe and in inverse proportion to the integral capacitor Cf. Accordingly, in this case, since the magnitude of the integral capacitor Cf is known in advance, the amplitude of the output voltage Vo is measured to calculate the magnitude of the equivalent capacitance Cxe. In addition, in this case, when a value of the parasitic capacitance Cp,yy is known in advance to exclude an influence thereof or exclude an influence caused by the parasitic capacitance Cp,yy, a value of the capacitance Cx,xx formed between the electrode pad VCOM,xx and the finger 17 may be known.

In a case where the waveform of the periodic voltage signal Vdp is provided in the periodic AC waveform without the DC component, the amplitude of the output voltage Vo may be directly measured, but voltage output by mixing a specific sine wave with the output voltage Vo may be measured. Then, only the same frequency component as the sine wave among the components of the output voltage Vo may be extracted. As the sine wave, a signal having a frequency which is the same as the center frequency fc of the voltage signal Vdp may be used. As a result, noises of the frequency component other than the center frequency fc may be removed.

FIG. 13 illustrates a circuit structure that removes an influence on a parasite capacitance Cp,yy according to the exemplary embodiment of the present invention in the circuit of FIG. 12.

Voltage of the inverse input terminal (−) of the operational amplifier 215 is regarded to be the same as voltage of the non-inverse input terminal (−). Therefore, voltage of one-side node n1 of the parasitic capacitance Cp,yy connected to the same node n1 as the inverse input terminal (−) is the same as the voltage signal Vdp.

In this case, when the voltage signal Vdp is applied to the other-side node n2 of the parasitic capacitance Cp,yy, a potential difference between both ends of the parasitic capacitance Cp,yy becomes 0, and as a result, current does not flow through the parasitic capacitance Cp,yy. Therefore, the circuit may operate as if the parasitic capacitance Cp,yy is not present.

In this case, according to the exemplary embodiment, the other-side node n2 of the parasitic capacitance Cp,yy may be connected to a specific node of the electronic device and a switch SW3 may be installed so as to provide the voltage signal Vdp to the other-side node n2 at least during a time period in which the touch input is sensed.

FIG. 14 illustrate a configuration of applying a signal having the same voltage to a touch input device and a display device according to the exemplary embodiment of the present invention.

A VCOM control unit 220 may be connected to all of a plurality of different electrode pads VCOM,11, VCOM,12, VCOM,21, and VCOM,22.

A detailed configuration of the VCOM control unit 220 is presented in FIG. 14B. The same circuit as a touch input sensing circuit 10 of FIG. 11 or a circuit that the same or similar function thereas may be connected to the interface terminal 221 of the VCOM control unit 220 by a switch SW5. Alternatively, the interface terminal 221 of the VCOM control unit 220 may be connected to a reference potential Vref2 by the switch SW5. Herein, the reference potential may be a reference potential to which all VCOM,xx electrodes are commonly connected while the image control signal is applied to the data control line DL and the gate control line GL.

In this case, the respective touch input sensing circuits 10 may detect whether the touch is input in each of the electrode pads VCOM,11, VCOM,12, VCOM,21, and VCOM,22.

An operating timing of the switch SW5 may be set differently in the respective VCOM control units 220. For example, while the interface terminal 221 of the VCOM control unit 220 connected to the VCOM,11 electrode is connected to the reference potential Vref2, the interface terminal 221 of the VCOM control unit 220 connected to the VCOM,12 electrode may be connected to the touch input sensing circuit 10. In this case, the touch input is not detected in the VCOM,11 electrode, but the touch input may be detected in the VCOM,12 electrode.

In this case, a parasitic capacitance Cp,yy between respective electrode pads and gate control lines GL1, GL2, . . . and data control lines DL1, DL2, . . . adjacent to the respective electrode pads. In this case, according to a principle described in FIG. 13, a 'voltage signal Vdp' may be applied to the gate control lines GL1, GL2, . . . and the data control lines DL1, DL2, . . . . The voltage signal Vdp may be a signal which is the same as a signal provided to the non-inverting input terminal (+) of the operational amplifier 215 of the touch input sensing circuit 10.

Meanwhile, the 'image control signal' for respective image pixels N11, N12, . . . , N21, N22, . . . needs to also be provided to the gate control lines GL1, GL2, . . . and the data control lines DL1, DL2, . . . . Therefore, the 'voltage signal Vdp' may be applied during the first time period and the 'image control signal' may be applied during the second time period which does not overlap with the first time period. To this end, a switch SW4 may be used.

For example, the switch SW4 may be connected to the gate control lines GL1, GL2, . . . and the data control lines DL1, DL2, . . . during the periods T4 and T5 when the display unit driving signal 53 illustrated in FIG. 10 is activated and connected to a voltage signal (Vdp) output terminal during the period T2 when the static driving signal 52 is activated.

Hereinafter, an electronic device according to the exemplary embodiment of the present invention will be described with reference to FIGS. 11 to 14B.

The electronic device is an electronic device that applies the touch driving voltage to the touch electrode pad by the touch driving signal generating unit that applies the touch driving voltage Vdp to the touch electrode pad VCOM,xx disposed to the touch input capacitance Cx,xx with the user input tool 17. Herein, the 'touch driving signal generating unit' may be a device in which for example, the operational amplifier 215, the integration capacitor Cf, and the voltage signal Vdp generating unit illustrated are connected to each other, but is not limited thereto and may correspond to a touch input circuit having various other constitutions.

In this case, the electronic device is configured to apply the voltage corresponding to the touch driving voltage Vdp to a first pole n2, GL, DL of a second capacitor Cp,yy formed in the electronic device and distinguished from the touch input capacitance. In this case, a second pole n1 of the second capacitor Cp,yy may be directly connected to the touch electrode pad VCOM,xx.

Wires which are independent from each other may be drawn to M*N electrode pads illustrated in the exemplary embodiment of the present invention, respectively. That is, M*N electrode pads and M*N wires drawn from the electrode pads, respectively may be present.

Hereafter, exemplary embodiments of the present invention will be described in detail with reference to the drawings.

A touch input sensing device according to an exemplary embodiment of the present invention includes: a touch input sensing electrode VCOM,xx; a touch sensing unit 10 connected to one point n1 of the touch input sensing electrode to measure a change in a touch capacitance Cx,xx formed by the touch input sensing electrode according to a touch input; a second node n2 included in the touch input sensing device to form a capacitance Cp,yy between the one point n1 and the second node n2; and a potential control unit Vdp or 24 for providing a potential value following the potential Vx,xx of the one point to the second node to decrease a potential difference between the one point and the second node.

In this case, the touch input sensing electrode may be the common electrode of a screen output device, which includes the control line (e.g., DL1 or GL1) transferring a signal for controlling a light output of the image pixel and the common electrode VCOM,11 of the image pixel.

In this case, the second node may be present in the control line (e.g., DL1 or GL1) of the screen output device, which includes the image pixels, the control line transferring the signal for controlling the light output of the image pixels, and the common electrode of the image pixels.

In this case, the screen output device may be a TFT-LCD.

In this case, the touch input sensing electrode is a first common electrode (e.g., VCOM,11) among the plurality of common electrodes of the screen output device, which includes a plurality of image pixels, a plurality of control lines transferring signals for controlling light outputs of the plurality of image pixels, and a plurality of common electrodes (e.g., VCOM,11, VCOM,21, VCOM,31, . . . ) divided and provided for the plurality of image pixels and the followed potential value may be a potential value of any one common electrode (e.g., VCOM,11 or VCOM,21) selected by a predetermined scheme among the plurality of common electrodes.

Alternatively, the touch input sensing electrode is a first common electrode (e.g., VCOM,11) among the plurality of common electrodes of the screen output device, which includes a plurality of image pixels, a plurality of control lines transferring signals for controlling light outputs of the plurality of image pixels, and a plurality of common electrodes (e.g., VCOM,11, VCOM,21, VCOM,31, . . . ) divided and provided for the plurality of image pixels and the followed potential value may be a mean value of potential values of the plurality of common electrodes (e.g., VCOM, 11, VCOM,21, VCOM,31, . . . ).

In this case, the touch input sensing electrode may be the common electrode of the screen output device, which includes the image pixels, the control line transferring a signal for controlling light output of the image pixels, and the common electrode of the image pixels, and a period of the followed potential value may be the same as a period of the common electrode.

In this case, the touch sensing unit includes the operational amplifier 215 and a signal Vdp having a first frequency (fc) component is applied to a first input terminal (+) and the second node of the operational amplifier and the touch input sensing electrode may be connected to a second input terminal (−) of the operational amplifier.

According to another exemplary embodiment of the present invention, a user device including the touch input sensing device and the screen output device may be provided. In this case, the touch sensing device includes: 1) a touch input sensing electrode; 2) a touch sensing unit connected to one point of the touch input sensing electrode to measure a change in a touch capacitance formed by the touch input sensing electrode according to a touch input; 3) a second node included in the touch input sensing device to form a capacitance between the one point and the second node; and 4) a potential control unit for providing a potential value following the potential of the one point to the second node to decrease a potential difference between the one point and the second node. In addition, the screen output device includes: 5) image pixels; 6) a control line transferring a signal for controlling light outputs of the image pixels; and 7) a common electrode of the image pixels. In addition, the common electrode is the touch input sensing electrode.

Exemplary Embodiment: Self Capacitive Touch Input Sensing Method Using a Plurality of Electrode Pads and Device Therefor FIG. 15 is a diagram for describing an array of electrode pads and a method for sensing a touch input in a self capacitance method by using the electrode pads according to an exemplary embodiment of the present invention.

In FIG. 15, in the case of the electrode pads, 12 columns C1 to C12 and 20 rows R1 to R20 are disposed. That is, a total of 240 (=20*12) electrode pads are disposed in a tile form or a matrix form.

240 electrode pads illustrated in FIG. 15 may correspond to the electrode pads VCOM,xx illustrated in FIGS. 2A and 2B. For example, the electrode pads illustrated in FIG. 15 may be a common electrode VCOM included in the TFT-LCD panel. However, in the TFT-LCD panel according to some exemplary embodiments, the common electrode VCOM is provided as one broad sheet, but in the exemplary embodiment according to FIG. 15 of the present invention, 240 common electrode pieces are disassembled and provided. For example, VCOM,xx illustrated in FIGS. 2A and 2B and VCOM,11, VCOM,12, VCOM,21, and VCOM,22 illustrated in FIG. 4 may be some of 240 common electrode pieces. 240 common electrodes illustrated in FIG. 15 may be simultaneously connected to the reference potential.

In the exemplary embodiment according to FIG. 15, components indicated by reference numerals 12, 15, 14, and 24 illustrated in FIG. 2A or 2B may be coupled to all of 240 electrode pads illustrated in FIG. 15. In this case, whether the touch is input may be simultaneously detected with respect to all of 240 electrode pads.

In a modified example, 240 electrode pads illustrated in FIG. 15 are divided into a plurality of groups to detect whether the touch is input for each group. For example, in FIG. 15, touch pads corresponding to reference numerals 31, 32, 33, and 34 may be allocated to a first group, a second group, a third group, and a fourth group, respectively. That is, in FIG. 15, 240 electrode pads may be configured to belong to any one of 4 groups. Herein, 240 electrode pads are divided into 4 groups, but the total number of the groups may vary.

Further, in the example of FIG. 15, only electrode pads that belong to another group are arranged around the electrode pads that belong to the first group.

In an exemplary embodiment of the present invention, whether the touch is input may be first detected near the electrode pads that belong to the first group 31 and then, whether the touch is input may be detected in the order of the second group 32, the third group 33, and the fourth group 34.

To this end, a multiplexer 35 may be used, and the multiplexer may select any one of a total of touch pads that belong to the first group, the second group, the third group, and the fourth group. Of course, the multiplexer 35 may be controlled by a control unit (not illustrated).

In the case of FIG. 15, since a total of 60 electrode pads are present for each group, a total of 60 multiplexers 35 may be required.

In addition, the components indicated by reference numerals 12, 14, 15, and 24 illustrated in FIG. 2A or 2B may be connected to an output terminal of the multiplexer 35. That is, the output terminal of the multiplexer 35 may be the same node as the node n1 illustrated in FIG. 2A or 2B.

The multiplexer 35 and circuits attached to the output terminal may be collected and disposed in an area 36. On the contrary, one multiplexer 35 may be disposed in each of areas (e.g., 37) constituted by 4 pads adjacent to each other.

According to the exemplary embodiment of the present invention described by using FIG. 15, whether the touch is input in the electrode pad that belongs to the first group is detected to substantially find a touch position. In addition, it may be easily appreciated that the substantially found touch position may be more accurately and elaborately found by detecting whether the electrode pad that is present around the touch position which is substantially found is touched is detected among the electrode pads that belong to the second group, the third group, and the fourth group.

For example, in a first step of the sensing method according to the exemplary embodiment of the present invention, whether the touch is input may be detected only with respect to any one group among the first, second, third, and fourth groups. For example, whether the touch is input may be detected only with respect to the first group. In this case, as a result of detecting whether the touch is input only with respect to the first group, when the touch is input throughout an area 38, whether the touch is input will be detected in the electrode pads 31 corresponding to [R3, C1] and [R3, C3].

In a second step, whether the touch is input is determined with respect to electrode pads adjacent around the electrode pads where it is determined that the touch is input. For example, whether the touch is input may be additionally detected with respect to the electrode pads that belong to the second, third, and fourth groups that are present around the electrode pads 31 corresponding to [C1, R3] and [C3, R3] described above. That is, a detection result may be elaborated by detecting whether the touch is input with respect to the electrode pads 32, 33, and 34 corresponding to [R2, C1], [R2, C2], [R2, C3], [R2, C4], [R3, C2], [R3, C4], [R4, C1], [R4, C2], [R4, C3], and [R4, C4].

Exemplary Embodiment: Self Capacitive Touch Input Sensing Method Using a Plurality of Electrode Pads and Device Therefor FIGS. 16A to 16C are diagrams for describing a method for sensing a touch input in a self capacitance method by using a plurality of electrode pads according to another exemplary embodiment of the present invention. In FIG. 16A, an array and a configuration of the electrode pads may be the same as those FIG. 15.

A physical switch is provided among 4 electrode pads that belong to the first, second, third, and fourth groups adjacent to each other in up, down, let, and right directions to be connected to each other or separated from each other. In FIG. 16A, reference numeral 60 represents grouping 4 electrode pads that belong to the first, second, third, and fourth groups into a 'node set'. Hereinafter, a thing indicated by reference numeral 60 may be called a node set 60.

In a first step of the method according to the exemplary embodiment, first, 4 electrode pads that belong to the first, second, third, and fourth groups adjacent to each other in the up, down, left, and right direction in one node set may be electrically connected with each other with respect to the switches. Then, in FIG. 16, a total of 6*10=60 node sets are formed. Then, whether the touch is input may be determined with respect to each of 60 node sets. The reason is that 4 electrode pads 31, 32, 33, and 34 included in one node set 60 are electrically connected with each other, 4 electrode pads may be regarded as one electrode pad. Then, a substantial touch input position may be acquired. For example, when the touch is input in a portion marked with an asterisk in FIG. 16, it can be seen that the touch is achieved in a substantial node set NS5.

Thereafter, in a second step, with respect to the node set NS5 where it is determined that the touch input is present, the touch input position may be elaborated by determining whether the touch is input with respect to each of individual electrode pads 31 to 34 that are present in the node set NS5. In addition, the touch input position may be elaborated by determining whether the touch is input with respect to each of the individual electrode pads 31 to 34 that are present in other node sets NS1 to NS4 and NS6 to NS9 adjacent to the node set NS5. To this end, electrical connection among 4 electrode pads that are present in the node sets NS1 to SN9 may be at least released.

Exemplary Embodiment: Mutual Capacitive Touch Input Sensing Method Using a Plurality of Electrode Pads and Device Therefor FIGS. 17A to 17D illustrate a structure to which a method for sensing a touch input in a mutual capacitance method by using electrode pads arranged in a tile structure can be applied according to an exemplary embodiment of the present invention. A principle of the method for sensing the touch input in the mutual capacitance method has already been described in FIGS. 1E and 1F.

The electrode pads of FIG. 17A may be arranged similarly to FIG. 15. For example, the electrode pads are arranged in a 20*12 matrix structure. However, in FIG. 17A, some electrode pads 101 to 104 are used as driving electrode pads and other electrode pads 105 are used as sensing electrode pads to sense the touch input in the mutual capacitance method. On the contrary, some electrode pads 101 to 104 may be used as the sensing electrode pads and other electrode pads 105 may be used as the driving electrode pads.

In FIG. 17A, the electrode pads may be divided into a total of 5 groups and classified into the first electrode pad 101, the second electrode pad 102, the third electrode pad 103, the fourth electrode pad 104, and the fifth electrode pad 105. 8 fifth electrode pads 105 are disposed around each of the respective electrode pads 101 to 104. 3 or 5 electrode pads 105 are disposed around each of the respective electrode pads 101 to 104 at a peripheral area.

One first electrode pad 101 and 8 fifth electrode pads 105 surrounding the first electrode pad 101 may be collectively defined as a first area 107. In FIG. 17A, a plurality of first areas 107 may be provided.

In this case, the first electrode pad 101 included in the first area 107 may be driven by a driving signal. Then, a fringing capacitance may be formed between the first electrode pad 101 and 8 fifth electrode pads 105 and classified into a total of 8 fringing capacitance areas 106 to be conceptualized. In this case, for example, the touch input sensing circuit illustrated in FIG. 1F is provided in each of the 8 fifth electrode pads 105, and as a result, when components that sense the touch input independently from each other are taken, it may be appreciated that touch input sensing having very high resolution ma be performed. The structure of the circuit is illustrated in FIG. 17E.

In a modified example, one among 8 fifth electrode pads 105 included in the first area 107 is sequentially selected to be driven by the driving signal. Then, the fringing capacitance may be formed between the first electrode pad 101 and the selected fifth electrode pad 105. In this case, it may be appreciated that for example, the touch input sensing circuit illustrated in FIG. 1F is provided in the first electrode pad 101 to perform the touch input sensing. The structure of the circuit is illustrated in FIG. 17F.

This is similarly illustrated even in FIGS. 17B, 17C, and 17D. One second electrode pad 102 and 8 fifth electrode pads 105 surrounding the second electrode pad 102 may be collectively defined as a second area 108. One third electrode pad 103 and 8 fifth electrode pads 105 surrounding the third electrode pad 103 may be collectively defined as a third area 109. One fourth electrode pad 104 and 8 fifth electrode pads 105 surrounding the fourth electrode pad 104 may be collectively defined as a fourth area 110.

In an exemplary embodiment of the present invention, the touch input may be generally sensed through a total of 4 steps.

In a first step, as described in FIG. 17A, the first electrode pads 101 are driven to find whether the touch is input from the fifth electrode pad 105 surrounding the first electrode pads 101. In this case, a charge accumulation device (e.g., Cfb of FIG. 17E) of the integration circuit that detects whether the touch is input may be connected to not the first electrode pad 101 but the fifth electrode pad 105.

In a second step, as described in FIG. 17B, the second electrode pads 102 are driven to find whether the touch is input from the fifth electrode pad 105 surrounding the second electrode pads 102.

In a third step, as described in FIG. 17C, the third electrode pads 103 are driven to find whether the touch is input from the fifth electrode pad 105 surrounding the third electrode pads 103.

In a fourth step, as described in FIG. 17D, the fourth electrode pads 104 are driven to find whether the touch is input from the fifth electrode pad 105 surrounding the fourth electrode pads 104.

When the 4 steps are sequentially performed, detection resolution of the position of the touch input may be increased.

In another exemplary embodiment of the present invention, the touch input may be generally sensed through a total of 4 steps.

In a first step, as described in FIG. 17A, the fifth electrode pads 105 that are present around the first electrode pad 101 are sequentially driven to find whether the touch is input from the first electrode pad 101. In this case, a charge accumulation device (e.g., Cfb of FIG. 17F) of the integration circuit that detects whether the touch is input may be connected to not the fifth electrode pad 105 but the first electrode pad 101.

In a second step, the fifth electrode pads 105 that are present around the second electrode pad 102 are sequentially driven to find whether the touch is input from the second electrode pad 102.

In a third step, the fifth electrode pads 105 that are present around the third electrode pad 103 are sequentially driven to find whether the touch is input from the third electrode pad 103.

In a fourth step, the fifth electrode pads 105 that are present around the fourth electrode pad 104 are sequentially driven to find whether the touch is input from the fourth electrode pad 104.

When the 4 steps are sequentially performed, the detection resolution of the position of the touch input may be increased.

Hereinafter, a touch input sensing device according to an exemplary embodiment of the present invention will be described with reference to FIGS. 17A, 17B, and 17C together.

FIGS. 18A and 18B illustrate an exemplary embodiment of a touch sensing circuit provided according to an exemplary embodiment of the present invention.

According to an exemplary embodiment of the present invention, a touch input sensing device including a plurality of (e.g., 20*12=240) electrode pads 101 to 105 arranged in a matrix form in vertical and horizontal directions may be provided.

In particular, the touch input sensing device may include,
a first electrode pad 101 (e.g., [R2, C2]);
a second electrode pad 102 (e.g., [R2, C4]);
fifth electrode pads 105 of a first group, which are adjacent to the first electrode pad 101 and surround the first electrode pad 101 (e.g., [R1, C1], [R1, C2], [R1, C3], [R2, C1], [R2, C3], [R3, C1], [R3, C2], [R3, C3]);
fifth electrode pads 105 of a second group, which are adjacent to the second electrode pad 102 and surround the second electrode pad 102 (e.g., [R1, C3], [R1, C4], [R1, C5], [R2, C3], [R2, C5], [R3, C3], [R3, C4], [R3, C5]);
a touch input sensing circuit of the first group configured to measure a value of a capacitance formed between the first electrode pad 101 and the fifth electrode pads 105 of the first group by using an integrator 15-1 and Cfb1 of the first group connected to the fifth electrode pads 105 of the first group;
a touch input sensing circuit of a second group configured to measure a value of a capacitance formed between the second electrode pad 102 and the fifth electrode pads 105 of the second group by using an integrator 15-2 and Cfb2 of the second group connected to the fifth electrode pads 105 of the second group; and
an electrode pad potential control unit 400 configured to apply a reference potential to the other one electrode pad while applying a first potential other than the reference potential to any one electrode pad of the first electrode pad 101 and the second electrode pad 102.

The 'integrator' may be called a circuit including a capacitor that accumulates and integrates charges.

In addition, when voltage Vs1($t$) output from the electrode pad potential control unit 400 has a different value from the reference potential, voltage Vs2($t$) may have the reference potential.

In this case, at least one fifth electrode pad (e.g., [R2. C3]) included in the fifth electrode pads in the first group may be included even in the fifth electrode pad in the second group.

In this case, the first electrode pad, the second electrode pad, the fifth electrode pads in the first group, and the fifth electrode pads in the second group may be included in a plurality of divided common electrodes which is formed in the TFT-LCD including image pixels, a control line transferring a signal for controlling light output to the image pixels, and a common electrode of the image pixels.

In this case, the fifth electrode pads of the first group may be 8 fifth electrode pads surrounding the first electrode pad.

In this case, the touch input sensing circuit in the first group includes only one integrator, and the one integrator may be switched between the eight fifth electrode pads to be sequentially connected with the eight fifth electrode pads.

Alternatively, the touch input sensing circuit in the first group may include eight integrators 15-1 which are connected to the eight fifth electrode pads, respectively.

In FIG. 18A, it is illustrated that only one fifth electrode pad 105 and only one integrator 15-1 and Cfb1 are connected to the first electrode pad 101, but it may be easily appreciated that the plurality of fifth electrode pads 105 and the plurality of integrators 15-1 and Cfb1 may be connected to the first electrode pad 101.

An exemplary embodiment modified from the exemplary embodiment will be described by using FIGS. 17A, 17B, and 18B.

A touch input sensing device according to another exemplary embodiment of the present invention may include, a first touch input sensing circuit configured to measure values of capacitances Cs1 and Cs2 formed between the first electrode pad 101 and fifth electrode pads 105, 105_1 and 105_2 of the first group by using the first integrator 15-1 connected to the first electrode pad 101;

a second touch input sensing circuit configured to measure values of capacitances Cs3 and Cs4 formed between the second electrode pad 102 and fifth electrode pads 105, 105_3 and 105_3 of the second group by using the second integrator 15-2 connected to the second electrode pad 102; and an electrode pad potential control unit 400 configured to apply a reference potential Vs3($t$)=Vs4($t$)=GND to the other one group while applying a first potential Vs1($t$) and Vs2($t$) different from the reference potential to any one group among the fifth electrode pad of the first group and the fifth electrode pads of the second group.

In this case, the first electrode pad, the second electrode pad, the fifth electrode pads in the first group, and the fifth electrode pads in the second group may be included in a plurality of divided common electrodes which is formed in a TFT-LCD including image pixels, a control line transferring a signal for controlling light output to the image pixels, and a common electrode of the image pixels.

In this case, 8 fifth electrode pads may be disposed in the matrix form around the first electrode pad 101. In this case, the electrode pad potential control unit 400 may be configured to apply the reference potential Vs2($t$)=GND to the other one electrode pad (e.g., 105 and 105_2) while applying the first potential Vs1($t$) different from the reference potential to any one electrode pad (e.g., 105 and 105_1) among the 8 fifth electrode pads and configured to sequentially apply the first potential to the 8 fifth electrode pads.

<Mutual Capacitive Touch Input Sensing Method Using Code Division Scheme and Device Therefor>

FIG. 19 illustrates a structure to which a method for sensing a touch input in a mutual capacitance method by using electrode pads arranged in a tile structure can be applied according to an exemplary embodiment of the present invention.

An array of the electrode pads of FIG. 19 may be the same as that of FIG. 15. However, FIG. 15 illustrates a structure in which some electrode pads are used as the driving electrode pads and other electrode pads are used as the sensing electrode pads to sense the touch input in the mutual capacitance method.

In FIG. 19, the driving electrode pads may be divided into a total of 4 groups and classified into a first electrode pad 201, a second electrode pad 202, a third electrode pad 203, and a fourth electrode pad 204. 4 sensing electrode pads 205 are disposed around each of the respective driving electrode pads 201 to 204. One or two sensing electrode pads 205 may be disposed around the respective driving electrode pads at a peripheral area.

In the exemplary embodiment, all driving electrode pads 201 to 204 may be simultaneously driven. However, driving signals having different types, that is, 4 types of pulse train shapes may be applied to the first driving electrode pad 201, the second driving electrode pad 202, the third driving electrode pad 203, and the fourth driving electrode pad 204, respectively and the driving signals may have a characteristic to be orthogonal to each other.

For example, when the touch is input in a position 206, sensor circuits connected to the sensing electrode pads 205 and 1205 may determine that the touch is input around the sensing electrode pads 205 and 1205. However, since three driving electrode pads of the first driving electrode pad 201, the second driving electrode pad 202, and the third driving electrode pad 203 are present around the sensing electrode pads 205 and 1205, a characteristic in which the driving signals applied to the first driving electrode pad 201, the second driving electrode pad 202, and the third driving electrode pad 203 are orthogonal to each other may be granted as described above in order to find whether the fringing capacitance caused by any driving electrode pad among the driving electrode pads is changed by the touch input.

The sensing circuits may be individually connected to all sensing electrode pads 205 illustrated in FIG. 19, respectively or there may be provided a method for dividing the sensing electrode pads 205 into several groups and sequentially sensing the touch input to each group as described in the another exemplary embodiment. The multiplexer may be required for a latter scheme.

FIGS. 20A to 20D are diagrams for describing a method for detecting whether a touch input event occurs in a specific electrode pad according to another exemplary embodiment of the present invention.

FIG. 20A separately illustrate only the driving electrode pads 201 to 204 disposed to adjacent to each other and only the sensing electrode pads 205 and 2205 interposed therebetween among the electrode pads illustrated in FIG. 19.

FIG. 20B illustrates an example of a touch sensing circuit connected to the electrode pads illustrated in FIG. 20A according to an exemplary embodiment of the present invention.

FIG. 20C illustrates a time period in which driving input is achieved with respect to the first driving electrode pad 201, the second driving electrode pad 202, the third driving electrode pad 203, and the fourth driving electrode pad 204. In the exemplary embodiment of FIG. 20C, a touch input sensing time period may e divided into an A-time period 521, a B-time period 522, a C-time period 523, and a D-time period 524 each having a predetermined duration (e.g., 2 ms). In FIG. 20C, a period having a logical high value represents a period in which the driving signal is input in the corresponding driving electrode pad.

For example, in the case of the second driving electrode pad 202, the driving signal is input during the time periods 521, 522, and 524 and the driving signal is not input during the time period 523. Therefore, it may be modeled in such a manner that an electric field is formed during the time periods 521, 522, and 524, but the electric field is not formed during the time period 523 between the second driving electrode pad 202 and the sensing electrode pads 205 and 2205 of FIG. 20A.

FIG. 20D illustrates an example of on/off timings of respective clocks illustrated in FIG. 20B.

A touch sensing signal output unit may be reset by using a switch Sreset at a pre-start time ts1 of the A-time period 521, a pre-start time ts2 of the B-time period 522, a pre-start time ts3 of the C-time period 523, and a pre-start time ts4 of the D-time period 524. In addition, results of sampling output voltage Vo(t) of the touch sensing signal output unit after operating the touch sensing signal output unit during the A-time period 521, the B-time period 522, the C-time period 523, and the D-time period 524 may be represented by y[0], y[1], y[2], and y[3], respectively.

In this case, y[0], y[1], y[2], and y[3] may be shown as follows.

$$y[0]=A+B+C$$

$$y[1]=A+B+D$$

$$y[2]=A+C+D$$

$$y[3]=B+C+D \quad \text{[Equation]}$$

In the above equation, 'A' represents an output vale of the touch sensing signal output unit generated by the capacitance Cs1 formed between the first driving electrode pad 201 and the sensing electrode pad 2205. 'A' represents, for example, a value measured and output during the A-time period 521. In the above equation, 'B' represents an output vale of the touch sensing signal output unit generated by the capacitance Cs2 formed between the second driving electrode pad 202 and the sensing electrode pad 2205. 'C' represents an output vale of the touch sensing signal output unit generated by the capacitance Cs3 formed between the third driving electrode pad 203 and the sensing electrode pad 2205. 'D' represents an output vale of the touch sensing signal output unit generated by the capacitance Cs4 formed between the fourth driving electrode pad 204 and the sensing electrode pad 2205.

When the touch input sensing time period 520 ends, S which is a value acquired by adding up y[0], y[1], y[2], and y[3] may be obtained. The S has the following relationship with the A, B, C, and D.

$$S=y[0]+y[1]+y[2]+y[3]=3(A+B+C+D)$$

Accordingly, the A, B, C, and D may be obtained through an equation given below. In the equation given below, all of S, y[0], y[1], y[2], and y[3] are values which may be measured and obtained by using the touch sensing signal output unit.

$$A=(S-3*y[3])/3,$$

$$B=(S-3*y[2])/3,$$

$$C=(S-3*y[1])/3,$$

$$D=(S-3*y[0])/3.$$

Hereinafter, a touch input information calculating method according to an exemplary embodiment of the present invention will be described with reference to FIG. 20C.

The method uses first information including a definition of p time periods T_v and second information which is defined to correspond to each of the p time periods T_v and includes definition for p driving electrode sets TEC_v configured by N_v driving electrode pads selected from a plurality (=M) of driving electrode pads. In addition, the method is a method for calculating information on a touch input with respect to any one driving electrode pad among the plurality of driving electrode pads by using a touch sensing circuit 600 including a charge accumulation capacitor (e.g., Cfb) connected to the sensing electrode pad (e.g., 2205) adjacent to the plurality of driving electrode pads. However, v is an integer of 1 to p and p is an integer of 2 or more.

For example, in the example of FIG. 20C, p=4, T_1=521, T_2=522, T_3=523, T_4=524, M=4, N_1=3, N_2=3, N_3=3, N_4=3, TEC_1={first driving electrode pad 201, second driving electrode pad 202, and third driving electrode pad 203}, TEC_2={first driving electrode pad 201, second driving electrode pad 202, and fourth driving electrode pad 204}, TEC_3={first driving electrode pad 201, third driving electrode pad 203, and fourth driving electrode pad 204}, and TEC_4={second driving electrode pad 2021, third driving electrode pad 203, and fourth driving electrode pad 204}.

In this case, different driving electrode combinations which belong to the p driving electrode combinations are constituted by driving electrode pads of different combinations. That is, all of TEC_1={201, 202, 203}, TEC_2={201, 202, 204}, TEC_3={201, 203, 204}, and TEC_4={202, 203, 204} are different combinations.

The method includes obtaining an output value TO_v from the touch sensing circuit 600 by using a scheme of applying driving voltage only to all driving electrode pads that belong to a driving electrode combination TEC_v and not applying the driving voltage to the residual driving electrode pads during the time period T_v.

For example, referring to FIGS. 20C and 20D, a driving electrode driving signal may be applied to all driving electrode pads 201, 202, and 203 that belong to the driving electrode combination TEC_1 during the first time period (T_1) 521. In addition, an output TO_1=y[0] of the touch sensing circuit 600 may be obtained during the first time period (T_1) 521.

In addition, the driving electrode driving signal may be applied to all driving electrode pads 201, 202, and 204 that belong to the driving electrode combination TEC_2 during the second time period (T_2) 522. In addition, an output TO_2=y[1] of the touch sensing circuit 600 may be obtained during the first time period (T_2) 522.

Moreover, the driving electrode driving signal may be applied to all driving electrode pads 201, 203, and 204 that belong to the driving electrode combination TEC_3 during the third time period (T_3) 523. Besides, an output TO_3=y[2] of the touch sensing circuit 600 may be obtained during the third time period (T_3) 523.

Moreover, the driving electrode driving signal may be applied to all driving electrode pads 202, 203, and 204 that belong to the driving electrode combination TEC_4 during the fourth time period (T_4) 524. In addition, an output TO_4=y[3] of the touch sensing circuit 600 may be obtained during the fourth time period (T_4) 524.

Moreover, the method may include calculating information on a mutual capacitance between the plurality of driving electrode pads and the sensing electrode pad by using p output values TO_v.

That is, in the example of FIG. 20C, information on the mutual capacitance between any one driving electrode pad that belongs to the plurality of driving electrode pads and the sensing electrode pad may be calculated by using p (=4) output values y[0], y[1], y[2], and y[3]. As a result, whether the touch is input in an area between the any one driving electrode pad and the sensing electrode pad may be verified.

In this case, the plurality of driving electrode pads may be arranged in the matrix form. Alternatively, the plurality of driving electrode pads may be arranged in zigzag as a honeycomb structure. In addition, the sensing electrode pad may be disposed around the plurality of driving electrode pads.

In this case, the plurality of driving electrode pads and the sensing electrode pad are provided as a separate module distinguished from a display panel to be disposed on the display panel. In this case, the display panel may be one of a TFT panel and an IPS panel, but is not limited to a specific type.

Alternatively, the plurality of driving electrode pads and the sensing electrode pad may be a plurality of divided common electrodes which is used as a component of the display panel for an operation of the display panel. In this case, during the p time periods T_v, the plurality of driving electrode pads and the sensing electrode pad may be connected to the touch sensing circuit 600.

In this case, the plurality of driving electrode pads and the sensing electrode pad may be all connected to a predetermined reference potential Vref2 during at least some periods among periods other than the p time periods T_v.

In this case, the sensing electrode pad may be adjacent to all of the plurality of driving electrode pads. That is, other electrode pads that are present in the touch panel may never be disposed between the sensing electrode pad and the plurality of driving electrode pads.

Hereinafter, a touch input detecting method according to another exemplary embodiment of the present invention will be described with reference to FIGS. 20B, 20C, and 20D. The method may include, a first step of obtaining a first output value from the touch sensing circuit 600 connected to the sensing electrode pad 2205 capacitively coupled with M driving electrode pads 201, 202, 203, and 204 by applying the driving signal only to the driving electrode pads 201, 202, and 203 of the first combination selected among M (=4) driving electrode pads 201, 202, 203, and 204 during the first time period (e.g., 521);

a second step of obtaining a second output value from the touch sensing circuit 600 by applying the driving signal only to the driving electrode pads 201, 202, and 204 of the second combination selected among the M driving electrode pads 201, 202, 203, and 204 during the second time period (e.g., 522); and a third step of calculating information on a touch input with respect to an area between the first driving electrode pad among the M driving electrode pads and the sensing electrode pad by using the first and second output values.

Exemplary Embodiment: Method of Sensing Touch Input by Mutual Capacitance Method by Using Electrode Pads Arranged in Matrix Form and Device Therefor FIGS. 21A to 21C illustrate a structure to which a method for sensing a touch input in a mutual capacitance method by using electrode pads arranged in a tile structure can be applied according to another exemplary embodiment of the present invention.

An array of the electrode pads of FIG. 21A may be the same as that of FIG. 15. However, FIG. 21A illustrates a structure in which some electrode pads are used as the driving electrode pads and other electrode pads are used as the sensing electrode pads to sense the touch input in the mutual capacitance method.

In FIG. 21A, a total of 20*12=240 electrode pads are arranged and the electrode pads are labeled with signs 1 to 9 and A to G, respectively. Among them, all the electrode pads labeled with 1, 3, 5, 7, 9, B, D, E, F, and G may be used as the driving electrode pads and all the electrode pads labeled with 2, 4, 6, 8, A, and C may be used as the sensing electrode pads.

In addition, all of the driving electrode pads labeled with #1 may be electrically connected to each other by internal switches. This may be similarly applied even to the driving electrode pads labeled with 3, 5, 7, 9, B, D, E, F, and G.

Further, all of the driving electrode pads labeled with #2 may be electrically connected to each other by the internal switches. This may be similarly applied even to the sensing electrode pads labeled with 4, 6, 8, A, and C.

As a result, the arranged configuration illustrated in FIG. 21A may be conceptualized as 6 sensing electrode pads which extend vertically and 10 driving electrode pads which extend horizontally as illustrated in FIG. 21B. In FIG. 21B, the touch panel is depicted like a two layered mutual capacitive touch panel in which the driving electrode pads are disposed on a first layer and the sensing electrode pads are disposed on a second layer, but this is depicted only for convenience and actually, all electrode pads may be disposed on the same layer. Whether the respective electrode pads are disposed on the same layer may vary depending on the exemplary embodiment.

According the present exemplary embodiment, a mutual capacitive touch input scheme constituted by 6 sensing electrode sand 10 driving electrodes may be implemented.

Hereinafter, a touch input device according to an exemplary embodiment of the present invention will be described with reference to FIGS. 21A to 21C. The touch input device is configured to sense the touch input in the mutual capacitance method by using the plurality of electrode pads 1 to 9 and A to G disposed in a matrix structure on the first layer. In addition, the touch input device may include a sensing electrode (e.g., 403) formed by electrically connecting to each other electrode pads that are present on an even-numbered row (e.g., R2) of a first column (e.g., C1) among the plurality of electrode pads and electrode pads that are present on an odd-numbered row (e.g., R1) of a second column (e.g., C2) adjacent to the first column. In addition, the touch input device may include a driving electrode (e.g., 404) formed by electrically connecting to each other electrode pads that are present on the odd-numbered row (e.g., C1) of the first row (e.g., R1) among the plurality of electrode pads and electrode pads that are present on the even-numbered column (e.g., C2) of the second row (e.g., R2) adjacent to the first row. Moreover, the touch input device may include an electrode pad potential control unit 401 configured to apply the driving signal to the driving electrode and a touch sensing circuit 402 in which the charge accumulation capacitor is connected to the sensing electrode. In this case, the touch sensing circuit 402 may include one or more touch input circuits described in FIG. 1F.

In this case, four electrode pads are arranged in the matrix form in an area 405 where the sensing electrode (e.g., 403) and the driving electrode (e.g., 404) cross each other, and when the driving signal is applied to the driving electrode, a mutual capacitance is configured to be formed between two electrode pads that belong to the sensing electrode among the four electrode pads and two electrode pads that belong to the driving electrode among the four electrode pads.

In this case, the plurality of electrode pads and the sensing electrode pad are provided separately from the display panel to be disposed on the display panel. In this case, the display panel may be any one of the TFT panel and the IPS panel.

Alternatively, the plurality of driving electrode pads and the sensing electrode pad may be a plurality of divided common electrodes which is used as the component of the display panel for the operation of the display panel. In this case, for a first time period, all of the plurality of electrode pads are connected to the electrode pad potential control unit or the touch sensing circuit, and for at least some time periods except for the first time period, all of the plurality of electrode pads are connected to a predetermined reference potential Vref2.

Exemplary Embodiment: Touch Input Method of Switching Mutual Capacitance Method and Self Capacitance Method and Touch Input Device Therefor In an exemplary embodiment of the present invention, a first case in which the touch input is achieved on any part of the touch panel and a second case in which the touch input is achieved on at least one part are distinguished and in the respective cases, different touch input schemes may be adopted.

For example, in the first case, any one of the self capacitive touch input methods may be used and in the second case, any one of the capacitive touch input methods may be used. Alternatively, the reverse is also possible.

FIGS. 22A and 22B illustrate a switching order of the touch input method of the touch input device according to an exemplary embodiment of the present invention. In this case, the touch input device may be a predetermined touch input device among the touch input devices opened in the present specification.

In step S201, the touch input device is initialized, and as a result, touch sensing starts.

In step S202, a touch input may be detected by a self capacitance method during the initialization. Herein, the self capacitance method may be a predetermined method among the exemplary embodiments of the self capacitance methods.

In step S203, it is determined whether the touch input is detected. A mode is switched so that the touch input is detected by the self capacitance method when the touch input is not detected and the touch input is detected by the mutual capacitance method when the touch input is detected.

In step S204, the touch input is detected by the mutual capacitance method. In this step, the touch input may be continuously achieved without a pause.

In step S205, it is determined whether the touch input disappears. When the touch input disappears, the process returns to step S202 and when the touch input does not disappear, the touch input may be continuously detected by the mutual capacitance method.

FIG. 22B is a flowchart illustrating an exemplary embodiment in which the touch in put is detected by the mutual capacitance method as default when the touch input device is initialized and the touch sensing thus starts and the touch input is detected by the self capacitance method while the touch input is consecutively achieved on the contrary to the order of FIG. 22A.

FIG. 22C illustrates a configuration of a touch input device according to an exemplary embodiment of the present invention.

Hereinafter, a touch input device according to an exemplary embodiment of the present invention will be described with reference to FIGS. 22A to 22C.

The touch input device may include a touch sensing unit 810 configured to sense a touch input by selecting any one of a mutual capacitance method and a self capacitance method; a plurality of electrode pads 820 which is electrically connected to the touch sensing unit 810 and arranged in a matrix form; and a touch pad control unit 830 controlling the touch sensing unit 810 to perform touch sensing for the plurality of electrode pads 820 by the self capacitance method in a first mode and perform the touch sensing for the plurality of electrode pads 820 by the mutual capacitance method in a second mode.

In this case, the touch sensing unit 810 may include a first touch sensing circuit 811 sensing the touch input by the self capacitance method, a second touch sensing circuit 812 sensing the touch input by the mutual capacitance method, and a switch unit 815. The touch pad control unit 830 may be configured to selectively connect the plurality of electrode pads 820 to the first touch sensing circuit 811 or the second touch sensing circuit 812 by controlling the switch unit 815 according to the first mode and the second mode.

The first touch sensing circuit 811 may be the self capacitive sensing circuit illustrated in FIGS. 1A, 1C, 2A, 2B, 11, 13, and the like. The second touch sensing circuit 812 may be the mutual capacitive sensing circuit illustrated in FIGS. 1F, 17E, 17F, 18A, 18B, 20B, and the like.

In this case, the touch pad control unit 830 may perform the touch sensing for the plurality of electrode pads 820 by the self capacitance method while the touch input to the plurality of electrode pads 820 is not sensed and perform the touch sensing for the plurality of electrode pads 820 by the mutual capacitance method while the touch input to the plurality of electrode pads 820 is sensed.

On the contrary, the touch pad control unit 830 may perform the touch sensing for the plurality of electrode pads 820 by the mutual capacitance method while the touch input to the plurality of electrode pads 820 is not sensed and perform the touch sensing for the plurality of electrode pads 820 by the self capacitance method while the touch input to the plurality of electrode pads 820 is sensed.

In this case, the plurality of electrode pads 820 may be provided separately from the display panel to be arranged on the display panel. In this case, the display panel may be any one of the TFT panel and the IPS panel.

Alternatively, the plurality of electrode pads 820 may be a plurality of divided common electrodes which is used as the component of the display panel for the operation of the display panel. In this case, for a first time period, all of the plurality of electrode pads are connected to the touch sensing unit, and for at least some time periods except for the first time period, all of the plurality of electrode pads may be connected to a predetermined reference potential Vref2.

Hereinafter, according to another exemplary embodiment of the present invention, a method of sensing a touch input in the touch input device including the plurality of electrode pads will be described. This method may include detecting whether a touch is input with respect to the plurality of electrode pads by using a first sensing method when the touch input device is initialized; detecting whether the touch is input with respect to the plurality of electrode pads by using a second sensing method when it is determined that the touch is input with respect to the plurality of electrode pads;

and detecting whether the touch is input with respect to the plurality of electrode pads by using the first sensing method when it is determined that the touch input disappears with respect to the plurality of electrode pads. In this case, the first sensing method is the self capacitance method and the second sensing method is the mutual capacitance method. Alternatively, the first sensing method may be the mutual capacitance method and the second sensing method may be the self capacitance method.

By using the exemplary embodiments of the present invention, those skilled in the art will be able to easily perform various changes and modifications within the scope without departing from an essential characteristic of the present invention. Contents in each claim of Claims may be coupled to other claims having a citation relationship so as to be appreciated through the specification.

The invention claimed is:

1. A touch input sensing device comprising:
   a touch input sensing electrode;
   a touch sensing unit connected to one point of the touch input sensing electrode to measure a change in a touch capacitance formed by the touch input sensing electrode according to a touch input;
   a second node included in the touch input sensing device to form a capacitance between the one point and the second node; and
   a potential control unit for providing a potential value following the potential of the one point to the second node to decrease a potential difference between the one point and the second node;
   wherein a waveform of periodic voltage signal is provided to the one point and the following potential value provided to the second node has the same phase as the waveform of periodic voltage provided to the one point.

2. The touch input sensing device of claim 1, wherein a screen output device includes image pixels, a control line transferring a signal for controlling light output of the image pixels, and a common electrode of the image pixels, and
   the touch input sensing electrode is the common electrode of the screen output device.

3. The touch input sensing device of claim 1, wherein a screen output device includes image pixels, a control line transferring the signal for controlling light output of the image pixels, and a common electrode of the image pixels, and
   wherein the second node is present in the control line of the screen output device.

4. The touch input sensing device of claim 3, wherein the control line is a data control line for the image pixels or a gate control line for the image pixels.

5. The touch input sensing device of claim 2, wherein the screen output device is a TFT-LCD.

6. The touch input sensing device of claim 1, wherein:
   the touch input sensing electrode is a first common electrode among the plurality of common electrodes of a screen output device, which includes a plurality of image pixels, a plurality of control lines transferring a signal for controlling light output of the plurality of image pixels, and a plurality of common electrodes divided and provided for the plurality of image pixels, and
   the following potential value is a potential value of any one common electrode selected by a predetermined method among the plurality of common electrodes.

7. The touch input sensing device of claim 1, wherein:
   the touch input sensing electrode is a first common electrode among the plurality of common electrodes of a screen output device, which includes a plurality of image pixels, a plurality of control lines transferring a signal for controlling light output of the plurality of image pixels, and a plurality of common electrodes divided and provided for the plurality of image pixels, and
   the following potential value is an average value of potential values of the plurality of common electrodes.

8. The touch input sensing device of claim 1, wherein:
   the touch input sensing electrode includes
   the common electrode of the screen output device, which includes image pixels, a control line transferring a signal for controlling light output of the image pixels, and a common electrode of the image pixels, and
   a period of the following potential value is the same as a period of the common electrode.

9. The touch input sensing device of claim 1, wherein:
   the touch sensing unit includes an operation amplifier,
   a signal having a first frequency component is applied to a first input terminal of the operation amplifier and the second node, and
   the touch input sensing electrode is connected to a second input terminal of the operation amplifier.

10. The touch input sensing device of claim 9, wherein a screen output device includes image pixels, a control line transferring a signal for controlling light output of the image pixels, and a common electrode of the image pixels, and
    wherein the touch input sensing electrode is the common electrode of the screen output device.

11. The touch input sensing device of claim 9, wherein a screen output device includes image pixels, a control line transferring a signal for controlling light output of the image pixels, and a common electrode of the image pixels, and
    wherein the second node is present in the control line of the screen output device.

12. A user device including a touch input sensing device and a screen output device, wherein:
    the touch input sensing electrode includes
    1) a touch input sensing electrode;
    2) a touch sensing unit connected to one point of the touch input sensing electrode to measure a change in a touch capacitance formed by the touch input sensing electrode according to a touch input;
    3) a second node included in the touch input sensing device to form a capacitance between the one point and the second node; and
    4) a potential control unit for providing a potential value following the potential of the one point to the second node to decrease a potential difference between the one point and the second node, in which a waveform of periodic voltage signal is provided to the one point and the following potential value provided to the second node has a same phase to the waveform of periodic voltage provided to the one point, and
    the screen output device includes
    5) image pixels;
    6) a control line transferring a signal for controlling light output of the image pixels; and
    7) a common electrode of the image pixels, and
    the common electrode is the touch input sensing electrode.

13. The user device of claim 12, wherein the second node is present in the control line.

14. The user device of claim 13, wherein the screen output device is a TFT-LCD.

15. The user device of claim 12, wherein:
the screen output device includes a plurality of image pixels, a plurality of control lines transferring a signal for controlling a light output of the plurality of image pixels, and a plurality of common electrodes divided and provided for the plurality of image pixels,
the touch input sensing electrode is a first common electrode among the plurality of common electrodes, and
the following potential value is a potential value of any one common electrode selected by a predetermined method among the plurality of common electrodes.

16. The user device of claim 12, wherein:
the screen output device includes a plurality of image pixels, a plurality of control lines transferring a signal for controlling a light output of the plurality of image pixels, and a plurality of common electrodes divided and provided for the plurality of image pixels,
the touch input sensing electrode is a first common electrode among the plurality of common electrodes, and
the following potential value is an average value of potential values of the plurality of common electrodes.

17. The user device of claim 12, wherein a period of the following potential value is the same as a period of the common electrode.

18. The user device of claim 12, wherein:
the touch sensing unit includes an operation amplifier,
a signal having a first frequency component is applied to a first input terminal of the operation amplifier and the second node, and
the touch input sensing electrode is connected to a second input terminal of the operation amplifier.

* * * * *